(12) United States Patent
Maloney et al.

(10) Patent No.: US 11,510,942 B1
(45) Date of Patent: *Nov. 29, 2022

(54) STABLE, HIGHLY PURE L-CYSTEINE COMPOSITIONS FOR INJECTION AND METHODS OF USE

(71) Applicant: Exela Pharma Sciences, LLC, Lenoir, NC (US)

(72) Inventors: John Maloney, Salisbury, NC (US); Aruna Koganti, Lenoir, NC (US); Phanesh Koneru, Waxhaw, NC (US)

(73) Assignee: EXELA PHARMA SCIENCES, LLC, Lenoir, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/188,922

(22) Filed: Mar. 1, 2021

Related U.S. Application Data

(63) Continuation of application No. 16/746,028, filed on Jan. 17, 2020, now Pat. No. 10,933,089, which is a
(Continued)

(51) Int. Cl.
*A61K 31/4172* (2006.01)
*A61K 33/06* (2006.01)
(Continued)

(52) U.S. Cl.
CPC ............ *A61K 33/06* (2013.01); *A23L 33/16* (2016.08); *A23L 33/175* (2016.08);
(Continued)

(58) Field of Classification Search
CPC .......................... A61K 8/447; A61K 31/4172
See application file for complete search history.

(56) References Cited

U.S. PATENT DOCUMENTS

| 4,385,086 A | 5/1983 | Nakayama et al. |
| 6,051,567 A | 4/2000 | Abrahamson et al. |

(Continued)

OTHER PUBLICATIONS

Joint Claim Construction Brief, *Exela Pharma Sciences. v. Eton Pharmaceuticals, Inc.*, No. 1:20-cv-365 (MN), (U.S. Distr. Del. Feb. 8, 2022), Jul. 21, 2021.
(Continued)

*Primary Examiner* — Benjamin J Packard
(74) *Attorney, Agent, or Firm* — Alston & Bird LLP

(57) ABSTRACT

The subject matter described herein is directed to stable L-cysteine compositions for injection, comprising: L-cysteine or a pharmaceutically acceptable salt thereof and/or hydrate thereof in an amount from about 10 mg/mL to about 100 mg/mL; Aluminum in an amount from about 1.0 parts per billion (ppb) to about 250 ppb; cysteine in an amount from about 0.01 wt % to about 2 wt % relative to L-cysteine; pyruvic acid in an amount from about 0.01 wt % to about 2 wt % relative to L-cysteine; a pharmaceutically acceptable carrier, comprising water; headspace $O_2$ that is less than 1.0%; dissolved oxygen present in the carrier in an amount from about 0.01 parts per million (ppm) to about 1 ppm, wherein the composition is enclosed in a single-use container having a volume of from 10 mL to 100 mL. Also described are compositions for a total parenteral nutrition regimen and methods for their use.

34 Claims, 5 Drawing Sheets

Related U.S. Application Data continuation of application No. 16/665,702, filed on Oct. 28, 2019, now Pat. No. 10,583,155, which is a continuation of application No. 16/248,460, filed on Jan. 15, 2019, now Pat. No. 10,478,453.

(51) Int. Cl.

| | | |
|---|---|---|
| *A61K 31/191* | (2006.01) | |
| *A61K 47/02* | (2006.01) | |
| *A61K 33/36* | (2006.01) | |
| *A61K 33/241* | (2019.01) | |
| *A61K 33/28* | (2006.01) | |
| *A61K 33/00* | (2006.01) | |
| *A61K 31/405* | (2006.01) | |
| *A61K 31/401* | (2006.01) | |
| *A61K 9/00* | (2006.01) | |
| *A23L 33/175* | (2016.01) | |
| *A23L 33/16* | (2016.01) | |
| *A61K 31/198* | (2006.01) | |
| *A61K 31/095* | (2006.01) | |
| *A61J 1/14* | (2006.01) | |

(52) U.S. Cl.
CPC .......... *A61K 9/0029* (2013.01); *A61K 31/095* (2013.01); *A61K 31/191* (2013.01); *A61K 31/198* (2013.01); *A61K 31/401* (2013.01); *A61K 31/405* (2013.01); *A61K 31/4172* (2013.01); *A61K 33/00* (2013.01); *A61K 33/241* (2019.01); *A61K 33/28* (2013.01); *A61K 33/36* (2013.01); *A61K 47/02* (2013.01); *A23V 2002/00* (2013.01); *A61J 1/1412* (2013.01)

(56) References Cited

U.S. PATENT DOCUMENTS

| | | |
|---|---|---|
| 6,382,442 B1 | 5/2002 | Thibault et al. |
| 6,992,218 B2 | 1/2006 | Dietlin et al. |
| 7,323,206 B1 | 1/2008 | Driscoll et al. |
| 8,415,337 B1 | 4/2013 | Krishna |
| 9,220,700 B2 | 12/2015 | Savarese et al. |
| 10,478,453 B1 | 11/2019 | Maloney et al. |
| 10,493,051 B1 | 12/2019 | Sutterer et al. |
| 10,543,186 B1 | 1/2020 | Sutterer et al. |
| 10,583,155 B1 | 3/2020 | Maloney et al. |
| 10,653,719 B1 | 5/2020 | Maloney et al. |
| 10,905,713 B2 | 2/2021 | Maloney et al. |
| 10,905,714 B1 | 2/2021 | Maloney et al. |
| 10,912,795 B1 | 2/2021 | Maloney et al. |
| 10,918,662 B1 | 2/2021 | Maloney et al. |
| 10,933,089 B1 | 3/2021 | Maloney et al. |
| 2013/0116215 A1* | 5/2013 | Coma .................. A61K 31/655 514/357 |
| 2019/0233153 A1 | 8/2019 | Hofstetter |
| 2019/0247307 A1 | 8/2019 | Hofstetter |

OTHER PUBLICATIONS

Joint Claim Construction Chart, *Exela Pharma Sciences, v. Eton Pharmaceuticals, Inc.*, No. 1:20-cv-365 (MN), (U.S. Distr. Del. Feb. 8, 2022), Feb. 12, 2021.
Joint Claim Construction Chart, *Exela Pharma Sciences, v. Eton Pharmaceuticals, Inc.*, No. 1:20-cv-365 (MN), (U.S. Distr. Del. Feb. 8, 2022), May 5, 2021.
"Aluminum in large and small volume parenterals used in total parenteral nutrition," Food and Drug Administration, 21 C.F.R. § 201.323, 89-90, (2003).
"American Regent Announces the Launch and Availability of Selenious Acid Injection, USP," Press Release, American Regent, Inc., 6 pages, (2019).
"Cysteine," DrugBank, 23 pages, Exhibit 1016, Petition for Post Grant Review of U.S. Pat. No. 10,478,453, *Eton Pharmaceuticals, Inc. v. Exela Pharma Sciences, LLC*, PGR2020-00064, (PTAB May 19, 2020).
"Elcys(cysteine hydrochloride injection), for intravenous use [Label and Highlights of Prescribing Information]," Exela Pharma Sciences, LLC, 9 pages, (2019).
"Elcys (Cysteine Hydrochloride)," NDA 210666, Orange Book: Approved Drug Products with Therapeutic Equivalence Evaluations, 3 pages, (2019).
"Guidelines for the Use of Parenteral and Enteral Nutrition in Adult and Pediatric Patients," ASPEN Board of Directors and the Clinical Guidelines Task Force, Journal of Parenteral and Enteral Nutrition, 26(1 Suppl.):1SA-138SA, (2002).
"Neonatal Parenterai Nutrition," Intensive Care Nursery House Staff Manual, UCSF Children's Hospital, pp. 136-142, (2004-2006).
"Acetadote (acetylcysteine) injection, for intravenous use: Prescribing Information [package insert]," Cumberland Pharmaceuticals Inc., 12 pages, (2017).
"Aluminum in Large and Small Volume Parenterals Used in Total Parenteral Nutrition," Federal Register, 63(2):176-185, (1998).
"Aluminum in Large and Small Volume Parenterals Used in Total Parenteral Nutrition," Federal Register, 65(17):4103-4111, (2000).
"Aluminum in Large and Small Volume Parenterals Used in Total Parenteral Nutrition; Delay of Effective Date," Federal Register, 66(18):7864-7865, (2001).
"Aminosyn[label information]", Hospira, Inc., 11 pages, Exhibit 1009, Petition for Post Grant Review of U.S. Pat. No. 10,478,453, *Eton Pharmaceuticals, Inc. v. Exela Pharma Sciences, LLC*, PGR2020-00064, (PTAB May 19, 2020).
"Aminosyn [prescribing information and label]," Hospira, Inc., 19 pages, (2012).
"Aminosyn [prescribing information and label]," Hospira, Inc., 28 pages, (2019).
"Aminosyn Sulfite Free [drug information]," RX List, 15 pages, Exhibit 1052, Petition for Post Grant Review of U.S. Pat. No. 10,478,453, *Eton Pharmaceuticals, Inc. v. Exela Pharma Sciences, LLC*, PGR2020-00064, (PTAB May 19, 2020).
"ASHP Guidelines on the Safe Use of Automated Compounding Devices for the Preparation of Parenteral Nutrition Admixtures," Automation and Information Technology—Guidelines, 63-67, (2000).
"Chapter 18: Preparation of Parenteral Nutrition," Aseptic Processing Manual, NHS Technical Specialist Education and Training Group, 24 pages, (2018).
"Cysteine Hydrochloride [FDA package insert]," Hospira, Inc., 7 pages, (2007).
"Cysteine Hydrochloride Injection [Material Safety Data Sheet]," Hospira Inc., 6 pages, (2011).
"Cysteine Hydrochloride Injection [prescribing information]," Hospira, Inc., 4 pages, (2004). [Retrieved from the Internet Dec. 28, 2016: <URL: https://dailymed.nlm.nih.gov/dailymed/archives/fdaDrugInfo.cfm?archiveid=113819>].
"Cysteine," TOXNET: Toxicology Data Network, National Library of Medicine HSDB Database, 20 pages, (2016). [Retrieved from the Internet Jun. 27, 2017: <URL: https://toxnet.nlm.nih.gov/cgi-bin/sis/search/a?dbs+hsdb:@term+@DOCNO+2109>].
"Cysteine: Pediatric drug information," Lexicomp, Inc., 4 pages, (1978).
"Determination That Cysteine Hydrochloride Injection, USP, 7.25%, Was Not Withdrawn From Sale for Reasons of Safety or Effectiveness," Federal Register, 75(107):31790-31791, (2010).
"Effect of L-Cysteine (Acetium® Capsules) in Restoration of the Structure and Function of Gastric Mucosa After H. pylori Eradication in Patients with Atrophic Gastritis. A randomized, controlled trial.," Study Protocol, BIOHIT HealthCare, 45 pages, (2016).
"Guidance for Industry: E11 Clinical Investigation of Medicinal Products in the Pediatric Population," U.S. Dept. of Health and Human Services, FDA, CDER, CBER, 17 pages, (2000).
"Guidance for Industry: Q1A(R2) Stability Testing of New Drug Substances and Products," U.S. Dept. of Health and Human Services, FDA, CDER, CBER, 25 pages, (2003).

(56) References Cited

OTHER PUBLICATIONS

"Guidance for Industry: Q8(R2) Pharmaceutical Development," U.S. Dept. of Health and Human Services, FDA, CDER, CBER, 29 pages, (2009).
"Guideline on the Use of Parenteral Nutrition in Neonatal and Paediatric Units," Clinical Practice Guideline, Royal College of Physicians in Ireland, 46 pages, (2016).
"International Conference on Harmonisation; Guidance on Q6A Specifications: Test Procedures and Acceptance Criteria for New Drug Substances and New Drug Products: Chemical Substances," Federal Register, 65(251):83041-83063, (2000).
"L-Cysteine [product information]," Sigma-Aidrich, Inc., 2 pages, (2003).
"L-Cysteine Hydrochloride—cysteine hydrochioride injection, solution [label information]", Sandoz Inc., 11 pages, Exhibit 1005, Petition for Post Grant Review of U.S. Pat. No. 10,478,453, *Eton Pharmaceuticals, Inc. v. Exela Pharma Sciences, LLC*, PGR2020-00064, (PTAB May 19, 2020).
"L-Cysteine Hydrochloride [prescribing information and label]", Sandoz Inc., 6 pages, (2010).
"L-Cysteine Hydrochloride Injection, USP [prescribing information]," American Regent, Inc., 2 pages, (2009).
"L-Cysteine Hydrochloride Injection, solution [drug label information]", Sandoz Inc., (2018).
"L-Cysteine Hydrochloride Monohydrate [product information]," Sigma-Aldrich, Inc., 1 page, (2006).
"Prosol [prescribing information and label]," Baxter Healthcare Corporation, 14 pages, (2014).
"Q3D Elemental Impurities: Guidance for Industry," U.S. Dept. of Health and Human Services, FDA, CDER, CBER, 85 pages, (2015).
"Safe Practices for Parenteral Nutrition Formulations," National Advisory Group on Standards and Practice Guidelines for Parenteral Nutrition, Journal of Parenteral and Enteral Nutrition, 22(2):49-66, (1998). [Retrieved from the Internet Mar. 12, 2015: <URL: https://onlinelibrary.wiley.com/doi/10.1177/014860719802200249>].
"Scientific Opinion on the safety and efficacy of L-cysteine hydrochloride monohydrate as a flavouring additive for pets," European Food Safety Authority Journal, 11(10):3437, 13 pages, (2013).
"Selenious Acid Injection [prescribing information]," American Regent, Inc., 8 pages, (2019).
"The Provision of Parenteral Nutrition within Neonatal Services—A Framework for Practice," British Association of Perinatal Medicine, 27 pages, (2016).
"Total Parenteral Nutrition (TPN)—Administration in Adult Ward Areas and Intensive Care of St. George Hospital Only," St. George/Sutherland Hospitals and Health Services, NSW Government Health South Eastern Sydney Local Health Network, 10 pages, (2013). [Retrieved from the Internet May 11, 2020: <URL: https://www.aci.health.nsw.gov.au/_data/assets/pdf_file/0006/306438/stgeorgeTotal_Parenteral_Nutrition_ICU_Adult_Wards_SGSHHS_CLIN089.pdf>].
"Travasol [prescribing information and label]," Baxter Healthcare Corporation, 19 pages, (2017).
"Trophamine [prescribing information and label]," B. Braun Medical Inc., 21 pages, (2014).
"Trophamine® (Amino Acid injections) [package insert]," B. Braun Medical Inc., pp. 5-16, (2003).
"Zinc sulfate injection [prescribing information]," American Regent, Inc., 9 pages, (2019).
Abdulrazik et al., "Formulation for Slow Release of Oral Radiation—Protection Drugs," Int. J. Nucl. Med. Biol., 11(1):53-54, (1984).
Advenier et al., "Aluminum Contamination of Parenteral Nutrition and Aluminum Loading in Children on Long-Term Parenteral Nutrition," Journal of Pediatric Gastroenterology and Nutrition, 36(4):448-453, (2003). [Retrieved from the Internet Jun. 6, 2018: <URL: https://journals.lww.com/jpgn/Fulltext/2003/04000/Aluminum_Contamination_of_Parenteral_Nutrition_and.5.aspx#pdf-link>].

Affadavit of Christopher Butler, Exhibit 1004, Petition for Post Grant Review of U.S. Pat. No. 10,478,453, *Eton Pharmaceuticals, Inc. v. Exela Pharma Sciences, LLC*, PGR2020-00064, (PTAB May 19, 2020).
Affadavit of Christopher Butler, Exhibit 1010, Petition for Post Grant Review of U.S. Pat. No. 10,478,453, *Eton Pharmaceuticals, Inc. v. Exela Pharma Sciences, LLC*, PGR2020-00064, (PTAB May 19, 2020).
Ahola et al., "N-Acetylcysteine does not Prevent Bronchopulmonary Dysplasia in Immature Infants: A Randomized Controlled Trial," J Pediatr, 143:713-719, (2003).
Akers, Michael J., "Parenterai Preparations," Remington: The Science and Practice of Pharmacy, 21st ed., Ed. David B. Troy, Baltimore: Lippincott Williams & Wilkins, pp. 802 and 808-813, (2006).
Akers, Michael J., Sterile Drug Products: Formulation, Packaging, Manufacturing, and Quality, New York: Informa Healthcare, (2010).
Allen, Jr., Loyd V., "L-Cysteine Hydrochloride 50 mg/mL Injection," U.S. Pharmacist, 36(9):41-42, (2011). [Retrieved from the Internet May 26, 2016: <URL:https://www.uspharmacist.com/article/lcysteinehydrochloride50mgmlinjection>].
Allen, Loyd V., "Chapter 1: Guidelines for Compounding Practices," The Art, Science, and Technology of Pharmaceutical Compounding, 4th Ed.:1-18, (2012).
Allwood et al., "Compatibility and Stability of Additives in Parenteral Nutrition Admixtures," Nutrition, 14(9):697-706, (1998).
Amended Complaint [redacted], *Exela Pharma Sciences, LLC v. Sandoz, Inc.*, Civil Action No. 1:20-cv-645-MN, (D. Del.., Jun. 1, 2020), ECF No. 12.
Amended Complaint, *Exela Pharma Sciences, LLC v. Eton Pharmaceuticals, Inc.*, Civil Action No. 20-00365-MN, (D. Del., Jul. 28, 2020), ECF No. 14.
Anderson et al., "Physical Compatibility of Calcium Chloride and Sodium Glycerophosphate in Pediatric Parenteral Nutrition Solutions," Journal of Parenteral and Enteral Nutrition, 40(8):1166-1169, (2016, Epub. 2015). [Retrieved from the Internet Oct. 24, 2015: <URL: https://onlinelibrary.wiley.com/doi/epdf/10.1177/0148607115592673>].
Asquith and Hirst, "The Photochemical Degradation of Cystine in Aqueous Solution in the Presence of Air," Biochimica et Biophysica Acta, 184:345-357, (1969).
Avallone et al., "Food and Drug Administration Inspection and Licensing of Manufacturing Facilities," Drug Biotechnology Regulation: Scientific Basis and Practices, Ed. Yuan-yuan H. Chiu et al., New York: Marcel Dekker, Inc., pp. 315-340, (1991).
Ayers et al., "A.S.P.E.N. Parenteral Nutrition Safety Consensus Recommendations," Scholarship and Professional Work—COPHS, Butler University, 66 pages, (2014).
Baines et al., "The Association Between Cysteine, Bone Turnover, and Low Bone Mass," Calcif Tissue Int, 81(6):450-454, (2007).
Balogh, Judit Kovácsné, "Preparation and examination of TPN systems for the individual clinical therapy," (Ph.D. Thesis), Semmelweis University, Hungary, 116 pages, (2007).
Bengoa et al., "Amino acid-induced hypercalciuria in patients on total parenteral nutrition," The American Journal of Clinical Nutrition, 38(2):264-269, (1983). [Retrieved from the Internet Dec. 14, 2017: <URL: https://academic.oup.com/ajcn/article-abstract/38/2/264/4690894>].
Bettner et al., "Effects of pH, Temperature, Concentration, and Time on Particle Counts in Lipid-Containing Total Parenteral Nutrition Admixtures," Journal of Parenteral and Enteral Nutrition, 10(4):375-380, (1986). [Retrieved from the Internet Mar. 10, 2015: <URL: https://onlinelibrary.wiley.com/doi/epdf/10.1177/0148607186010004375>].
Bishop et al., "Aluminum Neurotoxicity in Preterm Infants Receiving Intravenous-Feeding Solutions," The New England Journal of Medicine, 336(22):1557-1561, (1997). [Retrieved from the Internet Jun. 5, 2018: <URL: https://www.nejm.org/doi/full/10.1056/NEJM199705293362203>].
Bistrian, Bruce R., "Brief History of Parenteral and Enteral Nutrition in the Hospital in the USA," Nestlé Nutr Inst Workshop Ser Clin Perform Program, 12:127-136, (2009).

(56) References Cited

OTHER PUBLICATIONS

Bjelton et al., "Availabiiity of Cysteine and of L-2-Oxo-Thiazolidine-4-Carboxylic Acid as a Source of Cysteine in Intravenous Nutrition," Journal of Parenteral and Enteral Nutrition, 14(2):177-182, (1990).

Block et al., "Methionine, Cysteine, Cystine, and Taurine Interrelationships in Human Plasma," The American Journal of Clinical Nutrition, 22(1):33-37, (1969).

Bohrer et al., Aluminum Loading in Preterm Neonates Revisited, JPGN, 51(2):237-241, (2010).

Bohrer et al., "Influence of the glass packing on the contamination of pharmaceutical products by aluminum. Part II: Amino acids for parenteral nutrition," J. Trace Elem. Med. Biol., 15(2-3):103-108, (2001).

Bohrer et al., "Influence of the glass packing on the contamination of pharmaceutical products by aluminum. Part III: Interaction container-chemicals during the heating for sterilisation," J. Trace Elem. Med. Biol., 17(2):107-115, (2003).

Borges-Santos et al., "Plasma glutathione of HIV+ patients responded positively and differently to dietary supplementation with cysteine or glutamine," Nutrition, 28(7-8):753-756, (2012).

Boullata et al., "A.S.P.E.N. Clinical Guidelines: Parenteral Nutrition Ordering, Order Review, Compounding, Labeling, and Dispensing," Journal of Parenteral and Enteral Nutrition, 38(3):334-377, (2014).

Boullata, Joseph I., "Nutrients and Associated Substances," Remington: The Science and Practice of Pharmacy, 21 Ed., Ed. David B. Troy, Philadelphia: Lippincott Williams & Wilkins, pp. 1688-1693, (2005).

Brigham et al., "The Concentrations of Cysteine and Cystine in Human Blood Plasma," J Clin Invest., 39(11):1633-1638, (1960).

Brown et al., "Potential Aluminum Exposure from Parenteral Nutrition in Patients with Acute Kidney Injury," The Annals of Pharmacotherapy, 42(10):1410-1415, (2008).

Bulbul et al., "Letter to the Editor: Nutritional support in preterm infants," Pediatrics and Neonatology, 58(6):562, (2017).

Bullock et al., "Emulsion Stability in Total Nutrient Admixtures Containing a Pediatric Amino Acid Formulation," Journal of Parenteral and Enteral Nutrition, 16(1):64-68, (1992). [Retrieved from the Internet Feb. 10, 2015: <URL: https://onlinelibrary.wiley.com/doi/pdf/10.1177/014860719201600164>].

Butler et al., "Removal of Dissolved Oxygen from Water: A Comparison of Fou Common Techniques," Talanta, 41(2):211-215, (1994).

Cairns, Donald, "Stability of Drugs and Medicines," Essentiais of Pharmaceutical Chemistry, 4th ed., London: Pharmaceutical Press, pp. 217-238, (2012).

Calkins et al., "Effect of High-Dose Cysteine Supplementation on Erythrocyte Glutathione: a Double-Blinded, Randomized Placebo Controlled Pilot Study in Critically Ill Neonates," JPEN J Parenter Enteral Nutr., 40(2):226-234, (2016).

Carlson et al., "Neonatal Parenteral and Enteral Nutrition: A Resource Guide for the Student and Novice Neonatal Nurse Practitioner," National Association of Neonatal Nurse Practitioners, 23 pages, (2010).

Cha et al., "Stability Studies," Handbook of Modern Pharmaceutical Analysis, Ed. Satinder Ahuja and Stephen Scypinski, 2nd ed., vol. 10, Amsterdam: Elsevier, 459-467, and 485-486, (2011).

Citizen Petition, Lachman Consultant Services, Inc., 12 pages, (2018), retrieved from Exhibit 1092, Petition for Post Grant Review of U.S. Pat. No. 10,583,155, *Eton Pharmaceuticals, Inc. v. Exela Pharma Sciences, LLC*, PGR2020-00068, (PTAB Jun. 8, 2020).

Clark et al., "Effects of Two Different Doses of Amino Acid Supplementation on Growth and Blood Amino Acid Levels in Premature Neonates Admitted to the Neonatal Intensive Care Unit: A Randomized, Controlled Trial," Pediatrics, 120(6):1286-1296, (2007).

Clemens et al., "Twice Daily Dosing of Dabigatran for Stroke Prevention in Atrial Fibrillation: A Pharmacokinetic Justification," Curr Med Res Opin, 28(2):195-201, (2012).

Complaint with Request for Temporary Restraining Order, Preliminary and Permanent Injunctions, *Exela Pharma Sciences, LLC v. Sandoz, Inc.*, No. 1:19-cv-318, (W.D.N.C., Nov. 6, 2019).

Connaughton and Fiorello, "Argon or Nitrogen. Which is Best for Your Application?," Parker, 3 pages, (2016).

Connelly et al., "Congenital Hypothyroidism Caused by Excess Prenatal Maternal Iodine Ingestion," The Journal of Pediatrics, 161(4):760-762, (2012).

Copyright Registration Number for Alpsalan Yaman, "Engineering Considerations in Sterile Powder Processes," Sterile Pharmaceutical Products: Process Engineering Applications, Ed. Kenneth E. Avis, Buffalo Grove: Interpharm Press, Inc., (1995).

Copyright Registration Number for Drug Facts & Comparisons, St. Louis: Clinical Drug Information, LLC, (2015).

Courtney-Martin et al., "Plasma Aluminum Concentrations in Pediatric Patients Receiving Long-Term Parenteral Nutrition," Journal of Parenteral and Enteral Nutrition, 39(5):578-585, (2014).

Courtney-Martin et al., "The Addition of Cysteine to the Total Suiphur Amino Acid Requirement as Methionine Does Not Increase Erythrocytes Glutathione Synthesis in the Parenterally Fed Human Neonate," Pediatric Research, 67(3):320-324, (2010).

Darkwa et al., "Antioxidant Chemistry: Oxidation of L-Cysteine and Its Metabolites by Chlorite and Chlorine Dioxide," J. Phys. Chem. A., 108(26):5576-5587, (2004).

De Cloet et al., "Physicochemical stable standard all-in-one parenteral nutrition admixtures for infants and children in accordance with the ESPGHAN/ESPEN guidelines," Nutrition, 49:41-47, (2018).

Decision Denying Institution of Post-Grant Review, *Eton Pharmaceuticals, Inc. v. Exela Pharma Sciences, LLC*, PGR2020-00064, U.S. Pat. No. 10,478,453, (Nov. 18, 2020).

Decision Denying Institution of Post-Grant Review, *Eton Pharmaceuticals, Inc. v. Exela Pharma Sciences, LLC*, PGR2020-00068, U.S. Pat. No. 10,583,155, (Dec. 15, 2020).

Decision Denying Institution of Post-Grant Review, *Eton Pharmaceuticals, Inc. v. Exela Pharma Sciences, LLC*, PGR2020-00086, U.S. Pat. No. 10,653,719, (Apr. 23, 2021).

Declaration of Dr. Robert J. Kuhn, Exhibit 2001, Patent Owner's Preliminary Response, *Eton Pharmaceuticals, Inc. v. Exela Pharma Sciences, LLC*, PGR2020-00064, U.S. Pat. No. 10,478,453, (Aug. 28, 2020).

Declaration of Dr. Robert J. Kuhn, Exhibit 2001, Patent Owner's Preliminary Response, *Eton Pharmaceuticals, Inc. v. Exela Pharma Sciences, LLC*, PGR2020-00068, U.S. Pat. No. 10,583,155, (Sep. 18, 2020).

Declaration of Barrett Rabinow, (2020), Exhibit 1003, Petition for Post Grant Review of U.S. Pat. No. 10,583,155, *Eton Pharmaceuticals, Inc. v. Exela Pharma Sciences, LLC*, PGR2020-00068, (PTAB Jun. 8, 2020).

Declaration of Barrett Rabinow, Exhibit 1003, Petition for Post Grant Review of U.S. Pat. No. 10,478,453, *Eton Pharmaceuticals, Inc. v. Exela Pharma Sciences, LLC*, PGR2020-00064, (PTAB May 19, 2020).

Declaration of Barrett Rabinow, Exhibit 1003, Petition for Post Grant Review of U.S. Pat. No. 10,653,719, *Eton Pharmaceuticals, Inc. v. Exela Pharma Sciences, LLC*, PGR2020-00086, (PTAB Sep. 21, 2020).

Declaration of Daniel Ingles, Exhibit 1078, Petition for Post Grant Review of U.S. Pat. No. 10,478,453, *Eton Pharmaceuticals, Inc. v. Exela Pharma Sciences, LLC*, PGR2020-00064, (PTAB May 19, 2020).

Declaration of Daniel Ingles, Exhibit 1078, Petition for Post Grant Review of U.S. Pat. No. 10,653,719, *Eton Pharmaceuticals, Inc. v. Exela Pharma Sciences, LLC*, PGR2020-00086, (PTAB Sep. 21, 2020).

Declaration of Harry "Warren" Johnson, dated Aug. 24, 2020, Exhibit 1116, Petition for Post Grant Review of U.S. Pat. No. 10,653,719, *Eton Pharmaceuticals, Inc. v. Exela Pharma Sciences, LLC*, PGR2020-00086, (PTAB Sep. 21, 2020).

Declaration of Harry "Warren" Johnson, Exhibit 1022, Petition for Post Grant Review of U.S. Pat. No. 10,478,453, *Eton Pharmaceuticals, Inc. v. Exela Pharma Sciences, LLC*, PGR2020-00064, (PTAB May 19, 2020).

(56) References Cited

OTHER PUBLICATIONS

Declaration of John Geissler, Exhibit 1, Response in Opposition to Plaintiff's Motion for Preliminary Injunction, *Exela Pharma Sciences, LLC v. Sandoz, Inc.*, No. 1:19-cv-318, (W.D.N.C., Dec. 6, 2019).
Declaration of Judy K. He, (2020), Exhibit 1105, Petition for Post Grant Review of U.S. Pat. No. 10,583,155, *Eton Pharmaceuticals, Inc. v. Exela Pharma Sciences, LLC*, PGR2020-00068, (PTAB Jun. 8, 2020).
Declaration of Madan Chilakuri, (2020), Exhibit 1093, Petition for Post Grant Review of U.S. Pat. No. 10,583,155, *Eton Pharmaceuticals, Inc. v. Exela Pharma Sciences, LLC*, PGR2020-00068, (PTAB Jun. 8, 2020).
Declaration of Mark Hartman [redacted], *Exela Pharma Sciences, LLC v. Sandoz, Inc.*, No. 19-cv-00318-MR (W.D.N.C. Dec. 6, 2019), ECF No. 26-1.
Delange, F., "Optimal Iodine Nutrition during Pregnancy, Lactation and the Neonatal Period," Int J Endocrinol Metab, 2(1):1-12, (2004).
Delange, Francois, "Iodine deficiency in Europe and its consequences: an update," Eur J Nucl Med, 29(Suppl. 2):S404-S416, (2002).
Delange, Francois, "iodine requirements during pregnancy, lactation and the neonatai period and indicators of optimal iodine nutrition," Public Health Nutrition: 10(12A):1571-1580, (2007).
Dietary Reference Intakes for Energy, Carbohydrate, Fiber, Fat, Fatty Acids, Cholesterol, Protein, and Amino Acids, The National Academies Press, 1358 pages, (2002). [Retrieved from the Internet Dec. 12, 2017: <URL: http://www.nap.edu/10490>].
Dietary Reference intakes for Vitamin A, Vitamin K, Arsenic, Boron, Chromium, Copper, Iodine, Iron, Manganese, Molybdenum, Nickel, Silicon, Vanadium, and Zinc, National Academy Press, 800 pages, (2000). [Retrieved from the Internet Dec. 16, 2018: <URL: http://www.nap.edu/catalog/10026.html>].
Dilger et al., "Excess Dietary L-Cysteine, but Not L-Cystine, is Lethal for Chicks but Not for Rats or Pigs," The Journal of Nutrition, 137(2):331-338, (2007). [Retrieved from the Internet Jun. 28, 2017: <URL:https://academic.oup.com/jn/article/137/2/331/4664534>].
Domingo et al., "Risks of aluminium exposure during pregnancy," Contributions to Science, 1(4):479-487, (2000).
Drug Facts & Comparisons, "Dietary Reference Intakes of Vitamins and Minerals" and "Intravenous Nutitional Therapy," St. Louis: Clinical Drug Information, LLC, pp. 3-4 and 133-155, (2015).
Dumortier et al., "Development of a Thermogelling Ophthalmic Formulation of Cysteine," Drug Development and Industrial Pharmacy, 32(1):63-72, (2006). [Retrieved from the Internet May 12, 2015: <URL: https://www.tandfonline.com/doi/full/10.1080/03639040500390934>].
El-Shenawy et al., "Nephrotoxicity of sodium valproate and protective role of L-cysteine in rats at biochemical and histological levels," J Basic Clin Physiol Pharmacol, 27(5):497-504, (2016). [Retrieved from the Internet May 4, 2016: <URL: https://www.degruyter.com/view/j/jbcpp.2016.27.issue-5/jbcpp-2015-0106/jbcpp-2015-0106.xml>].
Eton Pharmaceuticals, Inc.'s Answer and Affirmative Defenses to Complaint, (May 6, 2020), *Exela Pharma Sciences, LLC v. Eton Pharmaceuticals, Inc.*, No. 1:20-cv-00365-MN, (D. Del., filed Mar. 16, 2020), retrieved from Exhibit 1077, Petition for Post Grant Review of U.S. Pat. No. 10,478,453, *Eton Pharmaceuticals, Inc. v. Exela Pharma Sciences, LLC*, PGR2020-00064, (PTAB May 19, 2020).
Excerpt from "Parenteral Formulations [Chapter 30]", Bentley's Textbook of Pharmaceutics: An Adaptation, Eds. Sanjay K. Jain et al., pp. 410-415, (2012).
Fewtrell et al., "Aluminium exposure from parenteral nutrition in preterm infants and later health outcomes during childhood and adolescence," Symposium 2: Micronutrients under the Microscope, Proceedings of the Nutrition Society, 70(3):299-304, (2011). [Retrieved from the Internet Jun. 4, 2018: <URL: https://www.cambridge.org/core/journals/proceedings-of-the-nutrition-society/article/aluminium-exposure-from-parenteral-nutrition-in-preterm-infants-and-later-health-outcomes-during-childhood-and-adolescence/F5D0A6109616E8C9D7F8C2C707213860/core-reader>].
Flora et al., "Chelation in Metal Intoxication," Int. J. Environ. Res. Public Health, 7(7):2745-2788, (2010).
Fortenberry et al., "Evaluating Differences in Aluminum Exposure through Parenteral Nutrition in Neonatal Morbidities," Nutrients, 9(11):E1249, 6 pages, (2017).
Fox, Charles J. J., "On the Coefficients of Absorption of Nitrogen and Oxygen in Distilled Water and Sea-Water, and of Atmospheric Carbonic Acid in Sea-Water," Trans. Farad. Soc., 5:68-86, (1909).
Frey et al., "Confirming the Causative Role of Acetaminophen in Indeterminate Acute Liver Failure Using Acetaminophen-Cysteine Adducts," J. Med. Toxicol., 11(2):218-222, (2015).
Friedmann et al., "Reactions of Pyruvic Acid with Thiolacetic Acid and Cysteine," Biochem J, 30(10):1886-1891, (1936).
Fürst et al., "Parenteral nutrition by a solution of crystalline amino acids," Acta Med Scand Suppl., 472:283-293, (1967).
Fusch et al., "Neonatology/Paediatrics—Guidelines on Parenteral Nutrition, Chapter 13," GMS German Medical Science, 7(Doc15):23 pages, (2009).
Gasser et al., "Parenteral Nutrition: Macronutrient Composition and Requirements," Support Line, 27(6):6-12, (2005).
General Advice, NDA 210660, Letter from Department of Health and Human Services to Exela Pharma Sciences, LLC, Aug. 4, 2017.
Ghirri et al., "Iodine Supplementation in the Newborn," Nutrients, 6(1):382-390, (2014).
Gura et al., "Aluminum contamination in products used in parenteral nutrition: Has anything changed?," Nutrition, 26(6):585-594, (2010).
Gura et al., "Recent developments in aluminium contamination of products used in parenteral nutrition," Curr Opin Clin Nutr Metab Care, 9(3):239-246, (2006).
Gura, Kathleen M., "Aluminum contamination in parenteral products," Current Opinions in Clinical Nutrition and Metabolic Care, 17(6):551-557, (2014).
Guzman Barron, E.S., "Thiol Groups of Biological Importance," Advances in Enzymology and Related Areas of Molecular Biology, vol. 11, Ed. F. F. Nord, New York: InterScience Publishes, Inc., pp. 201-266, (1951).
Hanaki and Kamide, "Manometric Study of the Copper-Catalyzed Oxidation of Cysteine ," Chem. Pharm. Bull., 19(5):1006-1010, (1971).
Hardy et al., "Formulation, Stability, and Administration of Parenteral Nutrition With New Lipid Emulsions," Nutrition in Clinical Practice, 24(5):616-625, (2009).
Hardy et al., "P.83: Stability of aqueous cysteine solutions for TPN [Abstract]," Clinical Nutrition, 12(Suppl 2):61, (1993).
Harman et al., "Free Radical Metabolites of L-Cysteine Oxidation," The Journal of Biological Chemistry, 259(9):5606-5611, (1984). [Retrieved from the Internet Feb. 6, 2017: <URL: http://www.jbc.org/content/259/9/5606.full.pdf>].
Health Care Provider Letter from Exela Pharma Sciences, "Risk of Potential Aluminum Toxicity with Use of Potassium Acetate 40 meq/20 ml Injection Particularly n Neonatal Patients and Patients with Renal Impairment," 3 pages, (2017).
Healthcare Professional Letter from Baxter Healthcare Corporation, "Temporary importation of intravenous drug products to address drug shortages," 8 pages, (2017), retrieved from Exhibit 1087, Petition for Post Grant Review of U.S. Pat. No. 10,583,155, *Eton Pharmaceuticals, Inc. v. Exela Pharma Sciences, LLC*, PGR2020-00068, (PTAB Jun. 8, 2020).
Heird et al., "Pediatric Parenteral Amino Acid Mixture in Low Birth Weight Infants," Pediatrics, 81(1):41-50, (1988). [Retrieved from the Internet Dec. 8, 2017: <URL: http://pediatrics.aappublications.org/content/81/1/41>].
Hellström et al., "Sa1863. L-Cysteine Slow-Release Capsule Formulation in Prevention of Gastric Carcinogenesis Associated With Atrophic Gastritis," AGA Abstracts, 146(5, Suppl 1):S-315, (2014).
Helms et al., "Cysteine supplementation results in normalization of plasma taurine concentrations in children receiving home parenteral nutrition," J Pediatr, 134(3):358-361, (1999).

(56) References Cited

OTHER PUBLICATIONS

Hernández-Sánchez et al., "Aluminium in parenteral nutrition: a systematic review," European Journal of Clinical Nutrition, 67(3):230-238, (2013).
Heyman et al., "Aluminum Does Not Accumulate in Teenagers and Adults on Prolonged Parenteral Nutrition Containing Free Amino Acids," Journal of Parenteral and Enteral Nutrition, 10(1):86-87, (1986).
Hintz et al., "Aluminum Exposure From Pediatric Parenteral Nutrition: Meeting the New FDA Regulation," JPEN J Parenter Enteral Nutr, 32:242-246, (2008).
Ho et al., "Trend of Nutritional Support in Preterm Infants," Pediatrics and Neonatology, 57(5):365-370, (2016).
Hu et al., "Efficacy and safety of acetylcysteine in "non-acetaminophen" acute liver failure: A meta-analysis of prospective clinical trials," Clin Res Hepatol Gastroenterol, 39(5):594-599, (2015).
Hulst, Jessie, "Principles of feeding the preterm infant," 36th ESPEN Congress, Geneva, 44 pages, (2014).
Huston et al., "Calcium Chloride in Neonatal Parenteral Nutrition Solutions with and without Added Cysteine: Compatibility Studies Using Laser and Micro-Flow Imaging Methodology," PLoS ONE, 10(8):e0136894, (2015).
Huston et al., "Calcium chloride in neonatal parenteral nutrition: A 15 year experience," Journal of Neonatal-Perinatal Medicine, 10(1):33-38, (2017).
Huston et al., "Calcium Chloride in Neonatal Parenteral Nutrition: Compatibility Studies Using Laser Methodology," PLoS ONE, 9(9):e106825, (2014).
Ishii et al., "A case of drug-induced ductopenia resulting in fatal biliary cirrhosis," Liver, 13(4):227-231, (1993).
Ishii et al., "Cystathionine γ-Lyase-deficient Mice Require Dietary Cysteine to Protect against Acute Lethal Myopathy and Oxidative Injury," The Journal of Biological Chemistry, 285(34):26358-26368, (2010).
Jadhav et al., "Parenteral Amino Acid and Metabolic Acidosis in Premature Infants," JPEN J Parenter Enteral Nutr., 31(4):278-283, (2007).
Jalilehvand et al., "Lead(II) Complex Formulation with L-Cysteine in Aqueous Solution," Inorganic Chemistry, 54:2160-2170, (2015).
Janáky et al., "Mechanisms of L-Cysteine Neurotoxicity," Neurochemical Research, 25(9/10):1397-1405 (2000).
Ji et al., "Excessive L-cysteine induces vacuole-like cell death by activating endoplasmic reticulum stress and mitogen-activated protein kinase signaling in intestinal porcine epithelial cells," Amino Acids, 48(1):149-156, (2015).
John et al., "Total parenteral nutrition usage trends in the United States," Journal of Critical Care, 40:312-313, (2017).
Kartal et al., "Compatibility of chewing gum excipients with the amino acid L-cysteine and stability of the active substance in directly compressed chewing gum formulation," Journal of Pharmacy and Pharmacology, 60(9):1131-1138, (2008).
Kartal et al., "Formulation and in-vivo evaluation of L-cysteine chewing gums for binding carcinogenic acetaldehyde in the saliva during smoking," Journal of Pharmacy and Pharmacology, 59(10):1353-1358, (2007).
Kartal-Hodzic, Alma, "Formulation studies for eliminating saliva carcinogenic acetaldehyde with L-cysteine containing chewing gum," (Academic Dissertation), Division of Biopharmaceutics and Pharmacokinetics, University of Helsinki, Finland, 60 pages, (2012).
Kasraian et al., "Developing an Injectable Formula Containing an Oxygen-Sensitive Drug: A Case Study of Danofloxacin Injectable," Pharmaceutical Development and Technology, 4(4):475-480, (1999).
Klein et al., "Hypocalcemia Complicating Deferoxamine Therapy in an Infant with Parenteral Nutrition-Associated Aluminum Overload: Evidence for a Role of Aluminum in the Bone Disease of Infants," Journal of Pediatric Gastroenterology and Nutrition, 9(3):400-403, (1989). [Retrieved from the Internet Jun. 5, 2018: <URL: https://journals.lww.com/jpgn/Abstract/1989/10000/Hypocalcemia_Complicating_Deferoxamine_Therapy_in.24.aspx>].

Klein, Catherine J., "Nutrient Requirements for Preterm Infant Formulas," The Journal of Nutrition, 132(6 Suppl 1):1395S-1577S, (2002). [Retrieved from the Internet Dec. 6, 2017: <URL: http://jn.nutrition.org>].
Kolaric et al., "Solutions Preparing for Total Parenteral Nutrition for Children," Proceedings of the 7th WSEAS International Conference on Mathematics & Computers in Biology & Chemistry, Cavtat, Croatia, 6 pages, (2006).
Koletzko et al., "Guidelines on Paediatric Parenteral Nutrition: 3. Amino Acids," J. Pediatr. Gastroenterol. Nutr., 41 (Suppl. 2):S12-S18, (2005).
Komura et al., "Increased Incidence of Cholestasis during Total Parenteral Nutrition in Children," The Kurume Medical Journal, 40(1):7-11, (1993).
Koo et al., "Aluminum in Parenteral Nutrition Solution—Sources and Possible Alternatives," Journal of Parenteral and Enteral Nutrition, 10(6):591-595, (1986).
Koo et al., "Response to aluminum in parenteral nutrition during infancy," The Journal of Pediatrics, 109(5):877-883, (1986).
Laine et al., "Cysteine usage increases the need for acetate in neonates who receive total parenteral nutrition," The American Journal of Clinical Nutrition, 54(3):565-567, (1991). [Retrieved from the Internet Apr. 14, 2015: <URL: https://academic.oup.com/ajcn/article-abstract/54/3/565/4694399>].
Langille, Stephen E., "Particulate Matter in Injectable Drug Products," PDA Journal of Pharmaceutical Science and Technology, 67(3):186-200, (2013).
Lapillonne et al., "Quality of newborn care: adherence to guidelines for parenteral nutrition in preterm infants in four European countries," BMJ Open, 3(9):E003478, 8 pages, (2013). [Retrieved from the Internet Jun. 6, 2018: <URL: https://bmjopen.bmj.com/content/3/9/e003478>].
Larchet et al., "Aluminium Loading in Children Receiving Long-term Parenteral Nutrition," Clinical Nutrition, 9(2):79-83, (1990).
Lee et al., "AASLD Position Paper: The Management of Acute Liver Failure: Update 2011," Hepatology, 1-22 and Corrections, (2011).
Lee et al., "Intravenous N-Acetylcysteine Improves Transplant Free Survival in Early Stage Non-Acetaminophen Acute Liver Failure," Gastroenterology, 137(3):856-864, (2009).
Lee et al., "Introduction to the Revised American Association for the Study of Liver Diseases Position Paper on Acute Liver Failure 2011," Hepatology, 55(3):965-967, (2012).
Leung et al., "Consequences of excess iodine," Nat Rev Endocrinol., 10(3):136-142, (2014).
Leyden et al., "Stabilization of Solutions of Cysteine and its Derivatives," Can. J. Biochem., 45(4):611-614, (1967). [Retrieved from the Internet Nov. 12, 2014: <URL: https://www.nrcresearchpress.com/doi/pdf/10.1139/o67-071>].
Li et al., "Acute and sub-chronic toxicity of glucose-cysteine Maillard reaction products in Sprague-Dawley rats," Food and Chemical Toxicology, 80:271-276, (2015).
Lima-Rogel et al., "Aluminum Contamination in Parenteral Nutrition Admixtures for Low-Birth-Weight Preterm Infants in Mexico," Journal of Parenteral and Enteral Nutrition, 40(7):1014-1020, (2016).
Look et al., "Is the Increase in Serum Cystathionine Levels in Patients with Liver Cirrhosis a Consequence of Impaired Homocysteine Transsulfuration at the Level of γ-Cystathionase?," Scand J Gastroenterol, 35(8):866-872, (2000). [Retrieved from the Internet Oct. 25, 2014: <URL: https://www.tandfonline.com/doi/abs/10.1080/003655200750023255>].
Luo et al., "Kinetics and Mechanism of the Reaction of Cysteine and Hydrogen Peroxide in Aqueous Solution," Journal of Pharmaceutical Sciences, 94(2):304-316, (2005).
Mackay et al., "Physical Compatibility of Sodium Glycerophosphate and Calcium Gluconate in Pediatric Parenteral Nutrition Solutions," JPEN J Parenter Enteral Nutr, 39(6):725-728, (2015, Epub. 2014). [Retrieved from the Internet Apr. 6, 2014: <URL: http://pen.sagepub.com/content/early/2014/03/31/0148607114528982>].
Mackay et al., "The Solubility of Calcium and Phosphate in Two Specialty Amino Acid Solutions," Journal of Parenteral and Enteral

(56) References Cited

OTHER PUBLICATIONS

Nutrition, 20(1):63-66, (1996). [Retrieved from the Internet Apr. 17, 2015: <URL: https://onlinelibrary.wiley.com/doi/epdf/10.1177/014860719602000163>].

Maget, Henri J.R., "Use of an Oxygen Extractor to Minimize Oxidation of Compounded Preparations," International Journal of Pharmaceutical Compounding, 3(6):493-495, (1999).

Malloy et al., "Cyst(e)ine measurements during total parenteral nutrition," The American Journal of Clinical Nutrition, 37(2):188-191, (1983). [Retrieved from the Internet Apr. 14, 2015: <URL: https://academic.oup.com/ajcn/article-abstract/37/2/188/4690722>].

Malloy et al., "Cysteine Supplementation During Total Parenteral Nutrition (TPN) [Abstract]," Clinical Nutrition, 1 (Suppl.):49, (1982).

Malloy et al., "Cysteine Supplementation of Total Parenteral Nutrition: the Effect in Beagle Pups," Pediatric Research, 18(8):747-751, (1984).

Malloy et al., "Total Parenteral Nutrition in Sick Preterm Infants: Effects of Cysteine Supplementation with Nitrogen Intakes of 240 and 400 mg/kg/day," Journal of Pediatric Gastroenterology and Nutrition, 3(2):239-244, (1984).

Manz, Friedrich, "L-Cysteine in metabolic acidosis of low-birth-weight infants," Am J Clin Nutr, 57(3):455-456, (1993). [Retrieved from the Internet Apr. 16, 2015: <URL: https://academic.oup.com/ajcn/article-abstract/57/3/455/4715721>].

Mattox et al., "Chapter 142: Parenteral Nutrition," Pharmacotherapy: A Pathophysiologic Approach, 10e, McGraw Hill, Ed. Joseph T. DiPiro et al., 38 pages, (2016). [Retrieved from the Internet Dec. 5, 2017: <URL: https://accesspharmacy.mhmedical.com/content.aspx?bookid=1861&sectionid=146076679>].

Mccarthy et al., "Standardised versus individualized Parenteral Nutrition," Irish Medical Journal, 109(4):10 pages, (2016). [Retrieved from the Internet Jun. 6, 2018: <URL: http://imj.ie/standardised-versus-individualised-parenteral-nutrition-further-food-for-thought/>].

Mcclave et al., "Guidelines for the Provision and Assessment of Nutrition Support Therapy in the Adult Critically Ill Patient: Society of Critical Care Medicine (SCCM) and American Society for Parenteral and Enteral Nutrition (A.S.P.E.N.)," Journal of Parenteral and Enteral Nutrition, 40(2):159-211, (2016).

Mchalsky et al., "Reduction of Aluminum Levels in Dialysis Fluids Through the Development and Use of Accurate and Sensitive Analytical Methodology," Journal of Parenteral Science & Technology, 41(2):67-75, (1987).

Memorandum in Support of Plaintiff's Motion for Ex Parte Temporary Restraining Order and Preliminary Injunction, *Exela Pharma Sciences, LLC v. Sandoz, Inc.*, No. 1:19-cv-318, (W.D.N.C., Nov. 6, 2019).

Metabolic Processes in the Foetus and Newborn Infant, Nutricia Symposium, Ed. J. H. P. Jonxis et al., H. E. Stenfert Kroese N.V., 317 pages, (1971).

Mihatsch et al., "ESPGHAN/ESPEN/ESPR/CSPEN guidelines on pediatric parenteral nutrition: Calcium, phosphorus and magnesium," Clinical Nutrition, 37:2360-2365, (2018).

Miller et al., "Decreased Cysteine and Proline Synthesis in Parenterally Fed, Premature Infants," Journal of Pediatric Surgery, 30(7):953-958, (1995).

Miller, Sarah J., "Parenteral Nutrition," U.S. Pharmacist, 7(HS10-HS20):31 pages, (2006). [Retrieved from the Internet Sep. 26, 2018: <URL: https://www.uspharmacist.com/article/parenteral-nutrition>].

Mirtallo, Jay M., "Aluminum Contamination of Parenteral Nutrition Fluids," Journal of Parenteral and Enteral Nutrition, 34(3):346-347, (2010).

Mirtallo et al., "Safe Practices for Parenteral Nutrition," Journal of Parenteral and Enteral Nutrition, 28(6):S39-S70, (2004). [Retrieved from the Internet Jan. 23, 2014: <URL: https://journals.sagepub.com/doi/abs/10.1177/0148607104028006s39>].

Moreno et al., "Aluminium in the neonate related to parenteral nutrition," Acta Paediatr, 83(1):25-29, (1994).

Moreno Villares et al., "Current use of parenteral nutrition in a pediatric hospital. Comparison to the practise 8 years ago," Nutr. Hosp., 20(1):46-51, (2005).

Mühlebach, Stefan, "Parenteral Nutrition: The Roie of the Pharmacist in the Era of 3-chamber Bags," 27th ESPEN Congress, Brussels, 49 pages, (2005).

Mundi et al., "Prevaience of Home Parenteral and Enteral Nutrition in the United States [Abstract]," Nutr Clin Pract., 32(6):799-805, (2017). [Retrieved from the Internet Jun. 6, 2018: <URL: http://journals.sagepub.com/doi/pdf/10.1177/0884533617718472>].

Murphy et al., "Annual Summary of Vital Statistics: 2013-2014," Pediatrics, 139(6):e20163239, (2017). [Retrieved from the Internet Jun. 6, 2018: <URL: http://pediatrics.aapublications.org/content/139/6/e20163239>].

Nguyen et al., "Effect of increasing Glutathione With Cysteine and Glycine Supplementation on Mitochondrial Fuel Oxidation, Insulin Sensitivity, and Body Composition in Older HIV-Infected Patients," J Clin Endocrinol Metab,, 99(1):169-177, (2014). [Retrieved from the Internet Dec. 12, 2017: <URL: https://academic.oup.com/jcem/article-abstract/99/1/169/2836223>].

Nicolet, Ben H., "Biochemistry by Analogy: the Sulfur of Cystine,"Journal of the Washington Academy of Sciences, 28(3):84-93, (1938).

Niermeyer et al., "Optimized calcium/phosphorus solubility in a parenteral nutrition solution containing dicarboxylic amino acids and cysteine," Journal of the American College of Nutrition, 5(5):459-466, (1986). [Retrieved from the Internet Apr. 21, 2015: <URL: https://www.tandfonline.com/doi/pdf/10.1080/07315724.1986.10720149>].

Nishiyama et al., "Transient Hypothyroidism or Persistent Hyperthyrotropinemia in Neonates Born to Mothers with Excessive Iodine Intake," Thyroid, 14(2):1077-1083, (2004).

Non-Clinical Review(s), Application No. 210906Orig1s000, Center for Drug Evaluation and Research, 25 pages, (2017).

Ogawa et al., "Comparisons of Aluminum and Silica Elution from Various Glass Vials," Chemical and Pharmaceutical Bulletin, 64:150-160, (2016).

Okabe, Len, "Studies on the Solubility of Cystine Under Various Conditions, and on a New Method of Cystine Preparation," The Journal of Biochemistry, VIII(2):441-457, (1927).

Olney et al., "Brain Damage in Infant Mice following Oral Intake of Glutamate, Aspartate or Cysteine," Nature, 227(5258):609-611, (1970).

O'neal et al., "Compliance with safe practices for preparing parenteral nutrition formulations," Am J Health Syst Pharm, 59(3):264-269, (2002).

Parikh et al., "Physical compatibility of neonatal total parenteral nutrient admixtures containing organic calcium and inorganic phosphate salts," Am J Health Syst Pharm, 62(11):1177-1183, (2005).

Patanwala et al., "Antiemetic Therapy for Nausea and Vomiting in the Emergency Department," The Journal of Emergency Medicine, 39(3):330-336, (2010).

Patel et al., "Stability Considerations for Biopharmaceuticals: Overview of Protein and Peptide Degradation Pathways," BioProcess International, 23 pages, (2011). [Retrieved from the Internet May 11, 2020: <URL: https://bioprocessintl.com/manufacturing/formulation/biopharmaceutical-product-stability-considerations-part-1/>].

Patel et al., "Total parenteral nutrition for premature infants: practice aspects," Journal of Nature and Science (JNSCI), 3(1):e301, 6 pages, (2017).

Patent Owner's Preliminary Response, *Eton Pharmaceuticals, Inc. v. Exela Pharma Sciences, LLC*, PGR2020-00064, U.S. Pat. No. 10,478,453, (Aug. 28, 2020).

Patent Owner's Preliminary Response, *Eton Pharmaceuticals, Inc. v. Exela Pharma Sciences, LLC*, PGR2020-00068, U.S. Pat. No. 10,583,155, (Sep. 18, 2020).

Patent Owner's Preliminary Response, *Eton Pharmaceuticals, Inc. v. Exela Pharma Sciences, LLC*, PGR2020-00086, U.S. Pat. No. 10,653,719, (Jan. 27, 2021).

Patent Owner's Sur-Reply to Petitioner's Reply to Patent Owner's Preliminary Response, *Eton Pharmaceuticals, Inc. v. Exela Pharma Sciences, LLC*, PGR2020-00064, U.S. Pat. No. 10,478,453, (Oct. 5, 2020).

(56) References Cited

OTHER PUBLICATIONS

Patent Owner's Sur-Reply to Petitioner's Reply to Patent Owner's Preliminary Response, *Eton Pharmaceuticals, Inc. v. Exela Pharma Sciences, LLC*, PGR2020-00068, U.S. Pat. No. 10,583,155, (Oct. 26, 2020).
Patent Owner's Sur-Reply to Petitioner's Reply to Patent Owner's Preliminary Response, *Eton Pharmaceuticals, Inc. v. Exela Pharma Sciences, LLC*, PGR2020-00086, U.S. Pat. No. 10,653,719, (Feb. 25, 2021).
Patrick, A.D., "The Degradative Metabolism of L-Cysteine and L-Cystine in vitro by Liver in Cystinosis," Biochem J., 83:248-256, (1962).
Patt et al., "Cysteine Protection against X Irradiation," Science, 110(2852):213-214, (1949).
Paulikova et al., "Iodine toxicity in ruminants," Vet. Med.—Czech, 47(12):343-350, (2002).
Peri, Prasad, "Quality by Design (QbD) Approaches for Orally Inhaled and Nasal Drug Products (OINDPs) in the USA," ONDQA, OPS, CDER, DD Europe, 31 pages, (2007).
Pertkiewicz et al., "Basics in clinical nutrition: Stability of parenteral nutrition admixtures," e-SPEN, the European e-Journal of Clinical Nutrition and Metabolism, 4(3):e117-e119, (2009).
Petition for Post Grant Review of U.S. Pat. No. 10,478,453, *Eton Pharmaceuticals, Inc. v. Exela Pharma Sciences, LLC*, PGR2020-00064, (PTAB May 19, 2020).
Petition for Post Grant Review of U.S. Pat. No. 10,583,155, *Eton Pharmaceuticals, Inc. v. Exela Pharma Sciences, LLC*, PGR2020-00068, (PTAB Jun. 8, 2020).
Petition for Post Grant Review of U.S. Pat. No. 10,653,719, *Eton Pharmaceuticals, Inc. v. Exela Pharma Sciences, LLC*, PGR2020-00086, (PTAB Sep. 21, 2020).
Petitioner's Reply to Patent Owner's Preliminary Response, *Eton Pharmaceuticals, Inc. v. Exela Pharma Sciences, LLC*, PGR2020-00064, U.S. Pat. No. 10,478,453, (Sep. 28, 2020).
Petitioner's Reply to Patent Owner's Preliminary Response, *Eton Pharmaceuticals, Inc. v. Exela Pharma Sciences, LLC*, PGR2020-00068, U.S. Pat. No. 10,583,155, (Oct. 19, 2020).
Petitioner's Reply to Patent Owner's Preliminary Response, *Eton Pharmaceuticals, Inc. v. Exela Pharma Sciences, LLC*, PGR2020-00086, U.S. Pat. No. 10,653,719, (Feb. 17, 2021).
Pilaniya et al., "Recent trends in the impurity profile of pharmaceuticals," J Adv Pharm Technol Res., 1(3):302-310, (2010).
Plogsted et al., "Parenteral Nutrition L-Cysteine Product Shortage Considerations," Nutrition in Clinical Practice, 30(4):579-580, (2015).
Poole et al., "Aluminum Exposure From Pediatric Parenteral Nutrition: Meeting the New FDA Regulation," Journal of Parenteral and Enteral Nutrition, 32(3):242-246, (2008).
Poole et al., "Aluminum Exposure in Neonatal Patients Using the Least Contaminated Parenteral Nutrition Solution Products," Nutrients, 12(4):1566-1574, (2012).
Poole et al., "Aluminum in Pediatric Parenteral Nutrition Products: Measured Versus Labeled Content," J. Pediatr. Pharmacol. Ther., 16(2):92-97, (2011).
Pyati et al., "Absorption of iodine in the neonate following topical use of povidone iodine," The Journal of Pediatrics, 91(5):825-828, (1977).
Rabbani et al., "Glycation research in amino acids: a place to call home," Amino Acids, 42:1087-1096, (2012). [Retrieved from the Internet May 10, 2016: <URL: https://www.researchgate.net/publication/47567399>].
Rabinow and Roseman, "Plastic Packaging Materials," Remington: The Science and Practice of Pharmacy, 21st ed., Ed. David B. Troy, Baltimore: Lippincott Williams & Wilkins, pp. 1047-1057, (2006).
Rabinow et al., "Aluminum in Parenteral Products: Analysis, Reduction, and Implications for Pediatric TPN," Journal of Parenteral Science & Technology, 43(3):132-139, (1989).
Rassin, David Keith, "Essential and Non-essential Amino Acids in Neonatal Nutrition," Protein Metabolism During Infancy, 33:183-195, (1994).

Reichert et al., "Metal Residue: How Much is Too Much?" Pharma Manufacturing, 12 pages, (2013).
Remington's Pharmaceutical Sciences, 16th edition, Ed. A. Osol, Mack Publishing Co., Easton, PA, (1980).
Reply in Support of Plaintiff's Motion for Preliminary Injunction, *Exela Pharma Sciences, LLC v. Sandoz, Inc.*, No. 1:19-cv-318-MR, W.D.N.C., Dec. 13, 2019.
Response in Opposition to Plaintiff's Motion for Preliminary injunction, *Exela Pharma Sciences, LLC v. Sandoz, Inc.*, No. 1:19-cv-318-MR, (W.D.N.C., Dec. 6, 2019).
Riedijk et al., "Cyst(e)ine Requirements in Enterally Fed Very Low Birth Weight Preterm Infants," Pediatrics, 121(3):e561-e567, (2008). [Retrieved from the Internet Apr. 10, 2015: <URL: http://pediatrics.aappublications.org/content/121/3/e561.full.html>].
Reidijk et al., "Cysteine: a conditionally essential amino acid in low-birth-weight preterm infants?," The American Journal of Clinical Nutrition, 86(4):1120-1125, (2007). [Retrieved from the Internet Apr. 13, 2015: <URL: https://academic.oup.com/ajcn/article/86/4/1120>].
Riedijk, M.A., "Neonatal Sulfur Amino Acid Metabolism," (Thesis), Erasmus Universiteit Rotterdam, the Netherlands, 176 pages, (2008).
Rignall, Andy, "ICHQ1A(R2) Stability Testing of New Drug Substance and Product and ICHQ1C Stability Testing of New Dosage Forms," ICH Quality: An Implementation Guide, Ed. Andrew Teasdale et al., Hoboken, NJ: John Wiley & Sons, Inc., pp. 3-14, 26-31, and 37-38, (2018).
Ripps et al., "Review: Taurine: A "very essential" amino acid," Molecular Vision, 18:2673-2686, (2012).
Rokushika et al., "Radiolysis of Cystine in Aqueous Solution by Gamma Irradiation," Journal of Radiation Research, 7(2):47-57, (1966).
Rubaltelli et al., "Parenteral Nutrition of the Newborn," Feeding the Sick Infant, Nestlé Nutrition Workshop Séries, 11:241-255, (1987).
Rudman et al., "Hypotyrosinemia, Hypocystinemia, and Failure to Retain Nitrogen During Total Parenteral Nutrition of Cirrhotic Patients," Gastroenterology, 81:1025-1035, (1981).
Salaspuro et al., "Eliminating Carcinogenic Acetaldehyde By Cysteine From Saliva During Smoking," Cancer Epidemiol Biomarkers Prev, 15(1):146-149, (2006). [Retrieved from the Internet May 26, 2016: <URL: http://cebp.aacrjournals.org/content/15/1/146>].
Salaspuro et al., "Removal of Acetaldehyde 2from Saliva by a Slow-Release Buccal Tablet of L-Cysteine," Int. J. Cancer, 97(3):361-364, (2002).
Sandilands et al., "Adverse reactions associated with acetylcysteine," Clinical Toxicology, 47(2):81-88, (2009). [Retrieved from the Internet Jul. 10, 2014: <URL: https://www.tandfonline.com/doi/full/10.1080/15563650802665587>].
Sawamoto et al., "Development of Sperm Granulomas in the Epididymides of L-Cysteine-Treated Rats," Toxicologic Pathology, 31(3):281-289, (2003).
Sawamoto et al., "Four-Week Intravenous Repeated Dose Toxicity Study of L-Cysteine in Male Rats," The Journal of Toxicological Sciences, 28(2):95-107, (2003).
Sawamoto et al., "L-Cysteine-induced brain damage in adult rats," Experimental and Toxicologic Pathology, 56(1-2):45-52, (2004).
Schanler et al., "Parenteral nutrition in premature infants," UptoDate, 23 pages, (2014).
Schmidt et al., "Cost Containment Using Cysteine HCl Acidification to Increase Calcium/Phosphate Solubility in Hyperalimentation Solutions," Journal of Parenteral and Enteral Nutrition, 10(2):203-207, (1986). [Retrieved from the Internet Apr. 2, 2015: <URL: https://onlinelibrary.wiley.com/doi/10.1177/0148607186010002203>].
Schulpis et al., "L-Cysteine supplementation protects the erythrocyte glucose-6-phosphate dehydrogenase activity from reduction induced by forced training," Clinical Biochemistry, 39(10):1002-1006, (2006).
Schuringa et al., "The Reaction of Combined Cystine of Wool with Sodium Bisulfite," Textile Research Journal, 21:281-285, (1951).
Sears, Margaret E., "Chelation: Harnessing and Enhancing Heavy Metal Detoxification—A Review," The Scientific World Journal, 2013(219840): 13 pages, (2013).

(56) References Cited

OTHER PUBLICATIONS

Sedman et al., "Evidence of Aluminum Loading in Infants Receiving Intravenous Therapy," The New England Journal of Medicine, 312(21):1337-1343, (1985).
Segal et al., "Delineation of Cystine and Cysteine Transport Systems in Rat Kidney Cortex by Developmental Patterns," Proc Natl Acad Sci USA, 63(3):926-933, (1969).
Shelton et al., "Plasma Amino Acid Concentrations in 108 Children Receiving a Pediatric Amino Acid Formulation as Part of Parenteral Nutrition," J Pediatr Pharmacol Ther, 15(2):110-118, (2010).
Shew et al., "Assessment of cysteine synthesis in very low-birth weight neonates using a [13C6]glucose tracer," Journal of Pediatric Surgery, 40(1):52-56, (2005).
Shew et al., "Improved Protein Metabolism in Neonates Receiving Parenteral Cysteine Supplementation," Pediatric Research, 45(290A), 3 pages, (1999). [Retrieved from the Internet Apr. 18, 2018: <URL: http://www.nature.com/articles/pr19991842>].
Shulman et al., "Parenteral Nutrition in Infants and Children," Journal of Pediatric Gastroenterology and Nutrition, 36(5):587-607, (2003).
Shulman et al., "Reply to F Manz," Am J Clin Nutr, 57(3):456, (1993). [Retrieved from the Internet Apr. 16, 2015: <URL: https://academic.oup.com/ajcn/article-abstract/57/3/456/4715642>].
Sidhu et al., "L-Cysteine and Sodium Hydrosulphide Inhibit Spontaneous Contractility in Isolated Pregnant Rat Uterine Strips in vitro," Pharmacology & Toxicology, 88(4):198-203, (2001).
Simmer et al., "Standardised Parenteral Nutrition," Nutrients, 5(4):1058-1070, (2013).
Singer et al., "ESPEN Guidelines on Parenteral Nutrition: Intensive care," Clinical Nutrition, 28(4):387-400, (2009).
Singh et al., "Physical compatibility of neonatal total parenteral nutrition admixtures containing organic calcium and inorganic phosphate salts in a simulated infusion at 37° C.," Pediatr Crit Care Med, 10(2):213-216, (2009).
Smith et al., "Effect of additive selection on calculated aluminum content of parenteral nutrient solutions," Am. J. Health Syst. Pharm., 64(7):730-739, (2007).
Soghier et al., "Cysteine, cystine or N-acetylcysteine supplementation in parenterally fed neonates (Updates)," Cochraine Database of Systematic Reviews, 4(CD004869):13 pages, (2009). [Retrieved from the Internet Apr. 14, 2015: <URL: https://www.nichd.nih.gov/cochrane_data/brionl_07/brionl_07.html>].
Soghier et al., "Cysteine, cystine or N-acetylcysteine supplementation in parenterally fed neonates," Cochraine Database of Systematic Reviews, 4(CD004869):40 pages, (2006).
Standard Methods for the Examination of Water and Sewage, 2nd ed., Boston: American Public Health Association, pp. 59-62, (1915).
Staun et al., "ESPEN Guidelines on Parenteral Nutrition: Home Parenterai Nutrition (HPN) in adult patients," Clinical Nutrition, 28(4):467-479, (2009).
Stawny et al., "Pharmaceutical Point of View on Parenteral Nutrition," Hindawi Publishing Corporation, 2013(415310), 9 pages, (2013).
Stipanuk et al., "Mammalian Cysteine Metabolism: New Insights into Regulation of Cysteine Metabolism," The Journal of Nutrition, 136(6 Suppl):1652S-1659S, (2006). [Retrieved from the Internet Feb. 7, 2017: <URL: http://jn.nutrition.org>].
Storm et al., "Cysteine Supplementation Normalizes Plasma Taurine Concentrations in Low Birth Weight Premature Infants Requiring Parenteral Nutrition Support [Abstract]," Nutrition Week 2003 Abstracts, 27(1):S4-S5, (2003).
Sturman et al., "Absence of Cystathionase in Human Fetal Liver: Is Cystine Essential?," Science, 169(3940):74-76, (1970). [Retrieved from the Internet Dec. 5, 2017: <URL: https://science.sciencemag.org/content/169/3940/74/tab-pdf>].
Sullivan et al., "The Effect of Pyruvic Acid on the Estimation of Cystine and Cysteine," J Biol. Chem., 122:11-17, (1937).
Szwergold et al., "Transglycation—A Potential New Mechanism for Deglycation of Schiff's Bases," Ann. N.Y. Acad. Sci., 1043:845-864, (2005).

Te Braake et al., "High-Dose Cysteine Administration Does Not increase Synthesis of the Antioxidant Glutathione Preterm Infants," Pediatrics, 124(5):e978-e984, (2009). [Retrieved from the Internet May 29, 2015: <URL: http://pediatrics.aappublications.org/content/124/5/e978.full.html>].
Teasdale et al., "Impurities in New Drug Substances and New Drug Products," ICH Quality: An Implementation Guide, Eds. Andrew Teasale et al., Hoboken: John Wiley & Sons, Inc., pp. 167-198, (2018).
Télessy et al., "Kinetic stability of all-in-one parenteral nutrition admixtures in the presence of high dose Ca2+ additive under clinical application circumstances," Nutrition Journal, 11(32):5 pages, (2012).
The Merck Index: An Encyclopedia of Chemicals, Drugs, and Bioiogicals, Ed. Maryadele J. O'Neil et al., 14th ed., Whitehouse Station: Merck & Co., Inc, pp. 2782-2783, (2006).
Thibault, Maxime, "Possible Incompatibility between Amino Acids and Copper in Solutions for Pediatric Parenteral Nutrition," CJHP, 67(2):160-164, (2014).
Thomas, David L., "Recommended Pinnacle® Compounder Ingredient Mixing Sequence," LDT Health Solictions, Inc., 4 pages, (2012).
Thomovsky et al., "Parenteral Nutrition: Formulation, Monitoring, and Complications," Compend Contin Educ Vet., VetFolio, 29(2):88-102, (2007). [Retrieved from the Internet Sep. 27, 2018: <URL: http://www.vetfolio.com/nutrition/parenteral-nutrition-formulation-monitoring-and-complications>].
Thor et al., "Metabolic Activation and Hepatotoxicity," Archives of Biochemistry and Biophysics, 192(2):405-413, (1979).
Transcript of Telephone Conference, Exhibit 1083, *Eton Pharmaceuticals, Inc.* v. *Exela Pharma Sciences, LLC*, PGR2020-00064, U.S. Pat. No. 10,478,453, (Sep. 21, 2020).
Transcript of Telephone Conference, Eton Ex. 1124, *Eton Pharmaceuticals, Inc.* v. *Exela Pharma Sciences, LLC*, PGR2020-00086, U.S. Pat. No. 10,583,155, (Feb. 8, 2021).
Tribble et al., "Hypercysteinemia and delayed sulfur excretion in cirrhotics after oral cysteine loads," Am J Clin Nutr, 50:1401-1406, (1989).
Trissel et al., "Use of Cysteine Hydrochloride Injection to Increase the Solubility of Calcium and Phosphates in FreAmine III-Containing Parenteral Nutrition Solutions," International Journal of Pharmaceutical Compounding, 7(1):71-77, (2003).
Turco, Salvatore J., "Intravenous Admixtures," Remington: The Science and Practice, 21 ed., Philadelphia: Lippincott Williams & Wilkins, pp. 837-846, (2006).
USP 23/NF 18, The U.S. Pharmacopeial Convention, Inc., The National Formulary, pp. 1635-1637, 1650-1652, and 1813-1819, (1995).
USP 23/NF 27, The U.S. Pharmacopeial Convention, The National Formulary, pp. 1-12, (2009).
USP XXI, The United States Pharmacopeia, Twenty-First Revision, The U.S. Pharmacopeial Convention, Inc., pp. 19-20, 268-269, and 1375, (1985).
Van Goudoever et al., "Amino Acid Solutions for Premature Neonates During the First Week of Life: The Role of N-Acetyl-L-Cysteine and N-Acetyl-L-Tyrosine," Journal of Parenteral and Enteral Nutrition, 18(5):404-408, (1994). [Retrieved from the Internet Oct. 28, 2014: <URL: http://pen.sagepub.com/content/18/5/404>].
Van Goudoever et al., "ESPGHAN/ESPEN/ESPR/CSPEN guidelines on pediatric parenteral nutrion: Amino acids," Clinical Nutrition, 37:2315-2323, (2018).
Vendemiale et al., "Effects of Oral S-Adenosyl-L-Methionine on Hepatic Giutathione in Patients with Liver Disease," Scand J Gastroenterol, 24(4):407-415, (1989). [Retrieved from the Internet Sep. 7, 2013: <URL: https://www.tandfonline.com/doi/abs/10.3109/00365528909093067>].
Viña et al., "L-Cysteine and glutathione metabolism are impaired in premature infants due to cystathionase deficiency," Am J Clin Nutr, 61(5):1067-1069, (1995).
Vinton et al., "Taurine Concentrations in Plasma, Blood Cells, and Urine of Children Undergoing Long-Term Total Parenteral Nutrition," Pediatric Research, 21(4):399-403, (1987).
Warning Letter from U.S. Food and Drug Administration to Mr. Ian Reed, Pfizer, Hospira Inc, dated Feb. 14, 2017.

(56) References Cited

OTHER PUBLICATIONS

Warshawsky, Kathleen Young, "Intravenous Fat Emulsions in Clinical Practice," NCP, 7(4):187-196, (1992). [Retrieved from the Internet Mar. 18, 2015: <URL: https://onlinelibrary.wiley.com/doi/epdf/10.1177/0115426592007004187x>].

Waterman et al., "Stabilization of Pharmaceuticals to Oxidative Degradation," Pharmaceutical Development and Technology, 7(1):1-32, (2002).

Watrobska-Swietukowska et al., "Evaluation of physical stability of all in one parenterai admixtures for pediatric home care with high electrolytes concentrations," Nutr Hosp., 31(1):236-243, (2015).

Weinstein et al., "In Vivo Studies of Cysteine Metabolism: Use of D-cysteinesulfinate, a novel cysteinesulfinate decarboxylase inhibitor, to probe taurine and pyruvate synthesis," The Journal of Biological Chemistry, 263(32):16568-16579, (1988).

Whipple and Whipple, "Solubility of Oxygen in Sea Water," J. Am. Chem. Soc., 33:362-365, (1911).

Whiting et al., "Effect of Headspace Oxygen Concentration on Growth and Toxin Production by Proteolytic Strains of Clostridium botulinum," Journal of Food Protection, 55(1):23-27, (1992).

Whyte et al., "Safety and Effectiveness of Acetadote for Acetaminophen Toxicity," The Journal of Emergency Medicine, 39(5):607-611, (2010).

Wilhelm et al., "Aluminum balance in intensive care patients," J. Trace Elements Med. Biol., 14(4):223-227, (2001).

Williams et al., "Supplemental Iodide for Preterm Infants and Developmental Outcomes at 2 Years: An RCT," Pediatrics, 139(5):e20163703, 14 pages, (2017). [Retrieved from the Internet Dec. 12, 2018: <URL: http://pediatrics.aappublications.org/content/139/5/e20163703>].

Wlodek, Lidia, "The Reaction of Sulfhydryl Groups with Carbonyl Compounds," Acta Biochimica Polonica, 35(4):307-317, (1988).

Woolsey, Patricia B.E., "Cysteine, Sulfite, and Glutamate Toxicity: A Cause of ALS?," The Journal of Alternative and Complementary Medicine, 14(9):1159-1164, (2008).

Worthington et al., "When is Parenteral Nutrition Appropriate?," Journal of Parenteral and Enteral Nutrition, 41(3):324-377, (2017).

Yamaguchi et al., "Induction and Activation of Cysteine Oxidase of Rat Liver, II. The Measurement of Cysteine Metabolism in vivo and the Activation of in vivo Activity of Cysteine Oxidase," Biochimica et Biophysica Acta, 297(1):48-59, (1973).

Yaman, Alpaslan, "Engineering Considerations in Sterile Powder Processes," Sterile Pharmaceutical Products: Process Engineering Applications, Ed. Kenneth E. Avis, Buffalo Grove: Interpharm Press, Inc., pp. 269-304, (1995).

Yao et al., "Effect of glucose-cysteine adduct as a cysteine prodrug in rats," Amino Acids, 12(1):85-94, (1997).

Yao et al., "Protective effect of glucose-cysteine adduct on the in situ perfused rat liver," Amino Acids, 12(1):33-40, (1997).

Yarandi et al., "Amino acid composition in parenteral nutrition: what is the evidence?," Curr Opin Clin Nutr Metab Care, 14(1):75-82, (2011).

Ybarra, Joseph V., "Calcium and Phosphate Solubility in Neonatal Parenteral Nutrient Solutions Containing TrophAmine," Nutrition in Clinical Practice, 25(4):353-356, (2010).

Yesil et al., "Evaluation of the Children with Acute Acetaminophen Overdose and Intravenous N-Acetylcysteine Treatment," Pak J Med Sci., 34(3):590-594, (2018).

Yin et al., "L-Cysteine metabolism and its nutritional implications," Mol. Nutr. Food Res., 0:1-13, (2015).

Yu et al., "Understanding Pharmaceutical Quality by Design," The AAPS Journal, 16(4):771-783 (2014).

Zerangue et al., "Interaction of L-cysteine with a human excitatory amino acid transporter," Journal of Physiology, 493(2):419-423, (1996).

Zhang et al., "A Perspective on the Maillard Reaction and the Analysis of Protein Glycation by Mass Spectrometry: Probing the Pathogenesis of Chronic Disease," J Proteome Res., 8(2):754-769, (2009).

Zhu and Wang, "Formulation of protein- and peptide-based parenteral products," Pharmaceutical Dosage Forms: Parenteral Medications, vol. 1: Formulation and Packaging, 3rd ed., Eds. Sandeep Nema and John D. Ludwig, New York: Informa Healtchare, pp. 222-253, (2010).

Ziegler, Ekhard E., "Parenteral Nutrition," Iowa Neonatology Handbook: Feeding, (2006).

Zlotkin et al., "Cysteine supplementation to cysteine-free intravenous feeding regimens in newborn infants," The American Journal of Clinical Nutrition, 34(5):914-923, (1981). [Retrieved from the Internet Apr. 14, 2015: <URL: https://academic.oup.com/ajcn/article-abstract/34/5/914/4431066>].

Zlotkin et al., "The Development of Cystathionase Activity During the First Year of Life," Pediatr. Res., 16(1):65-68, (1982).

U.S. Appl. No. 16/746,028, filed Jan. 17, 2020, U.S. Pat. No. 10,933,089, Issued.

U.S. Appl. No. 16/665,702, filed Oct. 28, 2019, U.S. Pat. No. 10,583,155, Issued.

U.S. Appl. No. 16/248,460, filed Jan. 15, 2019, U.S. Pat. No. 10,478,453, Issued.

Memorandum Opinion, *Exela Pharma Sciences, v. Eton Pharmaceuticals, Inc.*, No. 1:20-cv-365 (MN), (U.S. Distr. Del. Aug. 8, 2022).

\* cited by examiner

STABLE, HIGHLY PURE L-CYSTEINE COMPOSITIONS FOR INJECTION AND METHODS OF USE

CROSS-REFERENCE TO RELATED APPLICATION(S)

This application is a continuation of U.S. application Ser. No. 16/746,028, filed Jan. 17, 2020, which is a continuation of U.S. application Ser. No. 16/665,702, filed Oct. 28, 2019, now U.S. Pat. No. 10,583,155, issued on Mar. 10, 2020, which is a continuation of U.S. application Ser. No. 16/248,460, filed Jan. 15, 2019, now U.S. Pat. No. 10,478,453, issued on Nov. 19, 2019, each of which are incorporated herein in their entirety by reference.

TECHNICAL FIELD

The subject matter described herein relates generally to compositions for parenteral administration comprising L-cysteine that are stable and have desirable safety attributes for extended periods of time.

BACKGROUND

L-cysteine is a sulfur-containing amino acid that can be synthesized de novo from methionine and serine in adult humans. L-cysteine performs a variety of metabolic functions. For example, L-cysteine is involved in growth and protein synthesis and it is a precursor for glutathione, an important intracellular antioxidant.

L-cysteine is generally classified as a non-essential amino acid or "semi-essential" amino acid because it can be synthesized in small amounts by the human body. However, some adults can still benefit from L-cysteine supplementation. Further, L-cysteine has been classified as conditionally essential in some cases. For example, L-cysteine can be conditionally essential in preterm infants due to biochemical immaturity of the enzyme cystathionase that is involved in L-cysteine synthesis. Thus, there are a number of circumstances in which L-cysteine supplementation can be desirable.

The subject matter described herein addresses the shortcomings of the art by providing L-cysteine compositions that facilitate the desired supplementation but with an exceptional safety, purity and stability profile.

BRIEF SUMMARY

In certain aspects, the subject matter described herein is directed to a safe, stable L-cysteine composition for parenteral administration, comprising:

L-cysteine or a pharmaceutically acceptable salt thereof and/or hydrate thereof in an amount from about 10 mg/mL to about 100 mg/mL;

Aluminum (Al) in an amount from about 1.0 part per billion (ppb) to about 250 ppb;

L-cysteine in an amount from about 0.001 wt % to about 2.0 wt % relative to L-cysteine;

pyruvic acid in an amount from about 0.001 wt % to about 2.0 wt % relative to L-cysteine;

a pharmaceutically acceptable carrier, comprising water;

headspace $O_2$ that is from about 0.5% to 4.0% from the time of manufacture to about 1 month from manufacture when stored at room temperature;

dissolved oxygen present in the carrier in an amount from about 0.1 parts per million (ppm) to about 5 ppm from the time of manufacture to about 1 month from manufacture when stored at room temperature, wherein the composition is enclosed in a single-use container having a volume of from about 10 mL to about 100 mL.

In certain aspects, the subject matter described herein is directed to a safe, stable L-cysteine composition for parenteral administration, comprising:

L-cysteine or a pharmaceutically acceptable salt thereof and/or hydrate thereof in an amount from about 10 mg/mL to about 100 mg/mL;

Aluminum (Al) in an amount from about 1.0 parts per billion (ppb) to about 250 ppb;

L-cysteine in an amount from about 0.001 wt % to about 2.0 wt % relative to L-cysteine;

pyruvic acid in an amount from about 0.001 wt % to about 2.0 wt % relative to L-cysteine;

a pharmaceutically acceptable carrier, comprising water;

headspace $O_2$ that is from about 0.5% to 4.0% from the time of manufacture to about 1 month from manufacture when stored at room temperature;

dissolved oxygen present in the carrier in an amount from about 0.1 parts per million (ppm) to about 5 ppm from the time of manufacture to about 1 month from manufacture when stored at room temperature, optionally one or more metals selected from the group consisting of Lead from about 1.0 ppb to about 10 ppb, Nickel from about 5 ppb to about 40 ppb, Arsenic from about 0.1 ppb to 10 ppb, and Mercury from about 0.2 ppb to about 5.0 ppb;

wherein the composition is enclosed in a single-use container having a volume of from about 10 mL to about 100 mL.

In certain aspects, the subject matter described herein is directed to a safe, stable composition from about 100 mL to about 1000 mL for administration via a parenteral infusion within about 24 to about 48 hours of admixture, comprising a mixture of a composition of L-Cysteine described herein; and an amino acid composition that is essentially free of L-Cysteine comprising one or more amino acids selected from the group consisting of: leucine, isoleucine, lysine, valine, phenylalanine, histidine, threonine, methionine, tryptophan, alanine, arginine, glycine, proline, serine, and tyrosine.

In certain aspects, the subject matter described herein is directed to a method of reducing Aluminum administration from a total parenteral nutrition regimen comprising L-cysteine, the method comprising, mixing a composition comprising L-cysteine or a pharmaceutically acceptable salt thereof and/or hydrate thereof comprising:

Aluminum in an amount from about 1.0 parts per billion (ppb) to about 250 ppb;

L-cysteine in an amount from about 0.001 wt % to about 2.0 wt % relative to L-cysteine; and pyruvic acid in an amount from about 0.001 wt % to about 2.0 wt % relative to L-cysteine;

with a composition comprising one or more amino acids selected from the group consisting of: leucine, isoleucine, lysine, valine, phenylalanine, histidine, threonine, methionine, tryptophan, alanine, arginine, glycine, proline, serine, and tyrosine; and a pharmaceutically acceptable carrier, comprising water, to form a composition for infusion having a volume of about 100 mL to about 1000 mL, wherein the Aluminum provided in said parenteral nutrition regimen is from about 1-2 to about 4-5 micrograms/kg/day.

In certain aspects, the subject matter described herein is directed to methods of treating a subject having an adverse health condition that is responsive to L-cysteine administration, comprising:

diluting a stable L-cysteine composition as described herein with an intravenous fluid to prepare a diluted L-cysteine composition for infusion; and infusing the diluted L-cysteine composition for infusion to a subject to provide a therapeutically effective dose of L-cysteine or a pharmaceutically acceptable salt thereof and/or hydrate thereof to the subject in a therapeutically effective dosing regimen.

In certain aspects, the subject matter described herein are directed to methods of administering L-Cysteine together with a composition for parenteral nutrition, comprising:

diluting a stable L-cysteine composition for injection as described herein with a parenteral nutrition composition to form a mixture; and parenterally administering the mixture to a subject in need thereof in a therapeutically and/or nutritionally effective dose. In one aspect, the subject is a preterm infant or newborn to about 1 month of age. Some of these subjects may weigh from about 0.5 kilos to about 2.0 kilos. In another aspect, the subject is a pediatric patient that is of about 1 month to six months of age. Some of these subjects may weigh from about 0.2 kilos to about 20 kilos. In another aspect, the subject is an adult requiring parenteral nutrition.

These and other aspects are more fully described herein.

DETAILED DESCRIPTION

Figure 1:
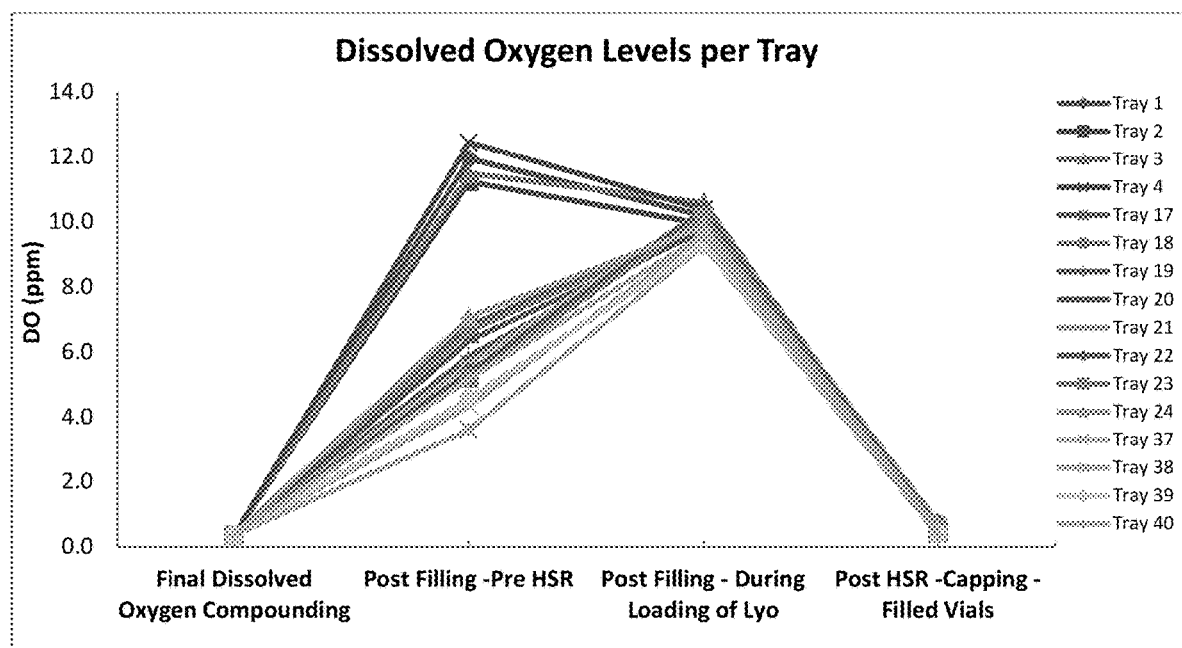
FIG. 1 depicts the overall trend of the results from the experiments that demonstrate the effectiveness of the Head Space Reduction (HSR) cycle in attaining reduced and consistent dissolved oxygen (DO) levels in the finished drug product. The results showed a trend with an increase in dissolved oxygen level from 0.36 parts per million (ppm) recorded during compounding, to an average of 5.12 ppm measured after filling, a further increase to an average of 9.92 ppm while loading the Lyophilizer, and finally a reduction of dissolved oxygen to an average of 0.50 ppm after headspace reduction. This demonstrates the specific phase of manufacturing at which and to the specific level that oxygen needs to be controlled in the product.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents that are within the ordinary skill in the art. In the event that one or more of the incorporated literature, patents, and similar materials differs from or contradicts this application, including but not limited to defined terms, term usage, described techniques, or the like, this application controls. Unless otherwise defined, all technical and scientific terms used herein are intended to have the same meaning as commonly understood by one of ordinary skill in this field. All publications, patent applications, patents, and other references mentioned herein are incorporated by reference in their entirety.

Advantageously, it has been found that the desirable attributes of L-cysteine compositions for infusion can be obtained without the characteristic impurity profile that is known in the art. Such impurity profile makes the product less safe to be used by patients, in particular, preterm and term infants and pediatric patients of 1 month to 1 year as well as critically ill adults. Specifically, the art formulations fail to address the issues related to the amounts of Aluminum and cysteine, among other impurities, that can be routinely present and co-administered with L-cysteine. It has now been found that L-cysteine compositions for injection can be prepared using the methods described herein whereby the compositions unexpectedly comprise exceedingly low levels of Aluminum and other undesirable impurities, such as cysteine, pyruvic acid, certain heavy metals and certain ions. As a result, the present compositions and methods of using said compositions are safer to the intended subject compared to the currently available compositions and methods. Further, the product is also rendered more stable by virtue of lower levels of cysteine generated by the manufacturing processes described herein.

As described herein, without being bound to theory, it has been found that the problems of safety, purity and stability are results not simply or directly from the level of Aluminum, but are also intertwined with dissolved oxygen levels in the composition and oxygen in the headspace as well as certain heavy metals and certain ions that may leach or be extracted out of the container closure.

An L-Cysteine for injection product was prepared with the aim to provide a product that would be acceptable for administration to infants, pediatric and adult patients. High quality Schott glass vials and stoppers were used. See Example 2. It was however found that glass containers contribute more significantly than expected to the Aluminum content of L-cysteine compositions stored therein to the point where the product did not meet the specifications for certain components. Products having such Aluminum levels would likely be deemed unsafe by the FDA. As such, efforts were focused on identifying the sources of Aluminum in the product and attempts to minimize it in the product. These efforts led to the unexpected discovery that simply removing a source of Aluminum by replacing glass with plastic did not result in a product having the desired properties.

Additional efforts to identify the root cause for the product failure led to the finding that the product likely failed because oxygen entered the plastic container and into the product at a rate higher than previously expected or predicted. For example, the plastic container product failed in some cases in less than 1-2 months. See Example 3. This finding was also unexpected. Increased oxygen levels in the product led to unacceptable levels of oxidation products, such as cysteine, which precipitated and caused particulates in the product. Particulates are dangerous in injectable compositions and create a safety concern, in addition to the stability issue to the product.

However, the precipitation may have been exacerbated by reduction in Aluminum since Aluminum in solution may have a stabilizing effect. Consequently, removing Aluminum may have the unintended consequence of increased precipitation and product failure in the presence of even small amounts of oxygen in the container. This was unexpected.

Additionally, controlling heat in the process including during the compounding and/or sterilization activities, unexpectedly was found to be beneficial for preparing stable L-Cysteine compositions described herein. This was surprising because L-Cysteine has been used in parenteral products as an excipient where the product is subjected to terminal sterilization which exposes the product to high temperatures such as 120° C.

Some subjects that would be receiving L-Cysteine supplementation are, as discussed elsewhere herein, pre-term neonates or full-term infants that are underweight, or infants that may be full term and are not underweight but are still candidates for treatment, in many cases for longer term treatment. For example, some of these subjects may be treated with L-Cysteine for several days or several weeks, even several months. In these cases, it is imperative that the subjects are not exposed to potentially toxic or undesirable levels of some anions and heavy metals that may be present in drug products. Examples of such heavy metals include but not limited to Lead, Nickel, Arsenic and Mercury. Examples of anions that should be monitored include but not limited to iodide, and fluoride. Many of these are introduced into drug products through manufacturing processes, container closure systems, or the drug substance and the excipients. The levels of the heavy metals and anions may not be a concern with many drug products because the patient population exposed to the drug may be not as vulnerable as in the case of L-Cysteine, or the dosing of such drug products may be very limited, i.e., for one or a few doses. For the reasons noted above, it is imperative that L-Cysteine drug product, its administration, its manufacture, and its container closure system are carefully evaluated for the levels of heavy metals and selected anions. The state of the art is lacking in providing any specific guidance on the need for this evaluation, the specific heavy metals and anions on which to focus, and how to achieve control over the levels. The L-Cysteine compositions, methods of administration and manufacture, selection of container closure system and the excipients and the drug substance as described herein fill that need.

Thus, in summary, as described herein, reducing aluminum drastically to extremely low levels in the product, reducing oxygen to very low levels in the process and in the composition, and/or reducing or eliminating heat in the process, and in consideration of data showing selection of the appropriate container, stopper, drug substance, and excipients, individually or in combination(s), resulted in achieving a safe, stable composition of L-Cysteine injection that could be administered safely even to very delicate pediatric subjects such as pre-term neonatal subjects that are as young as a day and may weigh as low as 0.5 kilos, for a few days to several weeks.

L-cysteine for injection is a marketed product used as a component of a nutritional supplement regimen referred to as total parenteral nutrition (TPN). The Aluminum content in known L-cysteine compositions for injection is higher than desired. Moreover, when the L-cysteine composition is combined with certain amino acids prior to administration, the amino acids contribute some amount of Aluminum, and Aluminum levels can further increase. TPN admixtures constitute several other components (in addition to amino acid mixtures) such as electrolytes (such as Potassium Phosphate, Calcium gluconate, and sodium acetate). These electrolytes may also contribute to high Aluminum levels in TPN admixtures (Smith et al., Am. J. Health Syst. Pharm., vol. 64, Apr. 1, 2007, pp. 730-739). This is of particular concern since administration of the L-cysteine is often to infants (some of them pre-term) for nutritional support. A focus of the subject matter described herein is in minimizing the Aluminum levels coming from L-Cysteine compositions so that when admixed with other ingredients of TPN admixtures, the overall Aluminum levels could be reduced while minimizing introduction of undesirable materials such as heavy metals, anions, and particulates. All of these components are present in amounts that are below levels determined to be safe.

L-cysteine (2-Amino-3-sulfhydrylpropanoic acid) is a sulfur-containing amino acid having a structure according to Formula I:

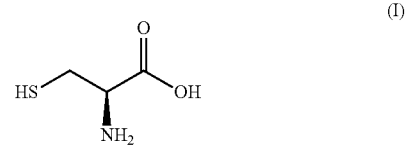

L-cysteine performs a variety of metabolic functions. For example, L-cysteine is a precursor for antioxidants, such as glutathione and taurine, that support oxidative defense and a healthy immune system. L-cysteine can also play a role in the synthesis of essential fatty acids and facilitate production of cell membranes and protective covers of nerve endings. Additionally, L-cysteine can be an important precursor for many proteins, such as structural proteins in connective tissue. Thus, the depletion or absence of cystathionase activity in premature fetuses and newborns to synthesize L-cysteine de novo has led to the categorization of L-cysteine as a conditionally essential amino acid. Additionally, administration of L-cysteine can be valuable to treat a number of conditions in subjects, whether or not the subject is a premature infant or neonate.

Known pharmaceutical compositions that contain L-cysteine can typically contain undesirable levels of certain components. Cystine is an oxidation product of L-cysteine. Like L-cysteine, cysteine can be synthesized in the liver. Further, both L-cysteine and cysteine can be present as amino acid residues in proteins. However, because cysteine is an oxidation product of L-cysteine, it is possible that the amount of cysteine can increase over time. Thus, it may be desirable to maintain the amount of cysteine within predetermined levels over time. For all practical purposes, cysteine and L-Cystine are used interchangeably herein. Pyruvic acid is another undesirable compound that can be found in L-cysteine compositions known in the art. It is possible that the amount of pyruvic acid in these compositions can increase over time. Thus, it may be desirable to maintain the amount of pyruvic acid within predetermined levels over time.

Perhaps of most concern is the level of Aluminum in known L-cysteine compositions. Aluminum contamination and associated Aluminum toxicity can lead to a number of adverse conditions such as metabolic bone disease, neurodevelopmental delay, cholestasis, osteoporosis, growth failure, dementia, and the like. It is desirable to allow no more than 4-5 mcg/kg/day of Aluminum to avoid toxicity. It is preferable to keep the dose on the conservative side as much as possible, i.e., at 4 mcg/kg/day to avoid accidental overdosing in case Aluminum from some other reason (unanticipated or unknown source or due to human error) is introduced. Up to now, known L-cysteine compositions contain up to 5000 ppb Aluminum. Even levels of 900 ppb are known in currently available products. In stark contrast, described herein are compositions that provide a therapeutically effective amount of L-cysteine, while containing less than 250 ppb Aluminum, including, in certain embodiments, less than 200 ppb, or less than 175 ppb, or less than 150 ppb, or less than 125 ppb, or less than 120 ppb, or less than 100 ppb, or less than 80 ppb, or less than 75 ppb, or less than 60 ppb, or less than 50 ppb, or less than 40 ppb, or less than 30 ppb, or less than 20 ppb, or less than 10 ppb, or less than 5 ppb, or less than 1.0 ppb. Thus, what has now been achieved is an unexpected and substantial reduction in Aluminum content of an L-Cysteine composition that permits exposure to less than or equal to 4-5 micrograms per kilogram per day (μg/kg/d) to avoid or minimize Aluminum toxicity while still providing therapeutically effective L-cysteine in a stable composition. In some aspects, the compositions described herein permit an Aluminum dose of as low as 0.6 micrograms/kg/d, improving significantly the safety of the L-Cysteine product and its administration.

High risk patient populations for Aluminum toxicity in the context of parenteral nutrition include the following: Renal Insufficiency and Infants: Renal elimination is a major source of Aluminum removal. Therefore, patients with renal compromise and infants with immature renal function are at risk of Aluminum accumulation. Pregnant women: The fetus is vulnerable to Aluminum contamination in parenteral nutrition since Aluminum may be transferred across the placenta. Elderly: Age is a well-known risk factor for renal impairment and thus results in a higher risk of Aluminum toxicity. Other studies suggest that Aluminum toxicity may be due to increased absorption of Aluminum due to a weakened GI protective barrier.

The compositions and methods described herein provide the means to support the nutritional needs of patients, including preterm infants or infants with low birth weight, but reduce the risks associated with Aluminum ingestion. Most preterm and low birth weight infants tend to require parenteral nutrition with amino acid supplementation during their hospital stay. However, as mentioned above, infants are a particularly high-risk population for Aluminum toxicity. To address such issues, in certain embodiments, the compositions comprise about 34.5 mg/mL of L-cysteine (measured as a base, i.e., not measured as HCl and monohydrate) and no more than 250 ppb, preferably about 120 ppb, or lower, of Aluminum. These compositions with no more than 120 ppb of Aluminum, and in certain embodiments, about 120 ppb, or 100 ppb, or 80 ppb, or 60 ppb, or 50 ppb, or 20 ppb, or 10 ppb or 5 ppb or 1.0 ppb, or any suitable subrange encompassing the specific values, in units of 5 ppb, permit great flexibility with respect to the amino acid supplementation for TPN preparations.

L-Cysteine injection is administered after being added to a parenteral nutrition composition such as an amino acid composition, or a sugar-source such as dextrose or a lipid source or a combination of the foregoing. It is preferred that L-Cysteine is added to the amino acid composition, which may be administered separately or in combination with other components of a parenteral nutrition regime such as sugars and lipids. For present purposes, the Aluminum content of the combined L-Cysteine and amino acid solution is of interest, and is monitored. L-Cysteine may be dosed at 15 mg per gram of amino acids or sometimes at a high concentration, i.e., 40 mg/gram of amino acids.

Commercially available amino acid product labeling for example indicates that 25 mcg/L of Aluminum is contributed from the product itself. The general recommended maximum dose is 4 g of amino acids/kg body weight. Generally amino acids solutions are available as 10% (10 g/100 mL) which would necessitate 40 mL volume to be administered for a 1 kg preterm neonatal patient. Based on this the amino acids solution is expected to contribute to about 1 mcg/kg/day. This leaves about 3 mcg/kg/day from other sources including L-cysteine. In some scenarios, there may be five or more other components including L-cysteine that can contribute to varying levels of Aluminum in TPN mixtures. For the sake of illustration, assume there are five contributors that contribute equally. The expected maximum Aluminum contribution that may come from L-Cysteine would be (3 mcg/kg/day)/5=0.6 mcg/kg/day. In light of Smith et al. (Am. J. Health Syst. Pharm., vol. 64, Apr. 1, 2007, pp. 730-739), significant contributors to Aluminum levels besides amino acids and L-Cysteine are Potassium Phosphate, Potassium Acetate, Sodium Acetate, and Calcium Gluconate. The reference indicates that contributions from all of these are high such that 100% of pediatric (including preterm and full-term infants) TPNs have >4 μg/kg/day (range 12-162 μg/kg/day) of Aluminum coming from various sources. Even after carefully selecting the products with the least Aluminum content components among those available for treatment, the TPNs have >4 μg/kg/day. This finding for example highlights the need to systematically reduce the amount of Aluminum in each product that will be incorporated into a TPN admixture. The current efforts are directed to providing L-Cysteine compositions that offer exceedingly low Aluminum levels.

One of the difficulties with establishing dosing levels of L-Cysteine with an eye to keep the Aluminum administration to below or at a certain amount is the lack of uniformity in the art as to how to categorize the subjects in terms of their age and weight. This imprecise terminology has been used often blurring the boundaries among the patient groups, making it difficult to assess which patient should receive what amount of L-Cysteine, and hence how much Aluminum would result. As such, the art does not suggest what the levels of Aluminum exposure should be, nor does it provide a solution that minimizes Aluminum exposure during a TPN regimen. Following Table 1 shows a streamlined approach to categorize the potential patient population and their proposed daily doses of L-Cysteine.

TABLE 1

Daily Dosage of L-Cysteine

| Age | Protein[a] Requirement (g/kg/day)[1] | L-Cysteine Dosage (mg cysteine/ g AA) | L-Cysteine Dosage (mg cysteine/ kg/day) |
|---|---|---|---|
| Preterm and term infants less than 1 month of age | 3 to 4 | 15 | 45 to 60 |
| Pediatric patients 1 month to less than 1 year of age | 2 to 3 | 15 | 30 to 45 |
| Pediatric patients 1 year to 11 years of age | 1 to 2 | 15 | 15 to 30 |
| Pediatric patients 12 years to 17 years of age | 0.8 to 1.5 | 5 | 4 to 7.5 |
| Adults: Stable Patients | 0.8 to 1 | 5 | 4 to 5 |
| Adults: Critically Ill Patients | 1.5 to 2 | 5 | 7.5 to 10 |

[a]Protein is provided as amino acids. When infused intravenously, amino acids are metabolized and utilized as the building blocks of protein.

From the above Table, it should be noted that the most need for L-Cysteine is for the preterm infant. Therefore, to safely administer L-Cysteine compositions, the Aluminum level in the compositions must be substantially less than what is in commercially available products and those described in the art. There has been no specific guidance in the art however of how low this Aluminum level should be, and how to achieve compositions with such low Aluminum levels. To the extent there may be some guidance, the levels proposed are considered higher than desirable.

L-Cysteine Injection as presented herein in some embodiments contains no more than 120 mcg/L (120 ppb) of aluminum (0.0035 mcg of aluminum/mg of cysteine). The maximum dosage of aluminum from L-Cysteine Injection is not more than 0.21 mcg/kg/day when preterm and term infants less than 1 month of age are administered the dosage of L-Cysteine injection (15 mg cysteine/g of amino acids and 4 g of amino acids/kg/day). If L-Cysteine is added to TPN containing amino acid and dextrose solutions (which each may contain up to 25 mcg/L of aluminum) as well as other additive drug products, the total amount of aluminum administered to the patient from the final admixture should be considered and maintained at no more than 5 mcg/kg/day.

However, with prolonged parenteral administration in patients with renal impairment, the aluminum contained in L-Cysteine Injections disclosed herein may reach toxic levels. Preterm infants are at a greater risk for aluminum toxicity because their kidneys are immature, and they require large amounts of calcium and phosphate solutions, which also contain aluminum. Prolonged administration herein may mean at least one week, or may be up to 2-4 weeks. In some aspects, the administration could continue for up to 24 weeks.

Patients with renal impairment, including preterm infants, who receive parenteral levels of aluminum at greater than 4 to 5 mcg/kg/day, accumulate aluminum at levels associated with central nervous system and bone toxicity. Tissue loading may occur at even lower rates of administration. Therefore, it is essential that aluminum levels in the L-Cysteine drug product are carefully controlled and kept at as low as possible. Such embodiments are disclosed herein.

Looking more specifically at contribution of Aluminum by the prior products, data show that the Aluminum levels of 5,000 ppb or even the 900 ppb associated with these products are not desirable or acceptable. Tables 2-3 report the Aluminum contribution from the commercial product of prior art with 900 ppb or 5000 ppb Aluminum level based on two scenarios: a) an L-Cysteine dosing regimen based on 15 mg/gram of amino acids; and b) an L-Cysteine dosing regimen based on 40 mg/gram of amino acids. The Tables also show the Aluminum contribution from an L-Cysteine product as described herein and having a level of 120 ppb.

TABLE 2

Aluminum Contribution (Based on a Cysteine Dose of 15 mg/g of Amino Acids) from an L-Cysteine Product with 900 ppb, 5,000 ppb, or 120 ppb of Aluminum

| Age | L-Cysteine Dose at (15 mg/g AA) | | Aluminum Contribution from 900 ppb product | Aluminum Contribution from 5,000 ppb product | Aluminum Contribution from 120 ppb product |
|---|---|---|---|---|---|
| | mg/kg/day | mL/kg/day | mcg/kg/day | mcg/kg/day | mcg/kg/day |
| Preterm and term infants less than 1 month | 45 to 60 | 1.31 to 1.74 | 1.18 to 1.57 | 6.53 to 8.70 | 0.157 to 0.209 |
| Pediatric patients 1 month to less than 1 yr | 30 to 45 | 0.87 to 1.31 | 0.79 to 1.17 | 4.35 to 6.52 | 0.1 to 0.157 |
| Pediatric patients 1 yr to 11 yrs | 15 to 30 | 0.44 to 0.87 | 0.40 to 0.79 | 2.18 to 4.35 | 0.053 to 0.1 |
| Pediatric patients 12 yrs to 17 yrs | 4 to 7.5 | 0.18 to 0.22 | 0.11 to 0.20 | 0.58 to 1.09 | 0.022 to 0.026 |
| Adults: Stable Patients | 4 to 5 | 0.18 to 0.23 | 0.11 to 0.14 | 0.58 to 0.73 | 0.022 to 0.028 |
| Adults: Critically ill patients | 7 to 10 | 0.32 to 0.46 | 0.2 to 0.28 | 1.02 to 1.46 | 0.038 to 0.055 |

TABLE 3

Aluminum Contribution (Based on a Cysteine Dose of 40 mg/g of Amino Acids) from an L-Cysteine Product with 900 ppb, 5,000 ppb, or 120 ppb of Aluminum

| Age | L-Cysteine Dose at (40 mg/g AA) | | Aluminum Contribution from 900 ppb product | Aluminum Contribution from 5,000 ppb product | Aluminum Contribution from 120 ppb product |
|---|---|---|---|---|---|
| | mg/kg/day | mL/kg/day | mcg/kg/day | mcg/kg/day | mcg/kg/day |
| Preterm and term infants less than 1 month | 120 to 160 | 3.48 to 4.64 | 3.13 to 4.17 | 17.39 to 23.19 | 0.42 to 0.56 |
| Pediatric patients 1 month to less than 1 yr | 80 to 120 | 2.32 to 3.48 | 2.09 to 3.13 | 11.59 to 17.39 | 0.28 to 0.42 |
| Pediatric patients 1 yr to 11 yrs | 40 to 80 | 1.16 to 2.32 | 1.05 to 2.09 | 5.79 to 11.59 | 0.14 to 0.28 |
| Pediatric patients 12 yrs to 17 yrs | 10.66 to 20 | 0.31 to 0.58 | 0.28 to 0.53 | 1.56 to 2.94 | 0.04 to 0.07 |
| Adults: Stable Patients | 10.66 to 13.33 | 0.31 to 0.39 | 0.28 to 0.35 | 1.56 to 1.94 | 0.04 to 0.047 |
| Adults: Critically ill patients | 18.7 to 26.7 | 0.54 to 0.77 | 0.49 to 0.70 | 2.72 to 3.89 | 0.065 to 0.09 |

If the preterm infants are given the high dose of L-cysteine (40 mg/gram of amino acids), this requires that a dose of 160 mg/kg (4.64 mL/kg) of L-Cysteine at a (base) concentration of 34.5 mg/mL be delivered. (See Table 3 above). The compositions described herein contribute about 0.0035 mcg Aluminum per each mg of L-cysteine, or 0.12 mcg of Aluminum per each mL at 120 ppb. Thus, a dose of 160 mg/kg (4.64 mL/kg) L-cysteine delivers only 0.56 mcg/kg Aluminum at 40 mg/g of AA dosing on the higher end, or 0.157 mcg/kg at 15 mg/g of AA dosing on the lower end. See Tables 2-3. In contrast, if art products were to be used, these patients would receive either 23 mcg/kg (for the product that contains 5,000 ppb of Aluminum), or 4.2 mcg/kg of aluminum (for the product that contains 900 ppb of Aluminum). Given that the total daily intake permissible for Aluminum is expected to be ideally less than 4-5 mcg/kg, the art products already exceed the entire daily Aluminum level and do not leave room for Aluminum contribution from other TPN components. Therefore, these known high Aluminum-containing products are likely to be deemed unsafe by the FDA and are neither desirable nor acceptable. In contrast, the L-Cysteine compositions presented herein provide Aluminum levels ranging from 10 ppb to about 250 ppb. Taking 20 ppb, 50 ppb, 120 ppb, and 150 ppb as illustrations, the Tables below estimate the amount of Aluminum delivered for each class of patients using 34.5 mg/mL L-Cysteine product when being dosed at 15 mg/g of Amino Acids.

TABLE 4

Aluminum Contribution (Based on a Cysteine Dose of 15 mg/g of Amino Acids) from an L-Cysteine Product (34.5 mg/mL) with 20 ppb, 50 ppb, 120 ppb or 150 ppb of Aluminum

| Age | L-Cysteine Dose at 15 mg/g AA mg/kg/day | Aluminum Contribution from 20 ppb product mcg/kg/day | Aluminum Contribution from 50 ppb product mcg/kg/day | Aluminum Contribution from 120 ppb product mcg/kg/day | Aluminum Contribution from 150 ppb product mcg/kg/day |
|---|---|---|---|---|---|
| Preterm and term infants less than 1 month | 45 to 60 | 0.026 to 0.035 | 0.065 to 0.088 | 0.157 to 0.209 | 0.195 to 0.26 |
| Pediatric patients 1 month to less than 1 yr | 30 to 45 | 0.017 to 0.026 | 0.043 to 0.065 | 0.1 to 0.157 | 0.13 to 0.195 |
| Pediatric patients 1 yr to 11 yrs | 15 to 30 | 0.009 to 0.017 | 0.022 to 0.044 | 0.053 to 0.11 | 0.066 to 0.125 |
| Pediatric patients 12 yrs to 17 yrs | 4 to 7.5 | 0.004 | 0.009 to 0.01 | 0.022 to 0.026 | 0.027 to 0.033 |
| Adults: Stable Patients | 4 to 5 | 0.004 | 0.009 to 0.12 | 0.022 to 0.028 | 0.027 to 0.035 |

TABLE 4-continued

Aluminum Contribution (Based on a Cysteine Dose of 15 mg/g of Amino Acids)
from an L-Cysteine Product (34.5 mg/mL) with 20 ppb, 50 ppb, 120 ppb or
150 ppb of Aluminum

| Age | L-Cysteine Dose at 15 mg/g AA mg/kg/day | Aluminum Contribution from 20 ppb product mcg/kg/day | Aluminum Contribution from 50 ppb product mcg/kg/day | Aluminum Contribution from 120 ppb product mcg/kg/day | Aluminum Contribution from 150 ppb mcg/kg/day |
|---|---|---|---|---|---|
| Adults: Critically ill patients | 7 to 10 | 0.006 to 0.009 | 0.016 to 0.23 | 0.038 to 0.055 | 0.048 to 0.069 |

In some embodiments, parenteral L-Cysteine compositions provide about 35 mg/mL of L-Cysteine to deliver 45 to 60 mg/kg/day of L-Cysteine and from about 0.02 to about 0.3 mcg/kg/day of Aluminum. In some embodiments, parenteral L-Cysteine compositions provide about 35 mg/mL of L-Cysteine to deliver 30 to 45 mg/kg/day of L-Cysteine and from about 0.01 to about 0.25 mcg/kg/day of Aluminum. In some embodiments, parenteral L-Cysteine compositions provide about 35 mg/mL of L-Cysteine to deliver 15 to 30 mg/kg/day of L-Cysteine and from about 0.005 to about 0.15 mcg/kg/day of Aluminum.

In some embodiments, parenteral L-Cysteine compositions provide about 35 mg/mL of L-Cysteine to deliver 4 to 7.5 mg/kg/day of L-Cysteine and from about 0.003 to about 0.04 mcg/kg/day of Aluminum. In some embodiments, parenteral L-Cysteine compositions provide about 35 mg/mL of L-Cysteine to deliver 4 to 5 mg/kg/day of L-Cysteine and from about 0.003 to about 0.04 mcg/kg/day of Aluminum. In some embodiments, parenteral L-Cysteine compositions provide about 35 mg/mL of L-Cysteine to deliver 7 to 10 mg/kg/day of L-Cysteine and from about 0.004 to about 0.08 mcg/kg/day of Aluminum.

In some embodiments, a method of safe administration of L-Cysteine comprises administering to preterm and term infants of less than 1 month of age a parenteral L-Cysteine composition that delivers 45 to 60 mg/kg/day of L-Cysteine and from about 0.02 to about 0.3 mcg/kg/day of Aluminum, admixed with a parenteral nutrition composition. In some embodiments, a method of safe administration of L-Cysteine comprises administering to pediatric patients 1 month to less than 1 year of age a parenteral L-Cysteine composition that delivers 30 to 45 mg/kg/day of L-Cysteine and from about 0.01 to about 0.25 mcg/kg/day of Aluminum, admixed with a parenteral nutrition composition. In some embodiments, a method of safe administration of L-Cysteine comprises administering to pediatric patients 1 year to 11 years of age a parenteral L-Cysteine composition that delivers 15 to 30 mg/kg/day of L-Cysteine and from about 0.005 to about 0.15 mcg/kg/day of Aluminum, admixed with a parenteral nutrition composition.

In some embodiments, a method of safe administration of L-Cysteine comprises administering to pediatric patients 12 years to 17 years of age a parenteral L-Cysteine composition that delivers 4 to 7.5 mg/kg/day of L-Cysteine and from about 0.003 to about 0.04 mcg/kg/day of Aluminum, admixed with a parenteral nutrition composition. In some embodiments, a method of safe administration of L-Cysteine comprises administering to adult stable patients a parenteral L-Cysteine composition that delivers 4 to 5 mg/kg/day of L-Cysteine and from about 0.003 to about 0.04 mcg/kg/day of Aluminum, admixed with a parenteral nutrition composition. In some embodiments, a method of safe administration of L-Cysteine comprises administering to critically ill adult patients a parenteral L-Cysteine composition that delivers 7 to 10 mg/kg/day of L-Cysteine and from about 0.004 to about 0.08 mcg/kg/day of Aluminum, admixed with a parenteral nutrition composition.

Further, taking 20 ppb, 50 ppb, 120 ppb, and 150 ppb as illustrations, the Tables below estimate the amount of Aluminum delivered for each class of patients using 34.5 mg/mL L-Cysteine product when being dosed at 40 mg/g of Amino Acids.

TABLE 5

Aluminum Contribution (Based on a Cysteine Dose of 40 mg/g of Amino Acids)
from an L-Cysteine Product (34.5 mg/mL) with 20 ppb, 50 ppb, 120 ppb or
150 ppb of Aluminum

| Age | L-Cysteine Dose at 40 mg/g AA mg/kg/day | Aluminum Contribution from 20 ppb product mcg/kg/day | Aluminum Contribution from 50 ppb product mcg/kg/day | Aluminum Contribution from 120 ppb product mcg/kg/day | Aluminum Contribution from 150 ppb mcg/kg/day |
|---|---|---|---|---|---|
| Preterm and term infants less than 1 month | 120 to 160 | 0.07 to 0.09 | 0.175 to 0.233 | 0.42 to 0.56 | 0.525 to 0.7 |
| Pediatric patients 1 month to less than 1 yr | 80 to 120 | 0.047 to 0.07 | 0.117 to 0.175 | 0.28 to 0.42 | 0.35 to 0.525 |
| Pediatric patients 1 yr to 11 yrs | 40 to 80 | 0.023 to 0.047 | 0.058 to 0.117 | 0.14 to 0.28 | 0.175 to 0.35 |

TABLE 5-continued

Aluminum Contribution (Based on a Cysteine Dose of 40 mg/g of Amino Acids) from an L-Cysteine Product (34.5 mg/mL) with 20 ppb, 50 ppb, 120 ppb or 150 ppb of Aluminum

| Age | L-Cysteine Dose at 40 mg/g AA mg/kg/day | Aluminum Contribution from 20 ppb product mcg/kg/day | Aluminum Contribution from 50 ppb product mcg/kg/day | Aluminum Contribution from 120 ppb product mcg/kg/day | Aluminum Contribution from 150 ppb mcg/kg/day |
|---|---|---|---|---|---|
| Pediatric patients 12 yrs to 17 yrs | 10.66 to 20 | 0.007 to 0.012 | 0.017 to 0.029 | 0.04 to 0.07 | 0.05 to 0.088 |
| Adults: Stable Patients | 10.66 to 13.33 | 0.007 to 0.008 | 0.017 to 0.02 | 0.04 to 0.047 | 0.05 to 0.059 |
| Adults: Critically ill patients | 18.7 to 26.7 | 0.011 to 0.015 | 0.027 to 0.038 | 0.065 to 0.09 | 0.081 to 0.113 |

In some embodiments, parenteral L-Cysteine compositions provide about 35 mg/mL of L-Cysteine to deliver 120 to 160 mg/kg/day of L-Cysteine and from about 0.05 to about 0.8 mcg/kg/day of Aluminum. In some embodiments, parenteral L-Cysteine compositions provide about 35 mg/mL of L-Cysteine to deliver 80 to 120 mg/kg/day of L-Cysteine and from about 0.03 to about 0.6 mcg/kg/day of Aluminum. In some embodiments, parenteral L-Cysteine compositions provide about 35 mg/mL of L-Cysteine to deliver 40 to 80 mg/kg/day of L-Cysteine and from about 0.01 to about 0.4 mcg/kg/day of Aluminum.

In some embodiments, parenteral L-Cysteine compositions provide about 35 mg/mL of L-Cysteine to deliver 10 to 20 mg/kg/day of L-Cysteine and from about 0.005 to about 0.1 mcg/kg/day of Aluminum. In some embodiments, parenteral L-Cysteine compositions provide about 35 mg/mL of L-Cysteine to deliver 10 to 15 mg/kg/day of L-Cysteine and from about 0.005 to about 0.06 mcg/kg/day of Aluminum. In some embodiments, parenteral L-Cysteine compositions provide about 35 mg/mL of L-Cysteine to deliver about 18 to 28 mg/kg/day of L-Cysteine and from about 0.01 to about 0.15 mcg/kg/day of Aluminum.

In some embodiments, a method of safe administration of L-Cysteine comprises administering to preterm and term infants of less than 1 month of age a parenteral L-Cysteine composition that delivers 120 to 160 mg/kg/day of L-Cysteine and from about 0.05 to about 0.8 mcg/kg/day of Aluminum, admixed with a parenteral nutrition composition. In some embodiments, a method of safe administration of L-Cysteine comprises administering to pediatric patients 1 month to less than 1 year of age a parenteral L-Cysteine composition that delivers 80 to 120 mg/kg/day of L-Cysteine and from about 0.03 to about 0.6 mcg/kg/day of Aluminum, admixed with a parenteral nutrition composition. In some embodiments, a method of safe administration of L-Cysteine comprises administering to pediatric patients 1 year to 11 years of age a parenteral L-Cysteine composition that delivers 40 to 80 mg/kg/day of L-Cysteine and from about 0.01 to about 0.4 mcg/kg/day of Aluminum, admixed with a parenteral nutrition composition.

In some embodiments, a method of safe administration of L-Cysteine comprises administering to pediatric patients 12 years to 17 years of age a parenteral L-Cysteine composition that delivers 10 to 20 mg/kg/day of L-Cysteine and from about 0.005 to about 0.1 mcg/kg/day of Aluminum, admixed with a parenteral nutrition composition. In some embodiments, a method of safe administration of L-Cysteine comprises administering to adult stable patients a parenteral L-Cysteine composition that delivers 10 to 15 mg/kg/day of L-Cysteine and from about 0.005 to about 0.06 mcg/kg/day of Aluminum, admixed with a parenteral nutrition composition. In some embodiments, a method of safe administration of L-Cysteine comprises administering to critically ill adult patients a parenteral L-Cysteine composition that delivers 18 to 28 mg/kg/day of L-Cysteine and from about 0.01 to about 0.15 mcg/kg/day of Aluminum, admixed with a parenteral nutrition composition.

Accordingly, what is provided herein, among other things, are therapeutically and/or nutritionally effective amounts of L-cysteine with significantly minimized risk of Aluminum toxicity.

I. Definitions

As used herein, the term "stable" refers to a composition that has the component profiles described herein, for example, Aluminum, L-Cystine, and pyruvic acid, at the levels described and for the amount of time identified. In other words, a stable composition will contain the specified levels of all components for sufficient period of time to enable the composition to be commercially manufactured, stored, shipped, and administered in a clinical setting. In general, products are considered stable if the period of time is three months, or three to six months, or three to 12 months, or three to 15 months, or three to 18 months or three to 24 months.

As used herein, the term "dissolved oxygen" refers to oxygen that is found in the aqueous carrier of the compositions. Distinguished from dissolved oxygen is the headspace oxygen. As used herein, the term "headspace oxygen" refers to the oxygen that is found in the headspace volume of the sealed container comprising the composition.

As used herein, the term "cysteine precipitate" refers to undissolved L-cysteine. The undissolved cysteine may be visually detected as particulate matter in solution.

As used herein, "subject" refers to a mammal that may benefit from the administration of a composition described herein. In one aspect, the mammal may be a human.

The term "prophylaxis" or "prophylactic" refers to the continued absence of symptoms of the disease or condition that would be expected had the combination not been administered.

As used herein, the terms "formulation" and "composition" are used interchangeably and refer to a mixture of two or more compounds, elements, or molecules.

In some aspects, the terms "formulation" and "composition" may be used to refer to a mixture of one or more active agents with a carrier or other excipients. Compositions can take nearly any physical state, including solid and/or liquid (i.e. solution). Furthermore, the term "dosage form" can include one or more formulation(s) or composition(s) provided in a form suitable for administration to a subject. As used herein, the term "compositions for injection" and the like, refers to a composition that is intended for injection, including dilution and admixing with other components prior to injection. Said injection may be administered as an intravenous injection, or as an intravenous infusion. When administered as infusions, the compositions may be administered through a peripheral vein in limited circumstances or more commonly through a central vein. One of skill in the art would have experience with such administrations.

As used herein, "effective amount" refers to an amount of an ingredient, such as L-cysteine, which, when included in a composition, is sufficient to achieve an intended compositional or physiological effect. Thus, a "therapeutically or nutritionally effective amount" refers to a non-toxic, but sufficient amount of an active agent, to achieve therapeutic or nutritional results in treating or preventing a condition for which the active agent is known to be effective or providing nutritional value to prevent effects of malnutrition. It is understood that various biological factors may affect the ability of a substance to perform its intended task. Therefore, an "effective amount" or a "therapeutically or nutritionally effective amount" may be dependent in some instances on such biological factors. Additionally, in some cases an "effective amount" or a "therapeutically or nutritionally effective amount" may not be achieved in a single dose. Rather, in some examples, an "effective amount" or a "therapeutically or nutritionally effective amount" can be achieved after administering a plurality of doses over a period of time, such as in a pre-designated dosing regimen. Further, while the achievement of therapeutic/nutritional effects may be measured by a physician or other qualified medical personnel using evaluations known in the art, it is recognized that individual variation and response to treatments may make the achievement of therapeutic or nutritional effects a subjective decision. The determination of an effective amount is well within the ordinary skill in the art of pharmaceutical and nutritional sciences as well as medicine.

As used herein, the term "substantially" refers to the complete or nearly complete extent or degree of a component, or an action, characteristic, property, state, structure, item, or result. The exact allowable degree of deviation from absolute presence of such a component, or an action, characteristic, property, state, structure, item, or result may in some cases depend on the specific context. However, generally speaking, "substantially" will be so near as to have the same overall result as if absolute and total extent or degree were obtained. The use of "substantially" is equally applicable when used in a negative connotation to refer to the complete or near complete lack of a component, or an action, characteristic, property, state, structure, item, or result. For example, a composition that is "substantially free of" a component would either completely lack the component, or so nearly completely lack the component that the effect would be the same as if it completely lacked the component. In other words, a composition that is "substantially free of" an ingredient or element may still actually contain such component as long as there is no measurable effect thereof, for example, trace amounts. As used herein, "essentially free" means a component, or an action, characteristic, property, state, structure, item, or result is not present or is not detectable.

The terms "treat" and "treatment" refer to both therapeutic treatment and prophylactic or preventative measures, wherein the object is to prevent or slow down (lessen) an undesired physiological change, disorder or adverse health condition. For purposes of this disclosure, beneficial or desired clinical results include, but are not limited to, alleviation of symptoms, diminishment of extent of the condition, stabilized (i.e., not worsening) state of the condition, delay or slowing of progression of the condition, amelioration or palliation of the condition, and absence of condition (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith. The phrase "pharmaceutically acceptable salt," as used herein, refers to pharmaceutically acceptable organic or inorganic salts of a molecule. A pharmaceutically acceptable salt may involve the inclusion of another molecule that acts as a counterion. The counterion may be any organic or inorganic moiety that stabilizes the charge on the parent compound. Furthermore, a pharmaceutically acceptable salt may have more than one charged atom in its structure. Hence, a pharmaceutically acceptable salt can have one or more charged atoms and/or one or more counterions. In the case of L-cysteine, the hydrochloride salt form is preferred.

The phrase "single-use container" refers to a sealed pharmaceutically prepared container holding a drug product in a sterile environment that is intended to be used in a single operation of transferring the entire contents or substantially entire contents, wherein the transfer operation spans no more than 10-12 hrs, but often less than 8 hrs, or even six hours. It should be recognized that the single-use container is generally preservative-free and that if multiple transfers are attempted, they should be completed in a short duration, i.e., less than about 8-10 hrs from the first breach of the sterile environment. In some aspects the single-use container may be used to administer all of its contents to one subject in need thereof. In some aspects the single-use container may be used to administer its contents to more than one subject in need thereof.

As used herein, the term "mixing" refers to admixing, contacting, blending, stirring or allowing to admix, mix, blend, stir and the like.

As used herein, the term "safe" refers generally to a property of the compositions and methods described herein relative to art method and compositions and/or to FDA regulatory determination of the compositions and methods as part of a therapeutically or nutritionally effective regimen. For example, with respect to known L-Cysteine compositions, an Aluminum level of greater than 300 ppb would be generally considered to render the L-Cysteine product unsafe. Other examples with respect to safety are described and discussed herein with respect to Aluminum, pyruvate, Cystine, heavy metals, anions, and particulates.

Additional definitions are provided herein where appropriate.

II. Compositions

In certain aspects, the subject matter described herein is directed to a safe, stable L-cysteine composition for parenteral administration, comprising:

L-cysteine or a pharmaceutically acceptable salt thereof and/or hydrate thereof in an amount from about 10 mg/mL to about 100 mg/mL; Aluminum (Al) in an amount from about 1.0 parts per billion (ppb) to about 250 ppb;

L-cysteine in an amount from about 0.001 wt % to about 2.0 wt % relative to L-cysteine;

pyruvic acid in an amount from about 0.001 wt % to about 2.0 wt % relative to L-cysteine;

a pharmaceutically acceptable carrier, comprising water;

headspace $O_2$ that is from about 0.5% to 4.0% from the time of manufacture to about 1 month from manufacture when stored at room temperature;

dissolved oxygen present in the carrier in an amount from about 0.1 parts per million (ppm) to about 5 ppm from the time of manufacture to about 1 month from manufacture when stored at room temperature;

wherein the composition is enclosed in a single-use container having a volume of from about 10 mL to about 100 mL.

In certain aspects, the subject matter described herein is directed to a safe, stable L-cysteine composition for parenteral administration, comprising:

L-cysteine or a pharmaceutically acceptable salt thereof and/or hydrate thereof in an amount from about 10 mg/mL to about 100 mg/mL; Aluminum (Al) in an amount from about 1.0 parts per billion (ppb) to about 250 ppb;

L-cysteine in an amount from about 0.001 wt % to about 2.0 wt % relative to L-cysteine;

pyruvic acid in an amount from about 0.001 wt % to about 2.0 wt % relative to L-cysteine;

a pharmaceutically acceptable carrier, comprising water;

headspace $O_2$ that is from about 0.5% to 4.0% from the time of manufacture to about 1 month from manufacture when stored at room temperature;

dissolved oxygen present in the carrier in an amount from about 0.1 parts per million (ppm) to about 5 ppm from the time of manufacture to about 1 month from manufacture when stored at room temperature;

optionally present can be one or more metals selected from the group consisting of Lead from about 1.0 ppb to about 10 ppb, Nickel from about 5 ppb to about 40 ppb, Arsenic from about 0.1 ppb to 10 ppb, and Mercury from about 0.2 ppb to about 5.0 ppb;

wherein the composition is enclosed in a single-use container having a volume of from about 10 mL to about 100 mL.

The Aluminum in a composition can be determined using any known analytical method, such as those required by FDA regulations, and can include atomic absorption and mass spectrometry. In certain embodiments, the Aluminum that is present in the compositions is present in an amount from about 1.0 ppb to about 250 ppb, or from about 1.0 ppb to about 180 ppb, or from about 1.0 ppb to about 170 ppb, or from about 1.0 ppb to about 160 ppb, or from about 1.0 ppb to about 150 ppb, or from about 1.0 ppb to about 130 ppb, or from about 1.0 ppb to about 100 ppb, or from about 1.0 ppb to about 50 ppb, or from about 1.0 ppb to about 20 ppb.

In some embodiments the L-Cysteine and Aluminum are at a ratio of from about 35 million:1 (i.e., about 35 million units of L-Cysteine to 1 unit of Aluminum). In some embodiments the L-Cysteine and Aluminum are at a ratio of about 4 million:1. In some embodiments the L-Cysteine and Aluminum are at a ratio of about 1.8 million:1 (i.e., about 1.8 million units of L-Cysteine to 1 unit of Aluminum). In some embodiments the L-Cysteine and Aluminum are at a ratio of about 700,000:1 (i.e., about 700,000 units of L-Cysteine to 1 unit of Aluminum). In some embodiments the L-Cysteine and Aluminum are at a ratio of about 300,000:1 (i.e., about 300,000 units of L-Cysteine to 1 unit of Aluminum). In some embodiments the L-Cysteine and Aluminum are at a ratio of about 230,000:1 (i.e., about 230,000 units of L-Cysteine to 1 unit of Aluminum). In some embodiments the L-Cysteine and Aluminum are at a ratio of about 170,000:1 (i.e., about 170,000 units of L-Cysteine to 1 unit of Aluminum). In some embodiments the L-Cysteine and Aluminum are at a ratio of about 140,000:1 (i.e., about 140,000 units of L-Cysteine to 1 unit of Aluminum).

Thus, in some embodiments the L-Cysteine and Aluminum are at a ratio of from about 35 million:1 (i.e., about 35 million units of L-Cysteine to 1 unit of Aluminum) to about 1.8 million:1 (i.e., about 1.8 million units of L-Cysteine to 1 unit of Aluminum). In some embodiments the L-Cysteine and Aluminum are at a ratio of from about 4 million:1 (i.e., about 4 million units of L-Cysteine to 1 unit of Aluminum) to about 1.8 million:1 (i.e., about 1.8 million units of L-Cysteine to 1 unit of Aluminum). In some embodiments the L-Cysteine and Aluminum are at a ratio of from about 1.8 million:1 (i.e., about 1.8 million units of L-Cysteine to 1 unit of Aluminum) to about 700,000:1 (i.e., about 700,000 units of L-Cysteine to 1 unit of Aluminum). In some embodiments the L-Cysteine and Aluminum are at a ratio of from about 700,000:1 (i.e., about 700,000 units of L-Cysteine to 1 unit of Aluminum) to about 300,000:1 (i.e., about 300,000 units of L-Cysteine to 1 unit of Aluminum). In some embodiments the L-Cysteine and Aluminum are at a ratio of from about 300,000:1 (i.e., about 300,000 units of L-Cysteine to 1 unit of Aluminum) to about 230,000:1 (i.e., about 230,000 units of L-Cysteine to 1 unit of Aluminum). In some embodiments the L-Cysteine and Aluminum are at a ratio of from about 230,000:1 (i.e., about 230,000 units of L-Cysteine to 1 unit of Aluminum) to about 170,000:1 (i.e., about 170,000 units of L-Cysteine to 1 unit of Aluminum). Thus, in some embodiments the L-Cysteine and Aluminum are at a ratio of from about 170,000:1 (i.e., about 170,000 units of L-Cysteine to 1 unit of Aluminum) to about 140,000:1 (i.e., about 140,000 units of L-Cysteine to 1 unit of Aluminum). All subranges and individual values with increments of 5,000 units are contemplated by the present disclosure. In some embodiments, the unit of measure is nanograms. For example, in some embodiments the L-Cysteine and Aluminum are at a ratio of from about 4 million:1 nanograms (i.e., about 4 million nanograms of L-Cysteine to 1 nanogram of Aluminum) to about 1.8 million:1 nanograms (i.e., about 1.8 million nanograms of L-Cysteine to 1 nanogram of Aluminum).

In certain embodiments, the compositions comprise Aluminum in trace amounts, for example 1.0 ppb, but not more than 250 ppb after storage at ambient temperature for a period of 12 months or less, where the Aluminum comprises, from about 1.0 ppb to about 100 ppb of Aluminum from the container, from about 1.0 ppb to about 100 ppb of Aluminum from a cap of the container, from about 1.0 ppb to about 100 ppb of Aluminum from the L-cysteine, and from about 1.0 ppb to about 20 ppb of Aluminum from the water.

In certain embodiments, the compositions comprise Aluminum in an amount not more than 200 ppb after storage at ambient temperature for a period of 12 months, wherein the Aluminum comprises, from about 1.0 ppb to about 100 ppb of Aluminum from the container, from about 1.0 ppb to about 100 ppb of Aluminum from a cap of the container, from about 1.0 ppb to about 100 ppb of Aluminum from the L-cysteine, and from about 1.0 ppb to about 20 ppb of Aluminum from the water. In certain embodiments, the compositions comprise Aluminum in an amount not more than 200 ppb after storage at ambient temperature for a period of 6 months, where the Aluminum comprises, from about 1.0 ppb to about 100 ppb of Aluminum from the container, from about 1.0 ppb to about 100 ppb of Aluminum from a cap of the container, from about 1.0 ppb to about 100 ppm of Aluminum from the L-cysteine, and from about 1.0 ppb to about 20 ppb of Aluminum from the water. In certain embodiments, the compositions comprise Aluminum in an amount not more than 200 ppb after storage at ambient temperature for a period of 3 months, wherein the Aluminum comprises, from about 1.0 ppb to about 100 ppb of Aluminum from the container, from about 1.0 ppb to about 100 ppb of Aluminum from a cap of the container, from about 1.0 ppb to about 100 ppm of Aluminum from the L-cysteine, and from about 1.0 ppb to about 20 ppb of Aluminum from the water.

In certain embodiments, the dissolved oxygen is present in an amount from about 0.1 ppm to about 5.0 ppm, or from about 0.10 ppm to about 4.0 ppm, or from about 0.10 ppm to about 3.0 ppm, or from about 0.10 ppm to about 2.0 ppm, or from about 0.11 ppm to about 1.0 ppm. In particular, values of dissolved oxygen from about 0.4 ppm to about 3.8 ppm are preferred. For the sake of clarity and the ease of discussion and measurement, these values are taken for the L-Cysteine composition at the time of its manufacture (commonly known as "time zero" data point), or during and up to 1 month from time zero. Additional time points beyond the 1-month from time zero data point are expected to provide similar dissolved oxygen levels.

To achieve the above objective, as described herein, numerous aspects for possible oxygen introduction into the L-cysteine composition have been carefully studied and controlled. For example, in some cases, the dissolved oxygen content in the carrier can be reduced to at or below a predetermined level before the L-cysteine is added to the carrier. In some additional examples, reducing a level of dissolved oxygen in the carrier can include blanketing a container for housing the composition in an inert gas, such as nitrogen, argon, or the like, prior to introducing the carrier or composition into the container. In still other examples, reducing a level of dissolved oxygen in the carrier can include bubbling the carrier or composition with an inert gas, such as nitrogen, argon, or the like, at ambient or reduced atmospheric pressure prior to and/or during addition and mixing of L-cysteine. In some examples, reducing a level of dissolved oxygen in the carrier can be performed at an ambient or sub-ambient temperature. It is noted that the reduction of dissolved oxygen in the carrier to at or below a predetermined level can be accomplished without the addition of a supplementary antioxidant, but is not required in the methods and compositions described herein. Thus, the L-cysteine composition for injection is free of a supplementary antioxidant. As described elsewhere herein, attaining low and consistent dissolved oxygen was achieved using the protocol with sampling as set forth in Example 4.

The compositions have long-term stability. Thus, in certain embodiments, the amounts of the components described herein are amounts that are detected after the composition has been in storage. The compositions will have been stored at room temperature for less than a year, or for a year, or for more than a year. Such timelines include, for example, for about 15 months, for about 18 months, for about 24 months. Or, alternatively, the storage time could be for about 9 months, for about 7 months, for about 6 months, for about 5 months, for about 4 months, for about 3 months, for about 2 months, for about 1 month, or for about 3 weeks. Storage conditions are 25° C./60% RH unless otherwise indicated.

Useful concentrations of L-cysteine or a pharmaceutically acceptable salt thereof and/or hydrate thereof in a compositions as described herein include an amount from about 20 mg/mL to about 80 mg/mL, from about 30 mg/mL to about 70 mg/mL, from about 40 mg/mL to about 60 mg/mL, from about 45 mg/mL to about 55 mg/mL, or an amount of about 50 mg/mL, or from about 35 mg/mL to about 50 mg/mL, or an amount of about 37.5 mg/mL. It is noted that the amounts of L-cysteine disclosed herein, whether as a total mass or as a concentration, are based on L-cysteine hydrochloride monohydrate or the free base, as specified. Thus, where other forms of L-cysteine are employed in the composition, the amount of the alternative form included in the composition can be calculated based on an equivalent amount of L-cysteine hydrochloride monohydrate rather than the amount of the alternative form employed.

Thus, the stable L-cysteine composition can comprise total amounts of L-cysteine from about 200 mg to about 4000 mg, or from about 300 mg to about 700 mg, or from about 300 mg to about 400 mg. For example, a 10 mL vial could be manufactured to contain about 350 mg of L-Cysteine. In certain embodiments, the L-cysteine composition can comprise a total amount of L-cysteine from about 1200 mg to about 2000 mg. For example, a 50 mL container could be manufactured to contain about 1800 mg of L-Cysteine. In another embodiment, the total composition of an L-Cysteine composition container may range from about 3000 mg to about 4000 mg. For example, a 100 mL container could be manufactured to contain about 3500 mg of total L-Cysteine.

It has been found that the container in which the compositions are held can affect the level of certain components. In certain embodiments, the L-cysteine composition can be enclosed in a single-use container. The container can have a variety of volumes. Typically, the container can have a volume of from about 10 ml to about 100 ml. In some examples, the container can have a volume of from about 10 ml to about 50 ml. In other examples, the container can have a volume of from about 50 ml to about 100 ml. In still other examples, the container can have a volume of about 10 ml or about 20 ml.

The container can be made of a variety of materials. Non-limiting materials can include glass, a plastic (e.g. polyethylene, polypropylene, polyvinyl chloride, polycarbonate, etc.), the like, or a combination thereof provided that it can both prevent oxygen penetration and minimize Aluminum, heavy metals and anions contamination to the composition. Up to now, there has been no guidance with regard to the compatibility of L-cysteine with coated glass vials or that any vials could be used to provide L-cysteine compositions having low levels of Aluminum.

Another confounding factor is the low pH of the L-Cysteine product, which is less than 3.0 in certain embodiments. This low pH can disrupt the plastic coating or silicon coating inside the glass container and Aluminum, heavy metals and anions could leach during the shelf life of the product, especially over prolonged storage of the product. Therefore, up to now, the success of the product was uncertain until the products described herein were manufactured and studied in real time for prolonged periods as described herein.

It should be recognized that vials which are impermeable with an internal coating, vials which are stored in a pouch that protects the product from atmospheric oxygen ingress, and relatively thick vials made of impermeable plastic or glass can be suitable for the L-Cysteine product disclosed herein.

Vials which are stored in a pouch can be prepared in a similar manner as described herein and then pouched in a plastic material that is then sealed. The pouch may be kept under vacuum or under an inert atmosphere. Methods for manufacturing such pouched products, and materials for such manufacture are known in the industry.

Relatively thick vials made of impermeable plastic are also prepared in a similar manner as described herein. Such vials may be composed of cyclic olefin materials of sufficient thickness to prevent oxygen ingress over a reasonably long period of time, for example 1 month, 2 months, 3 months, 6 months or 12 months. These vials are packaged and supplied as such. Alternatively, these vials can also be pouched as described above in plastic material that is kept under vacuum or under an inert gas atmosphere. It is expected that such pouching extends the shelf life of the product by at least 1 month, or 2 months, or 3 months, or 6 months or longer.

In certain embodiments, the vials are made of glass with an internal coating made of silicon dioxide, for example, Schott Type 1 Plus USP glass. The general thickness of the coating is presumed to be at least 100-200 nanometers thickness. It is believed that this level of thickness was sufficient to provide protection against pH disruption while also preventing the migration of Aluminum from the glass into the L-Cysteine product. Thus, in some specific examples, the container can be an internally coated glass container. In certain other embodiments the glass container is internally coated with silicon dioxide of about 100 to about 200 nanometers.

In certain embodiments the Aluminum contribution from the container may range from about 0.1 ppb to about 200 ppb. In certain other embodiments the Aluminum contribution may range from about 1 ppb to about 150 ppb, from about 1 ppb to about 120 ppb, from about 1 ppb to about 100 ppb, from about 1 ppb to about 80 ppb, from about 1 ppb to about 60 ppb, from about 1 ppb to about 50 ppb, from about 1 ppb to about 40 ppb, from about 1 ppb to about 30 ppb, from about 1 ppb to about 25 ppb, from about 1 ppb to about 20 ppb, from about 1 ppb to about 15 ppb, from about 1 ppb to about 10 ppb, from about 1 ppb to 5 ppb. In certain embodiments, the contribution could be in subranges within the above ranges, for example, from about 35 to 55 ppb, or from about 75 to about 140 ppb, in increments of 5 ppb. All such ranges and subranges are contemplated herein.

The containers are sealed with a suitable stopper made of rubber, elastomeric polymers, or combinations thereof. In certain embodiments the stoppers are coated with a special non-reactive inert coating that minimizes interaction with drug product. For example, some stoppers are coated with Teflon to prevent drug-stopper interactions. One example of a specific coated stopper is supplied by West Pharma and is called V10-F597W Stopper, 20 mm Lyo, 4432/50 Gray, B2-TR Coating, Westar RS. This stopper is a cross-linked mixture of high- and low-molecular weight silicone oils that are cured through the application of UV rays and heat. Because it is a spray-on coating applied to molded closures before the trimming process, B2-Coating can be applied at various levels on the bottom and top of closures. These specific stoppers are preferred even though similar coating materials and methodology applied to other types of stoppers could also work. The stoppers are selected not only for their inertness vis-à-vis the drug product but also for their minimal contribution to Aluminum levels in the drug product.

In certain embodiments the Aluminum contribution from the stopper may range from about 0.1 ppb to about 100 ppb. In certain other embodiments the Aluminum contribution may range from about 1 ppb to about 90 ppb, from about 1 ppb to about 80 ppb, from about 1 ppb to about 70 ppb, from about 1 ppb to about 60 ppb, from about 1 ppb to about 50 ppb, from about 1 ppb to about 40 ppb, from about 1 ppb to about 30 ppb, from about 1 ppb to about 25 ppb, from about 1 ppb to about 20 ppb, from about 1 ppb to about 15 ppb, from about 1 ppb to about 10 ppb, from about 1 ppb to 5 ppb. In certain embodiments, the contribution could be in subranges within the above ranges, for example, from about 35 to 55 ppb, or from about 25 to about 75 ppb, in increments of 5 ppb. All such ranges and subranges are contemplated herein.

In addition to the container and stopper, the drug substance and excipients including water for injection may contribute Aluminum to the drug product. Thus, in one aspect the Aluminum contribution from the drug substance may range from about 0.1 ppb to about 70 ppb. In certain other embodiments the Aluminum contribution may range from about 1 ppb to about 60 ppb, from about 1 ppb to about 50 ppb, from about 1 ppb to about 40 ppb, from about 1 ppb to about 30 ppb, from about 1 ppb to about 25 ppb, from about 1 ppb to about 20 ppb, from about 1 ppb to about 15 ppb, from about 1 ppb to about 10 ppb, from about 1 ppb to 5 ppb. In certain embodiments, the contribution could be in subranges within the above ranges, for example, from about 35 to 55 ppb, or from about 75 to about 140 ppb, in increments of 5 ppb. All such ranges and subranges are contemplated herein.

The water for injection may contribute Aluminum from about 0.1 ppb to about 20 ppb. In certain embodiments the Aluminum contribution may range from about 1 ppb to about 15 ppb, from about 1 ppb to about 12 ppb, from about 1 ppb to about 10 ppb, from about 1 ppb to about 8 ppb, from about 1 ppb to about 6 ppb, from about 1 ppb to about 5 ppb, from about 1 ppb to about 4 ppb, from about 1 ppb to about 3 ppb, from about 1 ppb to about 2.5 ppb, from about 1 ppb to about 2 ppb, from about 1 ppb to about 1.5 ppb. In certain embodiments, the contribution could be in subranges within the above ranges, for example, from about 5 to 7.5 ppb, or from about 10.5 to about 15.0 ppb, in increments of 0.5 ppb. All such ranges and subranges are contemplated herein.

In summary, to lower the Aluminum level to even greater extent as described herein, the container, the stopper, the drug substance, the water for injection, and any other excipients can be chosen such that the Aluminum concentration in the drug product is from about 1.0 ppb to about 250 ppb, or as described in the other embodiments provided herein.

Advantageously, in certain embodiments, the compositions maintain cysteine levels for extended periods, and/or are substantially free or essentially free of cysteine precipitate. However, it is noted that where cysteine is present in the L-cysteine composition it is not necessarily dissolved. For example, in some cases, it can be present in the composition as an undissolved particle.

Where the L-cysteine composition includes cysteine, it can typically be present in relatively small amounts compared to L-cysteine. In certain embodiments, cysteine is present in the composition in an amount not more than 2.0 wt % relative to L-cysteine after storage at ambient temperature for a period of 6 months. In certain embodiments, cysteine is present in the composition in an amount not more than 1.0 wt % relative to L-cysteine after storage at ambient temperature for a period of 6 months. In certain embodiments, cysteine is present in the composition in an amount not more than 0.5 wt % relative to L-cysteine after storage at ambient temperature for a period of 6 months. In certain embodiments, cysteine is present in the composition in an amount not more than 0.4 wt % relative to L-cysteine after storage at ambient temperature for a period of 6 months. In certain embodiments, cysteine is present in the composition in an amount not more than 0.3 wt % relative to L-cysteine after storage at ambient temperature for a period of 6 months. In certain embodiments, cysteine is present in the composition in an amount not more than 0.2 wt % relative to L-cysteine after storage at ambient temperature for a period of 6 months. In certain embodiments, cysteine is present in the composition in an amount not more than 0.1 wt % relative to L-cysteine after storage at ambient temperature for a period of 6 months.

Further, in certain embodiments, cysteine can be present in the L-cysteine composition, but in an amount not more than 2.0 wt % relative to L-cysteine after storage at ambient temperature for a period of 3 months. In certain embodiments, cysteine can be present in the L-cysteine composition, but in an amount not more than 2.0 wt % relative to L-cysteine after storage at ambient temperature for a period of 3 months. In some embodiments, cysteine can be present in the L-cysteine composition in an amount from about 0.001 wt % to about 2.0 wt % relative to the amount of L-cysteine present in the composition. In some embodiments, cysteine can be present in the L-cysteine composition in an amount from about 0.005 wt % to about 0.5 wt % relative to the amount of L-cysteine present in the composition. In some embodiments, cysteine can be present in the L-cysteine composition in an amount from about 0.05 wt % to about 1.0 wt % relative to the amount of L-cysteine present in the composition. In some embodiments, L-cysteine can be present, but in an amount that is either not detectable or that is below a limit of quantitation using a standard testing procedure, such as a validated test method for detecting cysteine.

Advantageously, in certain embodiments, the compositions maintain pyruvic acid levels for extended periods, and/or are substantially free or essentially free of pyruvic acid. When present, pyruvic acid is typically present in a relatively small amount compared to L-cysteine. In certain embodiments, pyruvic acid is present in the composition in an amount not more than 2.0 wt % relative to L-cysteine after storage at ambient temperature for a period of 6 months. In certain embodiments, pyruvic acid is present in the composition in an amount not more than 1.0 wt % relative to L-cysteine after storage at ambient temperature for a period of 6 months. In certain embodiments, pyruvic acid is present in the composition in an amount not more than 0.5 wt % relative to L-cysteine after storage at ambient temperature for a period of 6 months. In certain embodiments, pyruvic acid is present in the composition in an amount not more than 0.4 wt % relative to L-cysteine after storage at ambient temperature for a period of 6 months. In certain embodiments, pyruvic acid is present in the composition in an amount not more than 0.3 wt % relative to L-cysteine after storage at ambient temperature for a period of 6 months. In certain embodiments, pyruvic acid is present in the composition in an amount not more than 0.2 wt % relative to L-cysteine after storage at ambient temperature for a period of 6 months.

In certain embodiments, pyruvic acid is present in the composition in an amount not more than 0.1 wt % relative to L-cysteine after storage at ambient temperature for a period of 6 months. In certain embodiments, pyruvic acid can be present in the L-cysteine composition, but in an amount not more than 2.0 wt % relative to L-cysteine after storage at ambient temperature for a period of 3 months. In certain embodiments, pyruvic acid can be present in the L-cysteine composition, but in an amount not more than 2.0 wt % relative to L-cysteine after storage at ambient temperature for a period of 6 months. In some embodiments, pyruvic acid can be present in the L-cysteine composition in an amount from about 0.001 wt % to about 2.0 wt % relative to the amount of L-cysteine present in the composition. In some embodiments, pyruvic acid can be present in the L-cysteine composition in an amount from about 0.005 wt % to about 0.5 wt % relative to the amount of L-cysteine present in the composition. In some embodiments, pyruvic acid can be present in the L-cysteine composition in an amount from about 0.05 wt % to about 1.0 wt % relative to the amount of L-cysteine present in the composition. In some embodiments, pyruvic acid can be present, but in an amount that is either not detectable or that is below a limit of quantitation using a standard testing procedure, such as a validated test method for detecting pyruvic acid.

As discussed above, to achieve safe method and compositions, it is beneficial to further understand which other components are present beyond Aluminum and pyruvic acid, and control their amounts as well. Because preterm infants could be exposed to L-Cysteine for potentially longer periods, and their main source of L-Cysteine is through parenteral administration, careful consideration should be given to exposure to other potentially unsafe compounds that may leach out of the container or stopper in amounts greater than what are considered safe limits. Examples include certain volatile compounds, certain heavy elements, and certain anions.

Daily acceptable limits are known for these potentially unsafe compounds. However, because the L-Cysteine Injection is used to infuse into preterm and term infants and those elderly that are critically ill will compromised renal functions, and sometimes for periods that exceed more than a few days, just meeting the daily acceptable limits may not be sufficient. Every effort must be made to reduce the levels to as low as practicable. The L-Cysteine compositions presented herein provide in some embodiments about one-half of the daily acceptable limits; in some embodiments, about one-fourth of the daily acceptable limits; in some embodiments, about one-fifth of the daily acceptable limits; in some embodiments, about one-sixth of the daily acceptable limits.

The anions that are desirable to control are: Iodide and Fluoride. The acceptable limit for Iodide is about 20 ppm or less. The acceptable limit for Fluoride is about 30 ppm or less. The L-Cysteine compositions provided herein show Iodide concentrations of less 20 ppm and Fluoride concentrations of less than 30 ppm when measured at any time from the day of manufacture through its shelf-life of 6 months, or 12 months, or 18 months, or 24 months, when stored under Room Temperature Conditions. In some embodiments, the L-Cysteine compositions provide from about 1.0 ppm to 20 ppm of Iodide; in some embodiments, from about 1.0 ppm to about 15 ppm; in some embodiments, from about 1.0 ppm to about 10 ppm; and in some embodiments, from about 1.0 ppm to about 5 ppm. In some embodiments, the L-Cysteine compositions provide from about 1.0 ppm to 20 ppm of Fluoride; in some embodiments, from about 1.0 ppm to about 15 ppm; in some embodiments, from about 1.0 ppm to about 10 ppm; and in some embodiments, from about 1.0 ppm to about 5 ppm. Methods for evaluating the anions and the results are provided in Example 8.

As noted above, several elements may leach or be extracted out into the L-Cysteine drug product, thereby presenting a potential safety/toxicity concern to subjects that require L-Cysteine parenteral administration. Art-known methods may be used to evaluate the elemental levels. Inductively-coupled plasma mass spectral method is one such highly specific method. Example 9 provides the data generated by using ICP-MS technique. As shown in Example 9, there are over thirty elements that are generally known to present safety/toxicity concerns. The Table 22 provides the daily allowable limit for all of these elements, and the observed levels in the present L-Cysteine compositions. The daily allowable limit for some elements are relatively high, whereas for other elements they are relatively very low. For example, Molybdynum has the level of 14,500 ppb approximately, whereas Cadmium has about 19 ppb.

For purposes of monitoring the L-Cysteine compositions for the elements of concern, in one aspect, the levels of Mercury, Lead, Nickel and Arsenic are of significance. Therefore, in one aspect, the L-Cysteine compositions presented herein have further improved safety because they provide these elements at amounts far less than the daily allowable limits. Targeted daily allowable limits include 48 ppb for Lead, 29 ppb for Mercury, 194 ppb for Nickel, and 174 ppb for Arsenic.

The L-Cysteine compositions described herein provide from about 1 ppb to 10 ppb of Lead; in some embodiments, from about 1 ppb to about 8 ppb; in some embodiments, from about 1 ppb to about 7 ppb; or in some embodiments, from about 1 ppb to about 5 ppb. when measured at any time from the day of manufacture through its shelf-life of 6 months, or 12 months, or 18 months, or 24 months, when stored under Room Temperature Conditions.

With respect to Mercury, the L-Cysteine compositions described herein provide from about 0.1 ppb to 10 ppb of Mercury; in some embodiments, from about 0.1 ppb to about 8 ppb; in some embodiments, from about 0.1 ppb to about 7 ppb; or in some embodiments, from about 0.1 ppb to about 5 ppb. when measured at any time from the day of manufacture through its shelf-life of 6 months, or 12 months, or 18 months, or 24 months, when stored under Room Temperature Conditions.

With respect to Nickel, the L-Cysteine compositions described herein provide from about 1 ppb to 50 ppb of Nickel; in some embodiments, from about 1 ppb to about 40 ppb; in some embodiments, from about 1 ppb to about 30 ppb; or in some embodiments, from about 1 ppb to about 25 ppb; or in some embodiments from about 1 ppb to about 20 ppb, when measured at any time from the day of manufacture through its shelf-life of 6 months, or 12 months, or 18 months, or 24 months, when stored under Room Temperature Conditions.

With respect to Arsenic, the L-Cysteine compositions described herein provide from about 0.1 ppb to 60 ppb of Arsenic; in some embodiments, from about 0.1 ppb to about 50 ppb; in some embodiments, from about 0.1 ppb to about 40 ppb; in some embodiments, from about 0.1 ppb to about 30 ppb; in some embodiments, from about 0.1 ppb to about 25 ppb; or in some embodiments from about 0.1 ppb to about 20 ppb; in some embodiments, from about 0.1 ppb to about 15 ppb; in some embodiments, from about 0.1 ppb to about 10 ppb; or in some embodiments, from about 0.1 ppb to about 5.0 ppb, when measured at any time from the day of manufacture through its shelf-life of 6 months, or 12 months, or 18 months, or 24 months, when stored under Room Temperature Conditions.

In some embodiments, the Arsenic, Mercury, Lead and other elements may be extracted from the container or from the stopper. In one specific embodiment, the extracted out amount of Arsenic, Mercury, Lead, and Nickel combined from the stopper is 100 ppb or less. In other embodiments, the extracted amount of Arsenic, Mercury, Lead, and Nickel combined from the stopper is from about 10 to about 50 or from about 10 to about 100 ppb.

It should be recognized that in some instances the amount of a specific element present in the L-Cysteine compositions described herein may be below the Limit of Quantitation (LOQ). In those instances, for purposes of this disclosure and claims made herein, the compositions may be considered to contain the lowest level described in the preceding paragraphs. For example, when Arsenic is determined to be below the LOQ, the Arsenic amount may be considered to be at 0.1 ppb. Therefore, all such instances where the compositions show amounts below the LOQ are within the contemplation of this disclosure.

In certain embodiments, the compositions further comprise within the container, headspace gas that includes oxygen in an amount of from about 0.5% v/v to about 5.0% v/v, or from about 0.5% v/v to about 4.0% v/v, or from about 0.5% v/v to about 3.5% v/v, from about 0.5% v/v to about 3.0% v/v, or from about 0.5% v/v to about 2.5% v/v, or from about 0.5% v/v to about 2.0% v/v, or from about 0.5% v/v to about 1.5% v/v, or from about 0.5% v/v to about 1.0% v/v, or in some cases from about 0.1% v/v to about 0.5% v/v, or from about 0.1% v/v to about 0.4% v/v, or from about 0.1% v/v to about 0.3% v/v, or from about 0.1% v/v to about 0.2% v/v. For the sake of clarity and the ease of discussion and measurement, these values are taken for the L-Cysteine composition at the time of its manufacture ("tine zero" data point), or during and up to 1 month from time zero. Additional time points beyond the 1-month from time zero data point may provide similar headspace oxygen levels.

Without wishing to be bound by theory, the dissolved oxygen levels and the head space oxygen levels within a sealed container of L-Cysteine compositions described herein may reach an equilibrium at some time point during its shelf-life. Such equilibrium may be maintained for a very short time, i.e., for a few seconds, or for a very long time, i.e., for several months. Such equilibrium may on occasion be disturbed by simple agitation. Therefore, it should be recognized that dissolved oxygen levels and headspace oxygen levels may fluctuate from one time point to another in terms of absolute numbers. However, the numbers are expected to stay within the ranges disclosed herein. Occasionally, one number (e.g., dissolved oxygen) may exceed or fall out of a certain range (e.g., from about 05 to about 3.0 PPM) at a 15-day time point, but may fall within that range at some other time point (e.g., 30 day time point, or later). Therefore, in some aspects, the ranges, subranges, and specific data points disclosed and discussed herein are valid and suitable for time points beyond the time zero and 1-month time points. In one aspect, the time points could be extended to 2-months, 3-months, 6-months, 9-months, 12-months, 15-months, 18-months, and 24 months.

In some aspects, the total amount of oxygen in the sealed container may be an appropriate measure to evaluate the stability of the L-Cysteine compositions herein. For example, the total amount of oxygen within the container may be arrived at by adding up the amount of dissolved oxygen in the carrier and the amount of head space oxygen. These values can also be expressed independently in separate units (i.e., dissolved oxygen as ppm and head space oxygen as % v/v). An example would be an L-Cysteine composition that contains a dissolved oxygen level of from about 0.1 ppm to 4.0 ppm and a head space oxygen level of about 0.5% v/v to about 4.0% v/v.

The amount of oxygen present in the headspace of the container can be controlled by filling the headspace with an inert gas, such as nitrogen or argon. Alternatively, the head space oxygen may be controlled by vacuum operation without using an inert gas. In another aspect, the head space oxygen may be controlled by a combination of vacuum operation and inert gas overlay. In one particular aspect, the head space oxygen is controlled by repeated pulses of vacuum and inert gas overlay in tandem such that the process may start first with vacuum operation followed by inert gas overlay followed by vacuum operation. The combination of vacuum operation and inert gas overlay (or inert gas overlay and vacuum operation) is considered one pulse when both steps are used together. A typical head space control operation may comprise from one to eight pulses. Typically, there could be two, three, four, or five pulses. Each pulse could last from about one tenth of one second to five seconds or from five to fifteen seconds when conducted by automated high-speed equipment custom designed for this specific purpose. In some embodiments, the pulse may last from about 0.1 to about 2.0 seconds. In some embodiments, the pulse may last from about 0.1 to about 1.0 seconds, or from about 0.1 to about 0.4 seconds. When done using manual methods, each pulse could take up to 30-60 seconds or longer. Such a manual process is described in more detail in Examples 1 and 4. Alternatively, a more automated process that was developed by the current inventors is described in Example 5.

In certain embodiments, the compositions are part of a total parenteral nutrition regimen. The L-cysteine compositions described herein can be admixed with amino acid solutions, such as crystalline amino acid injection, for example, commercially available TRAVASOL® and TRAVASOL E®.

In certain aspects, the subject matter described herein is directed to a safe, stable composition from about 100 mL to about 1000 mL for administration via a parenteral infusion within about 24 to about 48 hours of admixture, comprising a mixture of a composition of L-Cysteine described herein; and an amino acid composition that is essentially free of L-Cysteine comprising one or more amino acids selected from the group consisting of: leucine, isoleucine, lysine, valine, phenylalanine, histidine, threonine, methionine, tryptophan, alanine, arginine, glycine, proline, serine, and tyrosine.

In certain embodiments, the subject matter described herein is directed to a stable TPN composition for infusion, comprising:

L-cysteine or a pharmaceutically acceptable salt thereof and/or hydrate thereof;

Aluminum in an amount from about 10 parts per billion (ppb) to about 80 ppb;

cysteine in an amount from about 0.001 wt % to about 2.0 wt % relative to L-cysteine;

pyruvic acid in an amount from about 0.001 wt % to about 2.0 wt % relative to L-cysteine;

one or more amino acids selected from the group consisting of: leucine, isoleucine, lysine, valine, phenylalanine, histidine, threonine, methionine, tryptophan, alanine, arginine, glycine, proline, serine, and tyrosine;

a pharmaceutically acceptable carrier, comprising water, wherein, the amounts are from about 100 mL to about 1,000 mL and the total aluminum delivered by the said composition does not exceed about 4-5 mcg/kg/day. In certain embodiments, the amounts include 150 mL, 200 mL, 250 mL, 300 mL, 350 mL, 400 mL, 450 mL, 500 mL, 550 mL, 600 mL, 650 mL, 700 mL, 750 mL, 800 mL, 850 mL, 900 mL and 950 mL.

In certain embodiments, the stable composition for infusion comprises one or more amino acids selected from the group consisting of leucine, isoleucine, lysine, valine, phenylalanine, histidine, threonine, methionine, tryptophan, alanine, arginine, glycine, proline, serine, and tyrosine. In certain embodiments, the composition includes all of these. In certain embodiments, 500 mg of L-Cysteine is admixed with 12.5 gram of crystalline amino acid injection, such as that present in 250 mL of 5% crystalline amino acid injection. In some aspects, 15 mg of L-Cysteine is admixed with one gram of amino acids. In some other aspect, 40 mg of L-Cysteine is admixed with one gram of amino acids. Depending on the needs of the subject, based on specific characteristics such as age, weight, and physiological factors such as renal function, the dose may be adjusted at or within these ranges of 15-40 mg of L-Cysteine per gram of amino acids. See, for example, Tables 1-2 above. Thus, the pharmaceutical compositions comprising L-Cysteine can be formulated, dosed and administered in a fashion, i.e., amounts, concentrations, schedules, course, and vehicles, consistent with good medical practice. The "therapeutically and nutritionally effective amount" of the compound to be administered will be governed by such considerations.

In certain embodiments, the compositions are essentially free of supplementary antioxidant. As used herein, this refers to the absence of any substance that is added to the compositions specifically as an antioxidant. Naturally occurring antioxidants may still be present.

In certain embodiments, the compositions that comprise one or more of the above amino acids are essentially free of dextrose. However, in certain embodiments, the compositions that comprise one or more of the above amino acids further comprise a sugar.

In certain embodiments, the pH of the compositions is about 1.0 to about 2.5, or about 1.6 to about 2.0, or about 1.6, or about 1.7, or about 1.8, or about 1.9 or about 2.0. For administration, the pH is generally adjusted by admixing with other components to a pH of about 6.0 to about 8.0, but generally around 7.0. In certain embodiments, the compositions are essentially free of a buffer. In certain embodiments, the compositions further comprise a buffer.

In particular embodiments, the subject matter described herein is directed to a stable L-cysteine composition for injection that can be useful for treatment of a variety of conditions, such as those described above. In further detail, L-cysteine can be administered in a variety of forms, such as the free base, L-cysteine hydrochloride, a pharmaceutically acceptable salt thereof (e.g. sodium salt, calcium salt, etc.), a hydrate thereof, the like, or a combination thereof. In some specific examples, L-cysteine can be included in the L-cysteine composition for injection as L-cysteine hydrochloride monohydrate.

In particular embodiments, the subject matter described herein is directed to a stable L-cysteine composition for injection, comprising:
about 34.5 mg/mL of L-cysteine free base, or a pharmaceutically acceptable salt thereof and/or hydrate thereof;
Aluminum in an amount of 130 ppb or below;
water;
wherein the composition is enclosed in a single-use container having a volume of from 10 mL to 100 mL, and is stable for 9 months or less.

In certain embodiments, the stable, safe L-cysteine composition can consist essentially of L-cysteine, water, Aluminum in an amount of less than 200 ppb, cysteine in an amount from about 0.001 wt % to about 2 wt % relative to L-cysteine, pyruvic acid in an amount from about 0.001 wt % to about 2 wt % to L-cysteine, headspace oxygen that is less than 4.0% and dissolved oxygen from about 0.1 ppm to about 1 ppm. Other trace components or excipients do not materially affect the basic and novel characteristics of composition unless otherwise indicated, for example, undesirable anions and heavy metals.

The pharmaceutical composition (or formulation) for application may be packaged in a variety of ways depending upon the method used for administering the drug. Generally, an article for distribution includes a container having deposited therein the pharmaceutical formulation in an appropriate form. The container may also include a tamper-proof assemblage to prevent indiscreet access to the contents of the package. In addition, the container has deposited thereon a label that describes the contents of the container. The label may also include appropriate warnings, more specifically about the Aluminum content of the L-Cysteine composition. For example, the label may indicate that the Aluminum in the container may be at 100 ppb or 100 mcg/L. In another embodiment, the label may indicate that the Aluminum in the container may be at 120 ppb or 120 mcg/L. In some specific embodiments, the Aluminum level may be described as not more than 120 ppb, or not more than 120 mcg/L, or NMT 120 ppb, or NMT 120 mcg/L. In addition to the label, the labeling associated with the L-Cysteine product may have the same description of Aluminum.

It should be understood that, as is customary in the pharmaceutical arts, the phrases "NMT" or "not more than" represents the upper limit, but also is understood not to mean that the value is zero or even can be zero. For example, a statement that the Aluminum levels are NMT 120 ppb is not understood by the practitioners in the art that the Aluminum levels are at zero ppb in that particular vial bearing that label. Pharmacists and other health care professionals instead would interpret for purposes of calculating the Aluminum content of a TPN preparation using that specific L-Cysteine vial that the Aluminum levels are at 120 ppb so that, even if the actual amount is lower than the 120 ppb in the product, they err on the conservative side. This is the custom in the pharmaceutical industry developed and practiced to safeguard the health of patients. If indeed the label is intended to convey with certainty that the actual Aluminum level is zero ppb, the label then would state that fact or indicate that the product is free of Aluminum.

Similarly, any numerical value expressed as "less than" is intended to convey that the value is below that certain numerical value, including, as the case may be zero. For example, when it is stated herein that Aluminum levels are less than about 20 ppb, it is understood that in some embodiments the Aluminum can be, but not necessarily in all cases, anywhere from zero to about 19 ppb. It is also understood that this may, but not necessarily in all cases, encompass those situations where the levels are below quantitation limit, but the presence of Aluminum is detectable. In those cases where the Aluminum (or any other measured material generally) where the material is detectable but is below the level of quantitation, that numerical value can be considered for example as being about 1.0 (for Aluminum) or 0.001 (for Cystine or Pyruvic acid), or 1.0 ppb (for elements) or 1.0 ppm (for iodide or fluoride). Unless an actual analysis is made of the product and a specific number is determined, there is no certainty of the actual value. The US FDA does not require this precision in the labeling on a product-by-product or even batch-by-batch because that is impracticable in a commercial supply chain setting for drug products.

Thus, the phrases "NMT" or "not more than" or "less than" are terms of art in the pharmaceutical industry. Those in the industry do not assume these terms necessarily represent zero in all cases, even though that is a possibility. When calculating the Aluminum amounts for purposes of preparing parenteral nutrition products the artisan never assumes the Aluminum levels are zero in order to safeguard the patient health. Accordingly, this present disclosure and the claims derived therefrom are to be read and understood in light of this custom and practice in the art.

As mentioned above, the L-cysteine compositions for infusion may optionally be mixed with pharmaceutically acceptable excipients, also described in *Remington's Pharmaceutical Sciences* (1980) 16$^{th}$ edition, Osol, A. Ed., Mack Publishing Co., Easton, Pa.

As noted above, the diluted L-cysteine composition for infusion can typically have a pH of from about 5.0 to about 8.0, or from about 6.0 to about 7.0. However, dilution and administration of the L-cysteine composition for infusion will typically be overseen by a licensed medical professional, who may recommend a pH outside of the ranges recited herein under certain circumstances. Additionally, the diluted L-cysteine composition for infusion can typically have a tonicity of from about 250 milliosmoles/liter (mOsmol/L) to about 1,000 mOsmol/L, or more, or of from about 350 mOsmol/L to about 475 mOsmol/L. However, dilution and administration of the L-cysteine composition for infusion will typically be overseen by a licensed medical professional, who may recommend a tonicity outside of the ranges recited herein under certain circumstances.

III. Methods

The subject matter described herein is directed to methods of treating a subject having an adverse health condition that is responsive to L-cysteine administration. The methods can include diluting the stable L-cysteine composition described herein with an intravenous fluid to prepare a diluted L-cysteine composition for infusion. The methods can further include parenterally administering the diluted L-cysteine composition to provide a therapeutically effective dose of L-cysteine or a pharmaceutically acceptable salt thereof and/or hydrate thereof to the subject in a therapeutically effective dosing regimen.

In certain embodiments, the subject matter described herein is directed to a method of reducing Aluminum administration from a total parenteral nutrition regimen comprising L-cysteine, the method comprising, mixing a composition comprising L-cysteine or a pharmaceutically acceptable salt thereof and/or hydrate thereof comprising:

Aluminum in an amount from about 1.0 parts per billion (ppb) to about 250 ppb or from about 10 ppb to about 80 ppb;

L-cysteine in an amount from about 0.001 wt % to about 2.0 wt % relative to L-cysteine; and pyruvic acid in an amount from about 0.001 wt % to about 2.0 wt % relative to L-cysteine;

with a composition comprising one or more amino acids selected from the group consisting of: leucine, isoleucine, lysine, valine, phenylalanine, histidine, threonine, methionine, tryptophan, alanine, arginine, glycine, proline, serine, and tyrosine; and a pharmaceutically acceptable carrier, comprising water, to form a composition for infusion of about 100 mL to about 1000 mL, wherein the Aluminum provided in said parenteral nutrition regimen is from about 1-2 to about 4-5 micrograms/kg/day.

In certain aspects, the compositions and methods described herein are directed to methods of administering L-Cysteine together with a composition for parenteral nutrition, comprising:

diluting a stable L-cysteine composition for injection as described herein with a parenteral nutrition composition to form a mixture; and parenterally administering the mixture to a subject in need thereof in a therapeutically and/or nutritionally effective dose. In one aspect, the subject is a neonatal weighing less than 2 kilos. In another aspect, the subject is a pediatric patient that is from about 0.2 kilos to about 20 kilos. In another aspect, the subject is an adult requiring parenteral nutrition.

In certain embodiments, the subject matter described herein is directed to a method of reducing Aluminum administration from a parenteral nutrition regimen comprising L-cysteine, comprising:

administering to a subject a composition comprising L-cysteine or a pharmaceutically acceptable salt thereof and/or hydrate thereof;

Aluminum in an amount from about 10.0 parts per billion (ppb) to about 250 ppb, or from about 10 ppb to about 80 ppb;

cysteine in an amount from about 0.01 wt % to about 2.0 wt % relative to L-cysteine;

pyruvic acid in an amount from about 0.01 wt % to about 2.0 wt % relative to L-cysteine;

one or more amino acids selected from the group consisting of: leucine, isoleucine, lysine, valine, phenylalanine, histidine, threonine, methionine, tryptophan, alanine, arginine, glycine, proline, serine, and tyrosine, a pharmaceutically acceptable carrier, comprising water, wherein, the amounts are about 100 mL to about 1,000 mL, wherein the Aluminum administered to said subject is reduced compared to administration of a standard parenteral composition comprising L-cysteine and Aluminum at a range of from about 900 ppb to about 5,000 ppb.

In certain embodiments, the methods provide that the reduction in the amount of Aluminum administered is relative to the amount of Aluminum in a L-cysteine injection composition having more than 500 ppb Aluminum, or more than 250 ppb Aluminum. The relative reduction in Aluminum can be up to 90%, up to 80%, up to 70%, up to 60%, up to 50%, up to 40%, up to 30%, up to 20%, up to 10%, or up to 5%, as compared to the amount of Aluminum administered with a L-cysteine composition having more than 500 ppb Aluminum, or more than 250 ppb Aluminum. In certain embodiments, the reduction occurs over the span of a day, a week, a month or the duration of the TPN regimen.

In certain aspects, the subject matter described herein is directed to methods of treating a subject having an adverse health condition that is responsive to L-cysteine administration, comprising:

diluting a stable L-cysteine composition as described herein with an intravenous fluid to prepare a diluted L-cysteine composition for infusion; and infusing the diluted L-cysteine composition for infusion to a subject to provide a therapeutically effective dose of L-cysteine or a pharmaceutically acceptable salt thereof and/or hydrate thereof to the subject in a therapeutically effective dosing regimen.

In certain embodiments, the method of treating a subject having an adverse health condition that is responsive to L-cysteine administration further comprises, before the diluting step, admixing the stable L-cysteine composition with an amino acid solution, such as, crystalline amino acid injection. In this aspect, the methods comprise diluting with an intravenous fluid the stable L-cysteine composition admixed with an amino acid solution, wherein the fluid comprises dextrose.

In certain embodiments, the adverse health condition is the lack of a necessary enzyme in the trans-sulfuration pathway that converts methionine to L-cysteine. Other adverse health conditions include inadequate absorption resulting from short bowel syndrome; gastrointestinal fistula; bowel obstruction; prolonged bowel rest; severe malnutrition; significant weight loss and/or hypoproteinaemia when enteral therapy is not possible; other disease states or conditions in which oral or enteral feeding are not an option.

For most preterm infants, the administration should be considered as a short-term bridge to provide nutritional support until full enteral nutrition can be provided. Such instances include: Immediately after birth, to provide essential nutrition as enteral feeds are commenced and advanced, and/or during periods of acute gastrointestinal malfunction (eg, due to septic ileus or necrotizing enterocolitis).

In certain embodiments, the administering is a single daily dose, or multiple daily doses, or is administered in accordance with a TPN regimen, for example, the dosing can be over a day, several days, a week or several weeks, a month or several months.

In certain embodiments, the subject is an infant or preterm infant from newborn until about 6 months of age. As presented in Tables 1 and 2 above, the subjects can be from a pre-term infant to an adult that is in need of L-Cysteine supplementation. Thus, the subject can be a subject "in need of" the methods of described herein, for example, in need of the therapeutic effects or prophylactic benefits of the methods. In certain embodiments, the subject is a subject in need of a total parenteral nutrition (TPN) regimen.

In certain embodiments, the intravenous fluid is selected from the group consisting of isotonic saline, glucose solution, glucose saline, dextrose solution, crystalline amino acid solution, lipids, and combinations thereof.

In certain embodiments, the L-cysteine is L-cysteine hydrochloride monohydrate.

In certain embodiments, the diluted L-cysteine composition for infusion is typically administered via intravenous infusion. The selection of administration rate and site of infusion (i.e., via a peripheral or central vein) are within the ordinary skill in the art of medicine, pharmaceutical, nursing, and nutritional sciences.

The diluted L-cysteine composition for infusion can be administered until a therapeutically effective dose is achieved. In some examples, a therapeutically effective dose of L-cysteine or a pharmaceutically acceptable salt thereof and/or hydrate thereof can be from about 0.01 mg to about 2.0 mg L-cysteine. Again, therapeutically effective doses can depend on whether the patient is a pediatric patient or an adult patient. For example, for preterm or term infants less than 1 month of age, the therapeutically effective dose is about 45 to 60 mcg/kg/day. For pediatric patients 1 month to less than 1 year of age, the therapeutically effective dose is 30 to 45 mcg/kg/day. For pediatric patients 1 year to 11 years of age, the therapeutically effective dose is about 15 to 30 mcg/kg/day. For pediatric patients 12 years to 17 years of age, the therapeutically effective dose is about 4 to 7.5 mcg/kg/day. For adults, i.e., stable patients, the therapeutically effective dose is 4 to 5 mcg/kg/day. For adults that are critically ill, the therapeutically effective dose is 7.5 to 10 mcg/kg/day.

The number of doses given daily can vary as desired or needed per the therapeutically effective dosing regimen. In some examples, the therapeutically effective dosing regimen can include daily administration of the diluted L-cysteine composition. In other examples, the therapeutically effective dosing regimen can include twice-daily administration of the diluted L-cysteine composition. In some further examples, the therapeutically effective dosing regimen can provide less than or equal to 5 μg/kg/d of Aluminum. In still further examples, the therapeutically effective dosing regimen can provide less than or equal to 4 μg/kg/d of Aluminum, or less than or equal to 3 μg/kg/d of Aluminum. In certain embodiments, the methods result in a daily dosage of Aluminum from the composition of from about 2 μg/kg/d to not more than 5 μg/kg/d.

The diluted L-cysteine composition for infusion can be administered for the treatment of a number of conditions. For example, L-cysteine can be administered to meet the intravenous amino acid nutritional requirements of individuals (e.g. infants) receiving total parenteral nutrition. As such, in some examples, the subject can be a subject in need of total parenteral nutrition (TPN). In some additional examples, L-cysteine can be administered for the treatment of osteoarthritis, rheumatoid arthritis, angina, chronic bronchitis, chronic obstructive pulmonary disease (COPD), influenza, acute respiratory distress syndrome (ARDS), diabetes (e.g. type 2 diabetes), the like, or a combination thereof.

In certain embodiments, the subject matter described herein is directed to methods of preparing a composition, comprising:
Stirring Water for Injection, USP (WFI) in a vessel at a temperature of NMT about 60° C.;
Contacting the stirring WFI with Argon until the dissolved oxygen is NMT 1 ppm;
Allowing the vessel to cool to a temperature of NMT 30° C.;
Contacting under the Argon the WFI with L-Cysteine Hydrochloride, Monohydrate, USP (L-Cysteine) for NLT about 15 mins;
Continuing the mixing under Argon until the dissolved oxygen is NMT 1 ppm;
Adjusting the pH to about 1.8 with concentrated Hydrochloric Acid, NF and/or 5.0 N Sodium Hydroxide, NF;
Mixing for a minimum of about 10 minutes;
Capping the vessel under Argon and allowing to stand;
Filling said mixed liquid into individual single use containers;
Reducing head space oxygen to about 5.0% to 0.5% and sealing said containers wherein the dissolved oxygen in the container is about 0.1 ppm to about 5 ppm.

The subject matter described herein includes, but is not limited to, the following specific embodiments:

1. A stable L-cysteine composition for parenteral administration, comprising:
L-cysteine or a pharmaceutically acceptable salt thereof and/or hydrate thereof in an amount from about 10 mg/mL to about 100 mg/mL;
Aluminum (Al) in an amount from about 1.0 parts per billion (ppb) to about 250 ppb;
L-cysteine in an amount from about 0.001 wt % to about 2.0 wt % relative to L-cysteine;
pyruvic acid in an amount from about 0.001 wt % to about 2.0 wt % relative to L-cysteine;
a pharmaceutically acceptable carrier, comprising water;
headspace $O_2$ that is from about 0.5% to 4.0% from the time of manufacture to about 1 month from manufacture when stored at room temperature;
dissolved oxygen present in the carrier in an amount from about 0.1 parts per million (ppm) to about 5 ppm from the time of manufacture to about 1 month from manufacture when stored at room temperature,
wherein the composition is enclosed in a single-use container having a volume of from about 10 mL to about 100 mL.

2. The composition of embodiment 1, wherein the composition is essentially free of an antioxidant.

3. The composition of embodiment 1 or 2, wherein said Aluminum is present in an amount from about 1.0 ppb to about 200 ppb.

4. The composition of embodiment 1, 2 or 3, wherein said Aluminum is present in an amount from about 1.0 ppb to about 180 ppb.

5. The composition of embodiment 1, 2, 3 or 4, wherein said Aluminum is present in an amount from about 1.0 ppb to about 170 ppb.

6. The composition of embodiment 1, 2, 3, or 5, wherein said Aluminum is present in an amount from about 1.0 ppb to about 160 ppb.

7. The composition of embodiment 1, 2, 3, 4, 5 or 6, wherein said Aluminum is present in an amount from about 1.0 ppb to about 150 ppb.

8. The composition of embodiment 1, 2, 3, 4, 5, 6 or 7, wherein said Aluminum is present in an amount from about 1.0 ppb to about 130 ppb.

9. The composition of embodiment 1, 2, 3, 4, 5, 6, 7 or 8, wherein said Aluminum is present in an amount from about 1.0 ppb to about 100 ppb.

10. The composition of embodiment 1, 2, 3, 4, 5, 6, 7, 8, 9 or 10, wherein said Aluminum is present in an amount from about 1.0 ppb to about 50 ppb.

11. The composition of embodiment 1, 2, 3, 4, 5, 6, 7, 8, 9, 10 or 11, wherein said Aluminum is present in an amount from about 1.0 ppb to about 20 ppb or from about 1.0 ppb to about 10 ppb.

12. The composition of embodiment 1, 2, 3, 4, 5, 6, 7, 8, 9, 10 or 11, further comprising one or more heavy metals selected from the group consisting of Lead (in an amount of from about 1 ppb to about 10 ppb), Nickel (in an amount of from about 5 ppb to about 40 ppb), Arsenic (in an amount of from about 0.1 ppb to about 10 ppb), and Mercury (in an amount of from about 0.2 ppb to about 5.0 ppb).

13. The composition of embodiment 1, 2, 3, 4, 5, 6, 7, 8, 9, 10, 11 or 12, wherein said heavy metals are present in total in an amount from about 2.0 ppb to about 8.0 ppb.

14. The composition of embodiment 1, 2, 3, 4, 5, 6, 7, 8, 9, 10, 11, 12 or 13, further comprising iodide and fluoride, each present in an amount from about 0.1 ppm to about 20 ppm.

15. The composition of embodiment 14, wherein said ions are present in total an amount from about 2.8 ppm to about 5.8 ppm.

16. The composition of embodiment 1, 2, 3, 4, 5, 6, 7, 8, 9, 10, 11, 12, 13, 14 or 15, wherein said dissolved oxygen is present in an amount from about 0.1 ppm to about 5 ppm.

17. The composition of embodiment 1, 2, 3, 4, 5, 6, 7, 8, 9, 10, 11, 12, 13, 14, 15 or 16, wherein said dissolved oxygen is present in an amount from about 0.1 ppm to about 3 ppm.

18. The composition of embodiment 1, 2, 3, 4, 5, 6, 7, 8, 9, 10, 11, 12, 13, 14, 15, 16 or 17, wherein said dissolved oxygen is present in an amount from about 0.10 ppm to about 2.0 ppm.

19. The composition of embodiment 1, 2, 3, 4, 5, 6, 7, 8, 9, 10, 11, 12, 13, 14, 15, 16, 17 or 18, wherein said dissolved oxygen is present in an amount from about 0.1 ppm to about 1.0 ppm.

20. The composition of embodiment 1, 2, 3, 4, 5, 6, 7, 8, 9, 10, 11, 12, 13, 14, 15, 16, 17, 18 or 19, wherein the composition has been stored at room temperature.

21. The composition of embodiment 1, 2, 3, 4, 5, 6, 7, 8, 9, 10, 11, 12, 13, 14, 15, 16, 17, 18, 19 or 20, wherein the storage is for 1 year or less.

22. The composition of embodiment 1, 2, 3, 4, 5, 6, 7, 8, 9, 10, 11, 12, 13, 14, 15, 16, 17, 18, 19, 20 or 21, wherein the storage is for about 9 months.

23. The composition of embodiment 1, 2, 3, 4, 5, 6, 7, 8, 9, 10, 11, 12, 13, 14, 15, 16, 17, 18, 19, 20, 21 or 22, wherein L-cysteine or a pharmaceutically acceptable salt thereof and/or hydrate thereof is present in the composition in an amount from about 20 mg/mL to about 70 mg/mL.

24. The composition of embodiment 1, 2, 3, 4, 5, 6, 7, 8, 9, 10, 11, 12, 13, 14, 15, 16, 17, 18, 19, 20, 21, 22 or 23, wherein L-cysteine or a pharmaceutically acceptable salt thereof and/or hydrate thereof is present in the composition in an amount of about 50 mg/mL.

25. The composition of embodiment 1, 2, 3, 4, 5, 6, 7, 8, 9, 10, 11, 12, 13, 14, 15, 16, 17, 18, 19, 20, 21, 22, 23 or 24, wherein the container is an internally coated glass container.

26. The composition of embodiment 1, 2, 3, 4, 5, 6, 7, 8, 9, 10, 11, 12, 13, 14, 15, 16, 17, 18, 19, 20, 21, 22, 23, 24 or 25, wherein said internally coated glass container is coated with SiO2.

27. The composition of embodiment 1, 2, 3, 4, 5, 6, 7, 8, 9, 10, 11, 12, 13, 14, 15, 16, 17, 18, 19, 20, 21, 22, 23, 24, 25 or 26, essentially free of cysteine precipitate.

28. The composition of embodiment 1, 2, 3, 4, 5, 6, 7, 8, 9, 10, 11, 12, 13, 14, 15, 16, 17, 18, 19, 20, 21, 22, 23, 24, 25, 26 or 27, wherein said L-cysteine is present in an amount of about 37.5 mg/mL as free base, or a pharmaceutically acceptable salt thereof and/or hydrate thereof.

29. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, wherein the Aluminum is present in the composition in an amount not more than 200 ppb after storage at ambient temperature for a period of 3 months or less, said Aluminum comprising, from about 1.0 ppb to about 100 ppb of Aluminum from the container, from about 1.0 ppb to about 100 ppb of Aluminum from stopper for the container, from about 1.0 ppb to about 100 ppm of Aluminum from the L-cysteine, and from about 1.0 ppb to about 20 ppb of Aluminum from the water.

30. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, wherein the Aluminum is present in the composition in an amount not more than 200 ppb after storage at ambient temperature for a period of 6 months or less, said Aluminum comprising, from about 0 ppb to about 100 ppb of Aluminum from the container, from about 1.0 ppb to about 100 ppb of Aluminum from stopper for the container, from about 1.0 ppb to about 100 ppm of Aluminum from the L-cysteine, and from about 0 ppb to about 20 ppb of Aluminum from the water.

31. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, wherein the Aluminum is present in the composition in an amount not more than 200 ppb after storage at ambient temperature for a period of 9 months or less, said Aluminum comprising, from about 1.0 ppb to about 100 ppb of Aluminum from the container, from about 1.0 ppb to about 100 ppb of Aluminum from stopper for the container, from about 1.0 ppb to about 100 ppm of Aluminum from the L-cysteine, and from about 1.0 ppb to about 20 ppb of Aluminum from the water.

32. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, wherein the Aluminum is present in the composition in an amount not more than 200 ppb after storage at ambient temperature for a period of 12 months or less, said Aluminum comprising, from about 1.0 ppb to about 100 ppb of Aluminum from the container, from about 1.0 ppb to about 100 ppb of Aluminum from stopper for the container, from about 1.0 ppb to about 100 ppm of Aluminum from the L-cysteine, and from about 1.0 ppb to about 20 ppb of Aluminum from the water.

33. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, wherein cysteine is present in the composition in an amount not more than 2 wt % relative to L-cysteine after storage at ambient temperature for a period of 9 months or less.

34. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, wherein cysteine is present in the composition in an amount not more than 1 wt % relative to L-cysteine after storage at ambient temperature for a period of 9 months or less.

35. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, wherein cysteine is present in the composition in an amount not more than 0.5 wt % relative to L-cysteine after storage at ambient temperature for a period of 9 months or less.

36. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, wherein cysteine is present in the composition in an amount of about 0.3 wt % relative to L-cysteine after storage at ambient temperature for a period of 9 about months.

37. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, wherein pyruvic acid is present in the composition in an amount not more than 2 wt % relative to L-cysteine after storage at ambient temperature for a period of 9 months or less.

38. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, wherein pyruvic acid is present in the composition in an amount not more than 1 wt % relative to L-cysteine after storage at ambient temperature for a period of 9 months or less.

39. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, wherein pyruvic acid is present in the composition in an amount not more than 0.5 wt % relative to L-cysteine after storage at ambient temperature for a period of 9 months or less.

40. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, wherein pyruvic acid is present in the composition in an amount not more than 0.3 wt % relative to L-cysteine after storage at ambient temperature for a period of 9 months or less.

41. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, wherein pyruvic acid is present in the composition in an amount not more than 0.2 wt % relative to L-cysteine after storage at ambient temperature for a period of 9 months or less.

42. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, wherein pyruvic acid is present in the composition in an amount not more than 0.1 wt % relative to L-cysteine after storage at ambient temperature for a period of 9 months or less.

43. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, further comprising in the vial, headspace oxygen in an amount of less than 1.0%.

44. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, further comprising in the vial, headspace oxygen in an amount of less than 0.9%.

45. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, further comprising in the vial, headspace oxygen in an amount of less than 0.8%.

46. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, further comprising in the vial, headspace oxygen in an amount of less than 0.6%.

47. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, further comprising in the vial, headspace oxygen in an amount of less than 0.4%.

48. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, further comprising in the vial, headspace oxygen in an amount of less than 0.2%.

49. The composition of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, wherein the pH of the composition is about 1.6 to about 2.0.

50. A stable composition from about 100 mL to about 1000 mL for administration via a parenteral infusion within about 24 to about 48 hours of admixture, comprising a mixture of a composition of L-Cysteine of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49; and an amino acid composition that is essentially free of L-Cysteine comprising one or more amino acids selected from the group consisting of: leucine, isoleucine, lysine, valine, phenylalanine, histidine, threonine, methionine, tryptophan, alanine, arginine, glycine, proline, serine, and tyrosine.

51. The stable composition for infusion of embodiment 50, wherein the composition of L-Cysteine is the composition of embodiment 1, 12 or 28.

52. The stable composition for injection of embodiment 50 or 51, wherein the Aluminum is present in an amount from about 1.0 parts per billion (ppb) to about 100 ppb.

53. The stable composition for injection of embodiment 50, 51 or 52, wherein the Aluminum is present in an amount from about 1.0 parts per billion (ppb) to about 50.0 ppb.

54. The stable composition for injection of embodiment 50, 51, 52 or 53, wherein the Aluminum is present in an amount from about 1.0 parts per billion (ppb) to about 30.0 ppb.

55. The stable composition for injection of embodiment 50, 51, 52, 53 or 54, further comprising a sugar.

56. The stable composition for injection of embodiment 50, 51, 52, 53, 54 or 55, wherein the sugar is dextrose.

57. A method of reducing Aluminum administration from a parenteral nutrition regimen comprising L-cysteine, comprising:
    administering to a subject a composition of embodiment 50, 51, 52, 53, 54, 55 or 56,
    wherein the Aluminum administered to said subject is reduced compared to administration of a standard parenteral composition comprising L-cysteine.

58. The method of embodiment 57, wherein the Aluminum is reduced by about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95%.

59. A method of reducing Aluminum administration from a total parenteral nutrition regimen comprising L-cysteine, the method comprising, mixing a composition comprising L-cysteine or a pharmaceutically acceptable salt thereof and/or hydrate thereof comprising:
    Aluminum in an amount from about 10 parts per billion (ppb) to about 80 ppb;
    L-cysteine in an amount from about 0.001 wt % to about 2.0 wt % relative to L-cysteine; and
    pyruvic acid in an amount from about 0.001 wt % to about 2.0 wt % relative to L-cysteine;
    with a composition comprising one or more amino acids selected from the group consisting of: leucine, isoleucine, lysine, valine, phenylalanine, histidine, threonine, methionine, tryptophan, alanine, arginine, glycine, proline, serine, and tyrosine; and
    a pharmaceutically acceptable carrier, comprising water, to form a composition for infusion having a volume of about 100 mL to about 1000 mL, wherein the Aluminum provided in said parenteral nutrition regimen is from about 1-2 to about 4-5 micrograms/kg/day.

60. A method of treating a subject having an adverse health condition that is responsive to L-cysteine administration, comprising:
    diluting a stable L-cysteine composition of embodiments 50, 51, 52, 53, 54, 55 or 56, with an intravenous fluid to prepare a diluted L-cysteine composition for infusion; and
    infusing the diluted L-cysteine composition for infusion to a subject to provide a therapeutically effective dose of L-cysteine or a pharmaceutically acceptable salt thereof and/or hydrate thereof to the subject in a therapeutically effective dosing regimen.

61. The method of embodiment 57, 58, 59, or 61, wherein said administering is from 30 minutes to about 24-48 hrs.

62. The method of embodiment 61, wherein the amount of Aluminum in the composition results in a daily dosage of Aluminum from about 1 mcg/kg/day to about 4 mcg/kg/day, or about 2 mcg/kg/day to about 4 mcg/kg/day, or about 1 mcg/kg/day to about 5 mcg/kg/day, or about 2 mcg/kg/day to about 5 mcg/kg/day.

63. The method of embodiment 61 or 62, wherein the intravenous fluid is a member selected from the group consisting of: isotonic saline, glucose solution, glucose saline, dextrose solution, crystalline amino acid solution, and combinations thereof.
64. The method of embodiment 61, 62 or 63, wherein administering is performed via intravenous infusion.
65. The method of embodiment 61, 62, 63, or 64, wherein L-cysteine or a pharmaceutically acceptable salt thereof and/or hydrate thereof is administered at a rate of from about 1 mL/min to about 10 ml/min.
66. The method of embodiment 61, 62, 63, 64 or 65, wherein the therapeutically effective dose of L-cysteine or a pharmaceutically acceptable salt thereof and/or hydrate thereof is an amount from about 50 mg to about 1200 mg.
67. The method of embodiment 61, 62, 63, 64, 65 or 66, wherein the therapeutically effective dose of L-cysteine or a pharmaceutically acceptable salt thereof and/or hydrate thereof is an amount of about 100-500 mg.
68. The method of embodiment 61, 62, 63, 64, 65, 66 or 67, wherein the L-cysteine is L-cysteine hydrochloride monohydrate.
69. The method of embodiment 61, 62, 63, 64, 65, 66, 67 or 68, wherein the subject is a subject in need of total parenteral nutrition (TPN).
70. The method of embodiment 61, 62, 63, 64, 65, 66, 67, 68 or 69, wherein the subject is an infant having an age of 6 months or less.
71. The method of embodiment 61, 62, 63, 64, 65, 66, 67, 68, 69, 70 or 71, wherein the therapeutically effective dosing regimen is a total parenteral nutrition (TPN) dosing regimen.
72. A method of preparing the composition of any above embodiment, comprising stirring Water for Injection, USP (WFI) in a vessel at a temperature of NMT about 60° C.;

Contacting the stirring WFI with Argon until the dissolved oxygen is NMT 1 ppm;

Allowing the vessel to cool to a temperature of NMT 30° C.;

Contacting under the Argon the WFI with L-Cysteine Hydrochloride, Monohydrate, USP (L-Cysteine) for NTL about 15 mins;

Continuing the mixing under Argon until the dissolved oxygen is NMT 1 ppm;

Adjusting the pH to about 1.8 with concentrated Hydrochloric Acid, NF and/or 5.0

N Sodium Hydroxide, NF;

Mixing for a minimum of about 10 minutes;

Capping the vessel under Argon and allowing to stand; and

Performing Head Space oxygen Reduction after filling, wherein the dissolved oxygen is about 0.1 ppm to about 5 ppm.

With this in mind, the following examples are intended to illustrate, but not limit, various aspects of the compositions and methods described herein.

EXAMPLES

Example 1

Compounding L-Cysteine Hydrochloride Injection, USP, 50 mg/mL, 10 mL Vial

Compounding was initiated with the addition of 40±1.0 kg of Water for Injection, USP (WFI) was added to the Xcellerex Mixing System via an addition funnel. A target water temperature of NMT 60° C. was maintained throughout WFI addition using a heat exchanger. With continuous mixing at a speed of 126 rpm, Argon overlaying of the WFI began in the mixing bag and continued until the dissolved oxygen was NMT 1 ppm; then the mixing bag was allowed to cool to a temperature of NMT 30° C.

With continuous mixing and Argon overlaying, the L-Cysteine Hydrochloride, Monohydrate, USP (L-Cysteine) was added directly into the vortex of the mixing bag. The mixing continued for NLT 15 minutes or until complete dissolution was observed. The dissolved oxygen content was measured and recorded prior to the addition of L-Cysteine, immediately following the addition of L-Cysteine, and following the NLT 15-minute mixing period. With continuous mixing and Argon overlaying, the temperature, pH and dissolved oxygen of the solution was measured and recorded. Argon overlaying continues until the dissolved oxygen was NMT 1 ppm.

With continuous mixing and Argon overlaying, the solution's pH was adjusted to a target of 1.8 with concentrated Hydrochloric Acid, NF and/or 5.0 N Sodium Hydroxide, NF. Following pH adjustment, the solution was allowed to mix for a minimum of 10 minutes, and then the pH was verified and adjusted as needed with the Hydrochloric Acid, NF and/or N Sodium Hydroxide, NF. Then, the solution's weight, adjusted pH and dissolved oxygen was measured and recorded.

With continuous mixing and Argon overlaying, the solution was q.s.'d with the WFI to a final weight of 50.6 kg and allowed to mix for approximately 10 minutes. The final solution weight, solution temperature, solution pH, and dissolved oxygen was then measured and recorded. Following these steps, the mixing bag was fully inflated with Argon and capped, and the solution was transferred from the mixing bag to the solution holding bag.

Example 2

L-Cysteine Injection in High Quality Glass Vials

L-Cysteine injection was compounded as per Example 1. The bulk solution was filled then using high quality glass vials (10 mL) from Schott. These vials are known as Schott Type 1 USP glass. The glass was a standard glass of pharmaceutical quality but was uncoated. The product was put on stability and was monitored for impurities, particulates, and Aluminum. The product was quite stable for all the time points tested up to 12 months. There were no unacceptable particulate counts.

However, as the data show, the product resulted in an unacceptably high aluminum content. The data for aluminum levels are shown below.

TABLE 6

Aluminum Levels

| | | 6 Months | |
|---|---|---|---|
| Lot # | Release | 25° C./60% RH | 40° C./75% RH |
| XMHH1609 | 212 ppb | 569 ppb | 1.306 ppb |
| XMHH1610 | 199 ppb | 748 ppb | 1.374 ppb |
| XMHH1611 | 230 ppb | 726 ppb | 1.044 ppb |

Example 3

L-Cysteine Injection in Plastic Vials

L-Cysteine injection was compounded as per Example 1. The bulk solution was filled then using plastic vials obtained from Medicopak, Inc. These vials are made of cyclic olefin copolymer (COC). The product was put on stability and was monitored for impurities, particulates, and Aluminum. The product was not stable beyond 1 month at accelerated storage conditions and failed at room temperature conditions by the third month data point.

TABLE 7

| | Particulate levels | | |
|---|---|---|---|
| Lot Number/Vial | Release | 1 Month/ 40° C./75% RH* | 3 Month/ 25° C./60% RH* |
| XMHG1700/10 mL COC vial | Passing | Failed Visual, particulates | Failed Visual, particulates |
| XMHG1701/10 mL COC vial | Passing | Failed Visual, particulates | Failed Visual, particulates |
| XMHG1702/10 mL COC vial | Passing | Failed Visual, particulates | Failed Visual, particulates |

However, the product showed acceptable aluminum content. The data for aluminum levels are shown below.

TABLE 8

| | Aluminum Levels | | |
|---|---|---|---|
| Time Point | Lot XMHG 1700 | Lot XMHG 1701 | Lot XMHG 1702 |
| Time Zero | 1 ppb | 2 ppb | 1 ppb |

Aluminum at additional time points was not measured because the product was abandoned due to unacceptably high particulate count.

Example 4

Headspace Reduction and Argon Overlay

Data from Example 3 show that plastic vials do not provide the desired purity and stability of a L-cysteine composition for injection. This study was to evaluate the parameters to determine headspace oxygen reduction conditions. The product was manufactured as per Example 1. The drug product was overlaid with Argon until the dissolved oxygen levels were no more than (NMT) 1 part per million (PPM). Vials were filled and placed in the VirTis Benchmark Lyophilizer, OP4159, for Head Space reduction. In addition, empty vials were also placed into the lyo for Head Space reduction as part of the study.

Multiple points were monitored during the manufacturing process as part of the study including the following: 1) Compounding; 2) Pre-Filling; 3) Filling; 4) Post Filling; and 5) Head Space Reduction (HSR). The monitoring involved taking dissolved oxygen (DO) measurements on drug product for filled vials throughout the manufacturing process and performing Head Space Gas Analysis on drug product for both filled and empty vials post head space reduction. Additionally, fill hold samples representing the maximum exposure during the filling step were analyzed for the dissolved oxygen and Head Space Oxygen Analysis.

The sampling and testing that was performed per the study is shown in Table 9. Samples were collected throughout the manufacturing process to determine the impact of critical process parameters on its predetermined critical quality attribute.

TABLE 9

| | Sampling and Testing Methodology | | |
|---|---|---|---|
| Operation | Sample Location/Quantity | Testing Requirements | Acceptance Criteria |
| Compounding | The bulk solution was mixed under Argon overlaying. Measure and record final solution weight, solution temperature, solution pH, and dissolved oxygen. Measure and record the final dissolved oxygen. | Dissolved Oxygen | Dissolved Oxygen <1 ppm |
| Filling | For Load A [Trays 1-4, 17-20] use forceps to remove four (4) filled vials from each tray as it is filled Fully seat the stoppers of the removed filled vials immediately after removal and then label vials appropriately | Dissolved Oxygen | Dissolved Oxygen = Report Value |
| Filling Hold | As Tray 1 is loaded into the Lyo, using forceps, carefully remove 20 vials from the appropriate locations. Do not fully stopper the vials. Mark the vials "Fill Hold" Similarly, after Tray 21 has been completely filled and is being placed into the cart, use forceps to remove twenty (20) filled vials from the appropriate As Tray 21 is being loaded into the Lyophilizer for Head Space Reduction, use forceps to remove two (2) of the vials marked "Fill Hold", fully seat the stoppers of the vials, and label appropriately. | Dissolved Oxygen | Dissolved Oxygen = Report Value |
| Lyo Loading | For Trays 1-4, 17-20, 21-24, and 37-40, use forceps to remove two (2) filled vials, as each tray is loaded into the Lyo, fully seat the stoppers of the vials, and label appropriately | Dissolved Oxygen | Dissolved Oxygen = Report Value |

TABLE 9-continued

Sampling and Testing Methodology

| Operation | Sample Location/Quantity | Testing Requirements | Acceptance Criteria |
|---|---|---|---|
| Capping | Following headspace reduction and immediately prior to loading each tray into the RAB for capping, use forceps to remove four (4) filled vials from each tray. Place a mark on each of the removed vials for identification purposes and place the marked vials back into the tray. Load the tray into the RAB for capping. Following the capping of each tray, remove the marked vials from the tray and label appropriately. | Dissolved Oxygen<br><br>Head Space Gas Analysis | Dissolved Oxygen = Report Value<br><br>Head Space Gas Analysis = Report Value |
| Capping Fill Hold | Following headspace reduction and capping, remove the eighteen (18) vials marked "Fill Hold" from Tray 21 for testing. | Dissolved Oxygen<br><br>Head Space Gas Analysis | Dissolved Oxygen = Report Value<br><br>Head Space Gas Analysis = Report Value |

The data collected are as follows: Dissolved oxygen; Comparison of dissolved oxygen levels per tray at various stages of the manufacturing process; Filled vials head space oxygen; Held vials dissolved oxygen (ppm) and head space oxygen content (%); Comparison of Post Head Space Dissolved Oxygen (ppm) and Head Space Oxygen Content (%).

Figure 2:
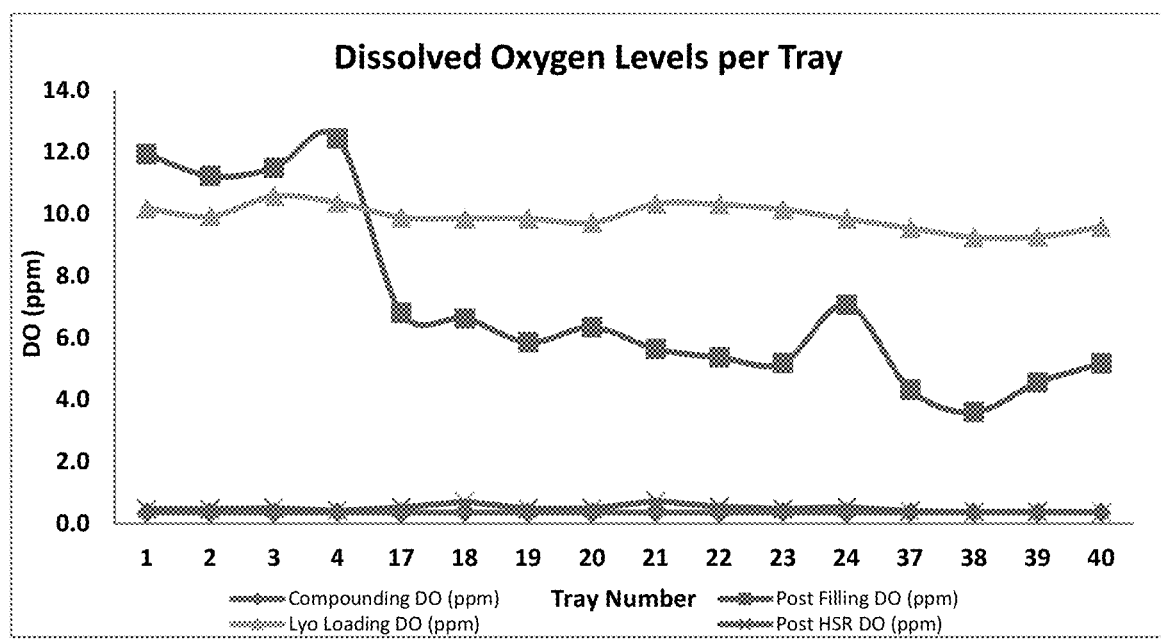
FIG. 2 depicts the overall trend of the results from the experiments that demonstrate the effectiveness of the Head Space Reduction (HSR) cycle in attaining reduced and consistent dissolved oxygen (DO) levels in the finished drug product. The results showed a trend with an increase in dissolved oxygen level from 0.36 parts per million (ppm) recorded during compounding, to an average of 5.12 ppm measured after filling, a further increase to an average of 9.92 ppm while loading the Lyophilizer, and finally a reduction of dissolved oxygen to an average of 0.50 ppm after headspace reduction.

Dissolved oxygen data at various stages of the manufacturing process are shown in Table 10. A two (2) hour delay in the DO testing for the Post Filling—Pre HSR samples (Tray 1-4; tested using gas calibration) exhibited an average value of 11.77 ppm, an increase of 6.65 ppm from the average of 5.12 ppm measured live time after filling using the liquid calibration. Furthermore, the samples tested live time but using the gas calibration (Tray 17-20) exhibited an average value of 6.41 ppm, an increase of 1.29 ppm from the average of 5.12 ppm measured after filling using the liquid calibration. Starting Tray 21 of the Post Filling—Pre HSR step, the calibration was corrected to a liquid calibration. Comparison of dissolved oxygen levels at various stages of the manufacturing process is provided in FIGS. 1 and 2.

TABLE 10

Dissolved Oxygen Levels.

| Tray Number | Post Filling - Pre HSR (ppm) | Post Filling - During Loading of Lyo (ppm) | Post HSR - Capping - Filled Vials (ppm) |
|---|---|---|---|
| 1 | 11.932 | 10.179 | 0.480 |
| 2 | 11.228 | 9.925 | 0.470 |
| 3 | 11.486 | 10.577 | 0.508 |
| 4 | 12.441 | 10.370 | 0.409 |
| 17 | 6.808 | 9.893 | 0.525 |
| 18 | 6.628 | 9.859 | 0.707 |
| 19 | 5.860 | 9.854 | 0.486 |
| 20 | 6.343 | 9.720 | 0.495 |
| 21 | 5.641 | 10.329 | 0.735 |
| 22 | 5.374 | 10.308 | 0.546 |
| 23 | 5.190 | 10.149 | 0.481 |
| 24 | 7.073 | 9.844 | 0.541 |
| 37 | 4.328 | 9.544 | 0.403 |
| 38 | 3.604 | 9.251 | 0.378 |
| 39 | 4.559 | 9.265 | 0.390 |
| 40 | 5.173 | 9.577 | 0.369 |
| Average | 5.117 | 9.915 | 0.495 |
| STD | 1.03 | 0.39 | 0.11 |
| % RSD | 20.1 | 3.9 | 21.3 |

TABLE 11

Filled Vials Head Space Oxygen.

| Tray Number | Post HSR - Capping - Filled Vials (% Oxygen) | Post Capping - Empty Vials (% Oxygen) |
|---|---|---|
| 1 | 1.147 | 0.981 |
| 2 | 1.399 | 1.116 |
| 3 | 1.551 | 0.980 |
| 4 | 0.950 | 1.139 |
| 17 | 1.382 | 1.156 |
| 18 | 1.766 | 1.236 |
| 19 | 1.154 | 1.224 |
| 20 | 1.265 | 1.180 |
| 21 | 1.844 | 1.221 |
| 22 | 1.365 | 1.169 |
| 23 | 0.890 | 1.295 |
| 24 | 1.148 | 1.114 |
| 37 | 0.880 | 1.300 |
| 38 | 0.871 | 1.151 |
| 39 | 0.850 | 1.097 |
| 40 | 0.889 | 1.042 |
| Average | 1.209 | 1.150 |
| STD | 0.32 | 0.10 |
| % RSD | 26.7 | 8.3 |

TABLE 12

Held vials dissolved oxygen (ppm) and head space oxygen content (%).

| Held Vials - Tray 1/ Tray 21 | Dissolved Oxygen Post Filling - Loading of Lyo (ppm) | Dissolved Oxygen Post HSR - Capping - Filled Vials (ppm) | Head Space Oxygen % Post HSR - Capping - Filled Vials (%) |
|---|---|---|---|
| Sample 1 | 10.685 | 0.578 | 1.563 |
| Sample 2 | 10.467 | 0.588 | 1.390 |
| Sample 3 | — | 0.565 | 1.522 |
| Sample 4 | — | 0.550 | 1.447 |
| Average | 10.576 | 0.570 | 1.481 |
| STD | 0.15 | 0.02 | 0.08 |
| % RSD | 1.5 | 2.9 | 5.2 |

TABLE 13

Comparison of Post Head Space Dissolved Oxygen (ppm) and Head Space Oxygen Content (%).

| | Dissolved Oxygen Pre HSR (ppm) | Dissolved Oxygen Post HSR - (ppm) | Head Space Oxygen % Post HSR (%) |
|---|---|---|---|
| PROT-000055 Study Empty Vials Avg. | — | — | 1.150 |
| PROT-000055 Study Filled Vials Avg. | 9.915 | 0.495 | 1.209 |
| 2018-RD-022 Study Empty Vials Avg. | — | — | 0.49 |
| 2018-RD-022 Study Filled Vials Avg. | 7.14 | 2.55 | 1.27 |
| Lot XMHJ1705 | — | 0.637 | 2.28 |
| Lot XMHJ1706 | — | 0.391 | 1.92 |
| Lot XMHJ1707 | — | 1.585 | 1.94 |

The results from these experiments demonstrate the effectiveness of the Head Space Reduction (HSR) cycle in attaining reduced and consistent dissolved oxygen (DO) levels in the finished drug product. The results showed a trend with an increase in dissolved oxygen level from 0.36 parts per million (ppm) recorded during compounding, to an average of 5.12 ppm measured after filling, a further increase to an average of 9.92 ppm while loading the Lyophilizer, and finally a reduction of dissolved oxygen to an average of 0.50 ppm after headspace reduction. The overall trends are displayed in FIGS. 1 and 2. The plots and data also show that the average increase in dissolved oxygen levels from compounding to the filled vials was 4.76 ppm. Also, as the vials were stored in the transfer cart, an average dissolved oxygen increase of about 4.80 ppm was observed prior to being loaded in the Lyophilizer for head space reduction. The total average increase in dissolved oxygen levels from compounding to vials being loaded in the lyophilizer was 9.56 ppm. The average decrease in dissolved oxygen observed in vials post head space reduction was 9.42 ppm. In addition, the oxygen levels obtained across all trays analyzed pre and post HSR were consistent throughout the manufacturing process.

Head Space Gas Analysis was performed on both filled and empty vials taken from designated locations in selected trays. Percent (%) Oxygen results achieved across the trays showed a relatively uniform head space reduction process throughout the chamber. The average % Oxygen for the empty vials was found to be 1.15%, compared with 1.21% for the filled vials (Reference Table 11).

Dissolved Oxygen and Head Space Gas Analysis were also performed on the Held Vials from designated locations in Tray 1 as part of the stressed sample analysis over the course of the manufacturing process. The results showed a comparable trend to that observed for the regular samples across the study (Reference Table 12). Specifically, an increase in dissolved oxygen level from 0.36 ppm recorded during compounding, to 5.64 ppm measured after filling, a further increase to an average of 10.58 ppm while loading the Lyophilizer, and finally a reduction of dissolved oxygen to an average of 0.57 ppm after headspace reduction. The average % Oxygen for the filled held vials was found to be 1.48%, compared with 1.21% for the filled regular vials. This indicated that the HSR cycle was effective in achieving comparable DO and Headspace oxygen results irrespective of the maximum fill time exposure (approximately 7 hours; represented by the Fill Hold Vials) and has no impact on the quality of the product. The use of the Lyophilizer, in the Head Space Reduction of L-Cysteine Hydrochloride Injection, USP (50 mg/mL) has been shown to be effective for the control of reduced and consistent oxygen levels, and is suitable for scale up for the existing process and equipment as the product meets all the critical quality attributes.

Example 5

Head space oxygen reduction was accomplished using an automated filling equipment that can handle high speed filling, in contrast to slow or low volume operation such as through a lyophilizer as described in Examples 1 and 4. The high-speed filler is capable of using vacuum and gas overlay in alternate pulses to reduce the head space oxygen. Each pulse is timed to be within 0.1 to 5 seconds such that typically 3-5 pulses are conducted in one head space oxygen reduction cycle. The pulse rate can be adjusted after multiple trials to provide optimal headspace reduction with optimal speed of the filler such that no product is lost through back suction or through spillage and average speeds of from about 20 vials/minute to about 200 vials per minute, depending on the number of fill heads used.

Figure 3:
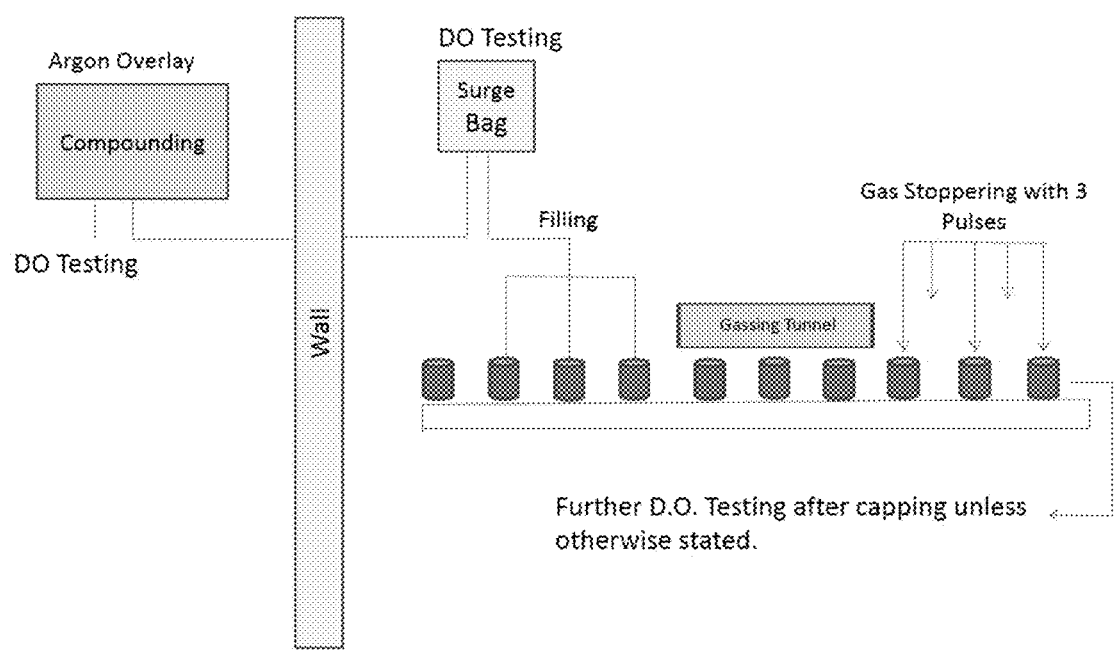
FIG. 3 depicts a process filler set up to fill and reduce head space oxygen.

A 50 L batch was prepared utilizing the current compounding procedure described above in Example 1. The filler was set up to fill and reduce head space oxygen as per the process shown in FIG. 3.

The total head space reduction cycle lasted about 25 seconds per operation. The vials were analyzed for head space oxygen at time zero and at 1-month time point. The data are shown below.

The evaluation of the filler's performance demonstrated that the headspace oxygen control was comparable to or better than the current process for L-Cysteine. Headspace oxygen values obtained ranged from 0.2% to 0.5% for all vials filled, including empty vials during start up. Vials tested after 1-month storage at ambient conditions also maintain headspace oxygen levels between 0.4 and 1.5%. The Tables below show a summary of the results for the in process and 1-month stability testing. Also included below is a comparison of the in-process data obtained from previously manufactured lots of L-Cysteine utilizing the lyophilizer headspace reduction method. The data show the headspace oxygen values at Time Zero are lower with the high-speed filler than the lyophilizer process.

TABLE 14

Headspace Oxygen Levels at Time Zero for High-Speed Filler

PROT-000213 - Time Zero

| | Tray 5 | Tray 10 | Overall Low | Overall High | Average |
|---|---|---|---|---|---|
| Headspace O$_2$ (%) | 0.473 | 0.378 | 0.243 | 0.490 | 0.372 |

TABLE 15

Headspace Oxygen Levels at 1 Month for High-Speed Filler

PROT-000213 - 1 Month

| | Tray No. 5 | | | Tray No. 10 | | |
|---|---|---|---|---|---|---|
| | Low | High | Average | Low | High | Average |
| Headspace O$_2$ (%) | 0.412 | 1.518 | 0.995 | 0.98 | 1.454 | 1.262 |

TABLE 16

Comparison of Headspace Oxygen Levels between
Lyophilizer and High-Speed Filler Operations

| Batch | XMHJ1705 (Current Process) | XMHJ1706 (Current Process) | XMHJ1707 (Current Process) | PROT-000213 (High Speed Filler) |
|---|---|---|---|---|
| Average | 2.3% Oxygen | 1.9% Oxygen | 1.9% Oxygen | 0.4% Oxygen |
| Low | N/A | N/A | N/A | 0.2% Oxygen |
| High | N/A | N/A | N/A | 0.5% Oxygen |
| 1 Month Room Temperature | 0.9% Oxygen | 2.8% Oxygen | 1.2% Oxygen | 1.1% Oxygen (0.4% to 1.5%) |

N/A—Not Applicable

Figure 4:
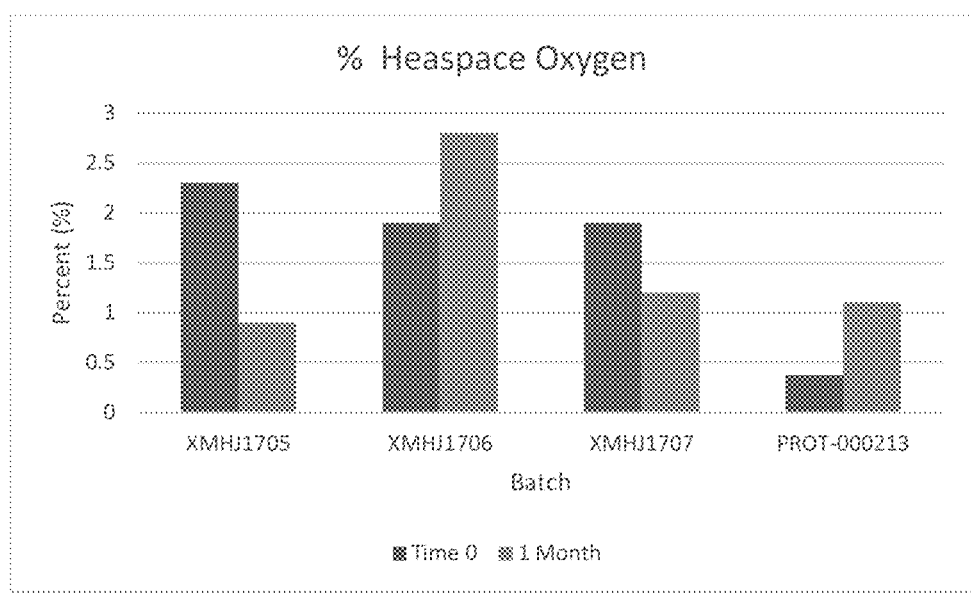
FIG. 4 shows data for the process of Example 4. The plot shows comparison of oxygen headspace control between the lyophilizer chamber headspace control method versus the high-speed filler vacuum stoppering system. The time zero oxygen headspace results for the batch PROT-000213 are shown in comparison to the previously manufactured lots. Results shown were measured at the time of manufacturing on samples of vials from the batches.

FIG. 4 shows the comparison of oxygen headspace control between the lyophilizer chamber headspace control method versus the high-speed filler vacuum stoppering system. The lyophilizer chamber for headspace reduction was utilized for lots XMHJ1705, XMHJ1706, and XMHJ1707 of L-Cysteine Hydrochloride injection. The time zero oxygen headspace results for the engineering batch PROT-000213 are shown in comparison to the previously manufactured lots. Results shown were measured at the time of manufacturing on samples of vials from the batches. Oxygen percentage was taken for the samples from PROT-000213 using the NeoFox Phase Fluorometer. Lots XMHJ1705, XMHJ1706, and XMHJ1707 used Argon Headspace Analysis, QCTM-000014.

Figure 5:
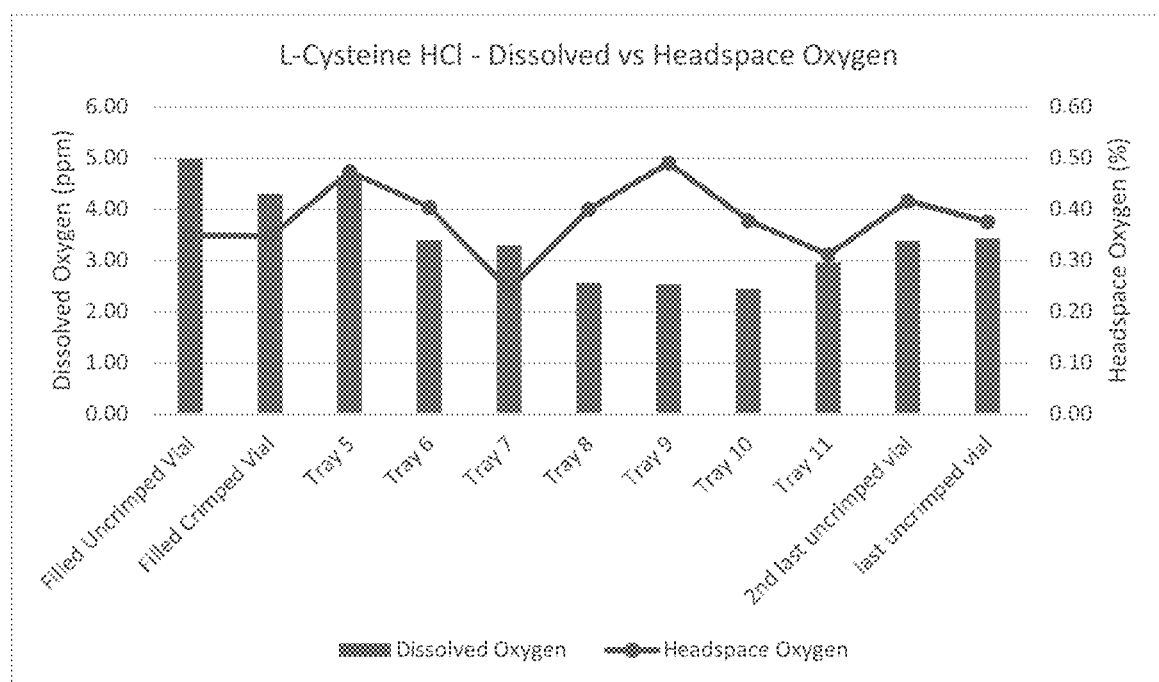
FIG. 5 depicts the data measured for dissolved oxygen levels in the process of Example 4.

In addition to the head space oxygen levels, dissolved oxygen levels were also measured. Data are shown in FIG. 5.

The dissolved oxygen levels and head space oxygen levels were measured again at 1 month stability time point at room temperature conditions:

TABLE 17

Headspace and Dissolved Oxygen Data Comparison at 1 month
Study - 1 Month

| | Tray No. 5 | | | | Tray No. 10 | | |
|---|---|---|---|---|---|---|---|
| | Sample 1 | Sample 2 | Sample 3 | Sample 4 | Sample 1 | Sample 2 | Sample 3 |
| Headspace O$_2$ (%) | 0.576 | 0.412 | 1.518 | 1.475 | 0.98 | 1.454 | 1.352 |
| Dissolved O$_2$ (ppm) | 0.545 | 0.706 | 2.328 | 2.042 | 2.173 | 2.372 | 2.149 |

Example 6

Purity Profile and Long-Term Stability of
L-Cysteine Composition for Injection

An L-cysteine composition for injection was manufactured as described in Example 1. The glass used was Schott Type 1 USP Plus glass, internally coated with silicon dioxide. The composition was subjected to stability testing to evaluate the stability of the composition over time. Table 18 shows various stability data collected for the L-cysteine composition for injection over a 9-month testing period. Samples of exhibit batches stored upright at room temperature for 9 months at 25° C./60% RH. Note: two samples were tested for dissolved oxygen and head-space oxygen.

TABLE 18

Characterization of L-Cysteine Composition for Injection

| Test | XMHJ1705 | XMHJ1706 | XMHJ1707 |
|---|---|---|---|
| L-Cysteine HCl | Up 100.4% | Up 101.3% | Up 101.2% |
| Related Compounds: | | | |
| L-Cystine | 0.3% | 0.3% | 0.3% |
| Pyruvic Acid Total | 0.1% | 0.2% | 0.1% |
| Specified RRT-1.98 | 0.2% | 0.2% | 0.2% |
| Individual Unspecified | ND | ND | ND |
| Total Impurities | 0.5% | 0.7% | 0.6% |
| Dissolved Oxygen | (1) 0.12 ppm (2) 0.13 ppm | (1) 0.13 ppm (2) 0.14 ppm | (1) 0.14 ppm (2) 0.13 ppm |
| Head-Space Oxygen | (1) 0.16% (2) 0.37% | (1) 0.53% (2) 0.89% | (1) 0.56% (2) 0.50% |
| Aluminum Content | 3.2 ppb | 2.9 ppb | 5.6 ppb |
| Description | Clear colorless solution | Clear colorless solution | Clear colorless solution |

Example 7

Effect of Dissolved Oxygen and Headspace Oxygen
on L-Cysteine and Cystine Levels An L-cysteine composition for injection was manufactured as described in Example 1. However, samples of exhibit batches were tested without head-space reduction and argon overlay during compounding, then filled, stoppered and capped. Samples were tested within one week of manufacturing date. Data in Table 19 show the marked effects of lack of headspace and dissolved oxygen on component levels within one week. L-Cystine increased by about 0.4%-0.7% within a week for samples with higher dissolved oxygen and head-space oxygen.

TABLE 19

Effect of lack of Headspace and
Dissolved Oxygen Control on Product Purity

| Test | Prior to Head-Space Reduction Tray 1 | Prior to Head-Space Reduction Tray 19 | Prior to Head-Space Reduction Tray 23 | Ave Values for after completed Batch |
|---|---|---|---|---|
| L-Cysteine HCl | 99.9% | 100.1% | 100.0% | 102.0% |
| L-Cystine | 0.8% | 0.5% | 0.6% | 0.1% |
| Head-Space Oxygen | 20.8% | 20.3% | 20.3% | 1.2% |
| Dissolved Oxygen | 8.3 ppm | 8.6 ppm | 8.6 ppm | 0.50 ppm |

Example 8

Evaluation of Anions in L-Cysteine Product

Inorganic anionic leachables were determined using validated potentiometric methods utilizing ion selective electrodes. Fluoride and Iodide were evaluated for this drug product. The leachables testing results are listed in Tables 20 and 21 below.

TABLE 20

Leachable Iodide Results for L-Cysteine HCl Injection [I⁻] (ppb)

XMHJ1705

| | 25° C./60% RH | | | 40° C./75% RH | | |
|---|---|---|---|---|---|---|
| Replicate | Upright | Horizontal | Inverted | Upright | Horizontal | Inverted |
| 1 | 28.1 | 27.4 | 27.1 | 25.2 | 24.9 | 24.7 |
| 2 | 25.9 | 26.3 | 25.9 | 24.0 | 24.1 | 24.1 |
| 3 | 28.1 | 25.3 | 25.3 | 24.0 | 22.3 | 21.6 |
| Average | 27.4 | 26.3 | 26.1 | 24.4 | 23.7 | 23.5 |
| SD | 1.3 | 1.0 | 0.9 | 0.7 | 1.3 | 1.6 |
| % RSD | 4.7 | 3.9 | 3.6 | 2.7 | 5.6 | 7.0 |

XMHJ1706

| | 25° C./60% RH | | | 40° C./75% RH | | |
|---|---|---|---|---|---|---|
| Replicate | Upright | Horizontal | Inverted | Upright | Horizontal | Inverted |
| 1 | 81.7 | 80.3 | 82.8 | 80.3 | 82.0 | 81.8 |
| 2 | 83.1 | 81.7 | 81.5 | 82.5 | 82.3 | 81.3 |
| 3 | 81.7 | 81.7 | 81.8 | 78.1 | 81.9 | 82.8 |
| Average | 82.2 | 81.2 | 82.0 | 80.3 | 82.1 | 82.0 |
| SD | 0.8 | 0.8 | 0.7 | 2.2 | 0.2 | 0.7 |
| % RSD | 0.9 | 1.0 | 0.9 | 2.7 | 0.2 | 0.9 |

XMHJ1707

| | 25° C./60% RH | | | 40° C./75% RH | | |
|---|---|---|---|---|---|---|
| Replicate | Upright | Horizontal | Inverted | Upright | Horizontal | Inverted |
| 1 | 53.5 | 52.3 | 53.1 | 51.7 | 51.4 | 50.8 |
| 2 | 52.5 | 54.0 | 53.7 | 51.8 | 52.0 | 53.5 |
| 3 | 54.4 | 52.8 | 52.8 | 53.8 | 53.6 | 52.6 |
| Average | 53.5 | 53.0 | 53.2 | 52.4 | 52.3 | 52.3 |
| SD | 1.0 | 0.9 | 0.4 | 1.2 | 1.1 | 1.4 |
| % RSD | 1.8 | 1.7 | 0.8 | 2.2 | 2.1 | 2.6 |

TABLE 21

Leachable Iodide Results for L-Cysteine HCl Injection [I⁻] (ppb)

| | XMHL1702A | | XMHL1702B | |
|---|---|---|---|---|
| | 25° C./60% RH 6 month | 40° C./75% RH 6 month | 25° C./60% RH 6 month | 40° C./75% RH 6 month |
| Iodide (ppb) | 29 | 24 | 24 | 19 |

The leachable results for Fluoride indicate levels below 20 ppb and no observable trend in leachable amount over time or temperature dependence. The leachable results for Iodide indicate that levels were observed ranging from ~20-80 ppb. No noticeable trend in leachable amount including vial orientation or temperature dependence was observed.

Example 9

Elemental Leachables

Elemental leachables were evaluated using a validated inductively coupled plasma mass spectrometric (ICP-MS) method. ICP-MS method is described in detail in USP and other literature in the art. The results for the elemental leachables analysis are summarized in the Table below. The Table lists the Allowable Elemental Concentrations (AEC) for each identified element.

TABLE 22

Elemental Impurity Leachables Results for L-Cysteine HCl Injection [X] (ppb)

| | | XMHJ1705 25° C./60% RH | | | | XMHJ1705 40° C./75% RH | | | XMHJ1705 25° C./60% RH | | |
|---|---|---|---|---|---|---|---|---|---|---|---|
| | | Time point (months) | | | | | | | | | |
| Element | AEC (ppb) | 1 | 3 | 6 | 9 | 1 | 3 | 6 | 12 INV | 12 HOR | 12 UP |
| Molybdenum | 14537 | <0.5 | 2 | 1.75 | 0.6 | <0.5 | 2 | 0.91 | 0.4 | 0.4 | 0.5 |
| Zinc | 12598 | 14 | 2 | 13.84 | 23.4 | 11 | 38 | <QL | 7 | 5 | 3 |
| Iron | 12598 | 25 | 21 | 50.52 | 19 | 16 | 60 | 5.73 | 9 | 157 | 637 |
| Chromium | 10660 | 2 | <QL | <QL | 3.2 | 2 | 6 | <QL | 1 | 2 | 3 |
| Barium | 6784 | 2 | <QL | <QL | <QL | <0.5 | 2 | <QL | 0.4 | 0.4 | 0.4 |
| Tin | 5815 | 1 | 2 | 3.38 | 1.2 | | 3 | 0.88 | 1 | 1 | |
| Copper | 2907 | <0.5 | <QL | <QL | 15.0 | <0.5 | 2 | <QL | 0.5 | 0.8 | 0.6 |
| Manganese | 2423 | 1 | <QL | <QL | 0.3 | <0.5 | 2 | <QL | <QL | 2 | 8 |
| Lithium | 2423 | <0.5 | 5 | 3.90 | 0.1 | <0.5 | 6 | 3.79 | 0.04 | 0.05 | 0.05 |
| Gold | 969 | 5 | 3 | 9.76 | 0.3 | 3 | 4 | 1.76 | 0.4 | <QL | 1 |
| Antimony | 872 | 1 | 1 | 0.88 | 0.1 | 1 | 2 | 0.60 | 0.4 | 0.3 | 0.3 |
| Selenium | 775 | <0.5 | <QL | <QL | 0.1 | <0.5 | 2 | <QL | <QL | 1 | <QL |
| Nickel | 194 | 11 | 9 | 16.66 | 8.1 | 11 | 9 | 0.99 | 14 | 14 | 15 |
| Arsenic | 174 | 1 | <QL | <QL | 0.2 | 1 | 2 | <QL | 0.3 | 0.3 | 0.2 |
| Aluminum | 120 | <QL | <QL | <QL | <QL | <QL | <QL | <QL | (4) <QL | (19) <QL | (5) <QL |
| Vanadium | 97 | <QL | <QL | <QL | <QL | <0.5 | 4 | <QL | <QL | <QL | <QL |
| Silver | 97 | <0.5 | <QL | <QL | <QL | <QL | 17 | <QL | <QL | <QL | <QL |
| Ruthenium | 97 | <0.5 | 1 | 0.72 | <QL | <0.5 | 2 | 0.74 | <QL | <QL | <QL |
| Rhodium | 97 | <0.5 | 4 | 4.31 | <QL | <0.5 | 8 | 4.29 | 0.01 | 0.01 | 0.01 |
| Platinum | 97 | <0.5 | <0.5 | <QL | <QL | <0.5 | 1 | <QL | <QL | <QL | <QL |
| Palladium | 97 | <0.5 | <QL | <QL | <QL | <0.5 | 1 | <QL | 0.06 | 0.06 | 0.1 |
| Osmium | 97 | <0.5 | <QL | <QL | <QL | <0.5 | 1 | <QL | <QL | <QL | <QL |
| Iridium | 97 | <0.5 | 6 | 5.98 | <QL | <0.5 | 7 | 5.92 | 0.04 | 0.03 | 0.04 |
| Thallium | 78 | <0.5 | 4 | 3.59 | <QL | <0.5 | 5 | 3.59 | <QL | <QL | <QL |
| Cobalt | 48 | <0.5 | <QL | <QL | 0.1 | <0.5 | <0.5 | <QL | <QL | <QL | <QL |

TABLE 22-continued

Elemental Impurity Leachables Results for L-Cysteine HCl Injection [X] (ppb)

| | | | | | | | | | | | |
|---|---|---|---|---|---|---|---|---|---|---|---|
| Lead | 48 | 2 | 5 | 6.77 | 1.5 | 2 | 6 | 3.33 | 2 | 2 | 2 |
| Mercury | 29 | <0.5 | 1 | 0.78 | 2 | <0.5 | 1 | 1.10 | 0.7 | 0.7 | 0.6 |
| Cadmium | 19 | <0.5 | 1 | 1.31 | <QL | <0.5 | 2 | 1.30 | <QL | <QL | <QL |

| | | XMHJ1706 25° C./60% RH | | | | XMHJ1706 40° C./75% RH | | | XMHJ1706 25° C./60% RH | | |
|---|---|---|---|---|---|---|---|---|---|---|---|
| | | Time point (months) | | | | | | | | | |
| Element | AEC (ppb) | 1 | 3 | 6 | 9 | 1 | 3 | 6 | 12 INV | 12 HOR | 12 UP |
| Molybdenum | 14537 | <0.5 | 1 | 1.32 | 0.4 | <0.5 | 2 | 1.33 | 0.4 | 0.4 | 0.4 |
| Zinc | 12598 | 10 | 8 | 8.23 | 23.9 | 10 | 36 | 4.25 | 3 | 6 | 8 |
| Iron | 12598 | 9 | 30 | 34.02 | 7.9 | 10 | 41 | 45.60 | 11 | 55 | 10 |
| Chromium | 10660 | 1 | <QL | <QL | 1.9 | 2 | 5 | <QL | 1 | 1 | 1 |
| Barium | 6784 | <0.5 | <QL | <QL | <QL | 1 | 1 | <QL | 0.4 | 0.6 | 0.4 |
| Tin | 5815 | 1 | 2 | 2.91 | 1.3 | 1 | 3 | 2.08 | 1 | 2 | 2 |
| Copper | 2907 | <QL | <QL | <QL | <QL | <QL | 1 | <QL | 1 | 0.2 | <QL |
| Manganese | 2423 | <0.5 | <QL | <QL | 0.3 | <0.5 | 1 | <QL | 0.1 | 0.6 | 0.2 |
| Lithium | 2423 | <0.5 | 4 | 3.84 | 0.1 | <0.5 | 6 | 3.87 | 0.03 | 0.03 | 0.04 |
| Gold | 969 | 2 | 3 | 4.38 | 0.2 | 2 | 4 | 3.99 | 0.2 | 0.2 | 0.3 |
| Antimony | 872 | 1 | 1 | 0.81 | <QL | 1 | 2 | 0.91 | 0.6 | 0.5 | 0.5 |
| Selenium | 775 | <0.5 | <QL | <QL | 0.6 | 1 | 3 | <QL | 0.4 | <QL | 0.4 |
| Nickel | 194 | 11 | 10 | 8.66 | 8.1 | 11 | 9 | 8.68 | 14 | 14 | 14 |
| Arsenic | 174 | <0.5 | <QL | <QL | 0.4 | <0.5 | 2 | <QL | 0.8 | 0.5 | 0.4 |
| Aluminum | 120 | <QL | <QL (2) | <QL | <QL | <QL | <QL | <QL | (5) <QL | (6) <QL | (1) <QL |
| Vanadium | 97 | <QL | <QL | <QL | <QL | <0.5 | 4 | <QL | <QL | <QL | <QL |
| Silver | 97 | <QL | <QL | <QL | <QL | <QL | 17 | <QL | <QL | <QL | <QL |
| Ruthenium | 97 | <0.5 | 1 | 0.73 | <QL | <0.5 | 2 | 0.73 | 0.005 | <QL | 0.003 |
| Rhodium | 97 | <0.5 | 4 | 4.29 | <QL | <0.5 | 8 | 4.28 | 0.007 | 0.005 | 0.008 |
| Platinum | 97 | <0.5 | <0.5 | <QL | <QL | <0.5 | 1 | <QL | <QL | <QL | <QL |
| Palladium | 97 | <0.5 | <QL | <QL | <QL | <0.5 | 1 | <QL | 0.04 | 0.02 | 0.03 |
| Osmium | 97 | <0.5 | <QL | <QL | <QL | <0.5 | 1 | <QL | <QL | <QL | <QL |
| Iridium | 97 | <0.5 | 6 | 5.94 | <QL | <0.5 | 7 | 5.94 | 0.03 | 0.03 | 0.03 |
| Thallium | 78 | <0.5 | 4 | 3.59 | <QL | <0.5 | 5 | 3.59 | <QL | <QL | <QL |
| Cobalt | 48 | <0.5 | <0.5 | <QL | <QL | <0.5 | <0.5 | <QL | <QL | <QL | <QL |
| Lead | 48 | 2 | 6 | 5.53 | 2.0 | 2 | 6 | 5.53 | 2 | 2 | 2 |
| Mercury | 29 | <0.5 | 1 | 1.11 | 1.5 | <0.5 | 1 | 1.01 | 0.7 | 0.7 | 0.7 |
| Cadmium | 19 | <0.5 | 1 | 1.30 | <QL | <0.5 | 2 | 1.30 | <QL | 0.004 | <QL |

| | | XMHJ1707 25° C./60% RH | | | | XMHJ1707 40° C./75% RH | | | XMHJ1707 25° C./60% RH | | |
|---|---|---|---|---|---|---|---|---|---|---|---|
| | | Time point (months) | | | | | | | | | |
| Element | AEC (ppb) | 1 | 3 | 6 | 9 | 1 | 3 | 6 | 12 INV | 12 HOR | 12 UP |
| Molybdenum | 14537 | <0.5 | 1 | 1.22 | 0.4 | <0.5 | 2 | 1.21 | 0.4 | 0.4 | 0.4 |
| Zinc | 12598 | 10 | 4 | 4.28 | 22.7 | 11 | 38 | 3.91 | 7 | 4 | 6 |
| Iron | 12598 | 8 | 26 | 12.55 | 8.3 | 9 | 74 | 17.68 | 8 | 71 | 13 |
| Chromium | 10660 | 1 | <QL | <QL | 2.2 | 1 | 6 | <QL | 1 | 1 | 1 |
| Barium | 6784 | <0.5 | <0.5 | <QL | <QL | <0.5 | 1 | <QL | 0.6 | 0.5 | 0.6 |
| Tin | 5815 | 1 | 2 | 2.13 | 3.2 | 1 | 3 | 2.22 | 1 | 1 | 1 |
| Copper | 2907 | <0.5 | <QL | <QL | <QL | <0.5 | 2 | <QL | 0.2 | 0.2 | 0.1 |
| Manganese | 2423 | <0.5 | <QL | <QL | 0.1 | <0.5 | 1 | <QL | 0.2 | 1 | 0.3 |
| Lithium | 2423 | <0.5 | 3.86 | 3.86 | 0.2 | <0.5 | 6 | 3.88 | 0.03 | 0.03 | 0.06 |
| Gold | 969 | 3 | 3 | 3.98 | 0.1 | 2 | 4 | 3.48 | 0.1 | 0.1 | 0.2 |
| Antimony | 872 | 1 | 1 | 1.01 | <QL | 1 | 2 | 1.06 | 0.6 | 0.6 | 0.6 |
| Selenium | 775 | <0.5 | <QL | <QL | 0.1 | <0.5 | 2 | <QL | 0.4 | <QL | <QL |
| Nickel | 194 | 11 | 8 | 7.71 | 7.4 | 10 | 8 | 7.82 | 14 | 14 | 14 |
| Arsenic | 174 | 1 | <QL | <QL | 0.4 | 1 | 2 | <QL | 0.6 | 0.6 | 0.6 |
| Aluminum | 120 | <QL | <QL | <QL | <QL | <QL | <QL | <QL | (5) <QL | (26) <QL | (39) <QL |
| Vanadium | 97 | <QL | <QL | <QL | <QL | <0.5 | 4 | <QL | <QL | <QL | <QL |
| Silver | 97 | <0.5 | <QL | <QL | <QL | <QL | 17 | <QL | <QL | <QL | <QL |
| Ruthenium | 97 | <0.5 | 1 | 0.73 | <QL | <0.5 | 2 | 0.73 | <QL | 0.004 | 0.001 |
| Rhodium | 97 | <0.5 | 4 | 4.29 | <QL | <0.5 | 8 | 4.28 | 0.005 | 0.005 | 0.006 |
| Platinum | 97 | <0.5 | <0.5 | <QL | <QL | <0.5 | 1 | <QL | <QL | <QL | <QL |
| Palladium | 97 | <0.5 | <QL | <QL | <QL | <0.5 | 1 | <QL | <QL | 0.02 | 0.02 |
| Osmium | 97 | <0.5 | <QL | <QL | <QL | <0.5 | 1 | <QL | <QL | <QL | <QL |
| Iridium | 97 | <0.5 | 6 | 5.95 | <QL | <0.5 | 7 | 5.94 | 0.03 | 0.03 | 0.03 |
| Thallium | 78 | <0.5 | 4 | 3.59 | <QL | <0.5 | 5 | 3.56 | <QL | <QL | <QL |
| Cobalt | 48 | <0.5 | <0.5 | <QL | <QL | <0.5 | <0.5 | <QL | <QL | <QL | <QL |
| Lead | 48 | 2 | 6 | 5.51 | 1.9 | 2 | 6 | 5.55 | 2 | 2 | 2 |

TABLE 22-continued

Elemental Impurity Leachables Results for L-Cysteine HCl Injection [X] (ppb)

| | | | | | | | | | | |
|---|---|---|---|---|---|---|---|---|---|---|
| Mercury | 29 | <0.5 | 1 | 0.98 | 1.2 | <0.5 | 1 | 0.89 | 0.7 | 0.7 | 0.7 |
| Cadmium | 19 | <0.5 | 1.30 | 1.29 | <QL | <0.5 | 2 | 1.29 | <QL | <QL | <QL |

| | | XMHJ1702A 25° C./60% RH | | XMHJ1702A 25° C./60% RH | | | | XMHJ1702A 40° C./75% RH | | | |
|---|---|---|---|---|---|---|---|---|---|---|---|
| | | | | Time point (months) | | | | | | | |
| Element | AEC (ppb) | 9 INV | 9 UP | 0 | 1 | 2 | 3 | 6 | 0 | 1 | 2 | 3 | 6 |
| Molybdenum | 14537 | 1 | 0.5 | 2 | N/A | N/A | 1.34 | 0.5 | 2 | 2 | <0.5 | 1 | 0.4 |
| Zinc | 12598 | 17 | 17 | 42 | N/A | N/A | 3.90 | 34.3 | 42 | 37 | 2 | 4 | 22.1 |
| Iron | 12598 | 5 | 59 | 284 | N/A | N/A | 15.31 | 7 | 284 | 27 | <QL | 35 | 11.2 |
| Chromium | 10660 | 5 | 1 | 14 | N/A | N/A | <QL | 2.1 | 14 | 4 | <0.5 | <QL | 2.1 |
| Barium | 6784 | 1 | 0.4 | 2 | N/A | N/A | <QL | <QL | 2 | 2 | <QL | <QL | <QL |
| Tin | 5815 | 2 | 1 | 3 | N/A | N/A | 1.82 | 3.8 | 3 | 3 | 2 | 2 | 1 |
| Copper | 2907 | 1 | 0.4 | 4 | N/A | N/A | <QL | 123.1 | 4 | 2 | <QL | <QL | 0.1 |
| Manganese | 2423 | 2 | 1 | 5 | N/A | N/A | <QL | 0.1 | 5 | 1 | <0.5 | <QL | 0.3 |
| Lithium | 2423 | 8 | 0.1 | 6 | N/A | N/A | 3.92 | 0.2 | 6 | 6 | <QL | 4 | 0.2 |
| Gold | 969 | 7 | 1 | 7 | N/A | N/A | 3.45 | 0.1 | 7 | 4 | 5 | 4 | 0.1 |
| Antimony | 872 | <QL | 0.3 | 2 | N/A | N/A | 1.08 | <QL | 2 | 2 | 1 | 1 | <QL |
| Selenium | 775 | <QL | <QL | 4 | N/A | N/A | <QL | 0.4 | 4 | 2 | <QL | <QL | <QL |
| Nickel | 194 | 11 | 15 | 11 | N/A | N/A | 8.93 | 8 | 11 | 9 | 4 | 8 | 8.1 |
| Arsenic | 174 | 0.3 | 0.1 | 2 | N/A | N/A | <QL | 0.3 | 2 | 1 | <QL | <QL | 0.3 |
| Aluminum | 120 | (9) <QL | (5) <QL | <0.5 | N/A | N/A | <QL | <QL | <QL <QL | (3) <QL | (8) <QL | (7) <QL | <QL |
| Vanadium | 97 | 3 | <QL | 4 | N/A | N/A | <QL | <QL | 4 | 3 | <QL | <QL | <QL |
| Silver | 97 | 2 | <QL | 17 | N/A | N/A | <QL | <QL | 17 | 17 | 17 | <QL | <QL |
| Ruthenium | 97 | 0.9 | <QL | 2 | N/A | N/A | 0.76 | <QL | 2 | 2 | <0.5 | 1 | <QL |
| Rhodium | 97 | 8 | 0.01 | 8 | N/A | N/A | 4.30 | <QL | 8 | 8 | 9 | 4 | <QL |
| Platinum | 97 | 2 | <QL | 1 | N/A | N/A | <QL | 0.1 | 1 | 1 | <0.5 | <0.5 | 0.1 |
| Palladium | 97 | 1 | 0.1 | 1 | N/A | N/A | <QL | <QL | 1 | 1 | <QL | <QL | <QL |
| Osmium | 97 | 0.8 | <QL | 1 | N/A | N/A | <QL | <QL | 1 | 1 | 1 | <QL | <QL |
| Iridium | 97 | 10 | 0.04 | 7 | N/A | N/A | 5.98 | <QL | 7 | 7 | 9 | 6 | <QL |
| Thallium | 78 | 7 | <QL | 5 | N/A | N/A | 3.59 | <QL | 5 | 5 | 6 | 4 | <QL |
| Cobalt | 48 | 3 | 0.03 | <0.5 | N/A | N/A | <QL | <QL | <0.5 | <0.5 | <QL | <0.5 | <QL |
| Lead | 48 | 8 | 2 | 6 | N/A | N/A | 5.01 | 1.6 | 6 | 6 | 6 | 5 | 1.5 |
| Mercury | 29 | 1 | 0.6 | 2 | N/A | N/A | 0.81 | 1 | 2 | 1 | 1 | 1 | 1.1 |
| Cadmium | 19 | 0.5 | <QL | 2 | N/A | N/A | 1.37 | <QL | 2 | 2 | 1 | 1 | <QL |

| | | XMHJ1702B 40° C./75% RH | | | | | XMHJ1702B 25° C./60% RH | | | | |
|---|---|---|---|---|---|---|---|---|---|---|---|
| | | Time point (months) | | | | | | | | | |
| | | 0 | 1 | 2 | 3 | 6 | 0 | 1 | 2 | 3 | 6 |
| Molybdenum | 14537 | 2 | N/A | N/A | 1 | 0.5 | 2 | 2 | <QL | 1 | 0.4 |
| Zinc | 12598 | 38 | N/A | N/A | 71 | 23.5 | 38 | 39 | <QL | 7 | 23.1 |
| Iron | 12598 | 166 | N/A | N/A | 31 | 7.9 | 166 | 35 | <QL | 16 | 12.3 |
| Chromium | 10660 | 9 | N/A | N/A | <QL | <QL | 9 | 6 | <QL | <QL | 1.9 |
| Barium | 6784 | 1 | N/A | N/A | <QL | <QL | 1 | 1 | <QL | <QL | <QL |
| Tin | 5815 | 3 | N/A | N/A | 21 | 1.5 | 3 | 4 | 3 | 3 | 1.3 |
| Copper | 2907 | 2 | N/A | N/A | <QL | <QL | 2 | 2 | <QL | <QL | 0.3 |
| Manganese | 2423 | 3 | N/A | N/A | <QL | 0.1 | 3 | 1 | <QL | <QL | 0.3 |
| Lithium | 2423 | 6 | N/A | N/A | 4 | 0.2 | 6 | 6 | <QL | 4 | 0.2 |
| Gold | 969 | 5 | N/A | N/A | 3 | 0.1 | 5 | 4 | 5 | 3 | 0.1 |
| Antimony | 872 | 2 | N/A | N/A | 1 | <QL | 2 | 2 | 1 | 1 | <QL |
| Selenium | 775 | 3 | N/A | N/A | <QL | 0.1 | 3 | 2 | <QL | <QL | <QL |
| Nickel | 194 | 10 | N/A | N/A | 9 | 8.2 | 10 | 8 | 4 | 8 | 8.2 |
| Arsenic | 174 | 2 | N/A | N/A | <QL | 0.3 | 2 | 2 | <QL | <QL | 0.1 |
| Aluminum | 120 | <QL | N/A | N/A | (6) <QL | <QL | <QL | (10) <QL | (25) <QL | (6) <QL | <QL |
| Vanadium | 97 | 4 | N/A | N/A | <QL | <QL | 4 | 4 | <QL | <QL | <QL |
| Silver | 97 | 17 | N/A | N/A | <QL | <QL | 17 | 17 | 17 | <QL | <QL |
| Ruthenium | 97 | 2 | N/A | N/A | 1 | <QL | 2 | 2 | <0.5 | 1 | <QL |
| Rhodium | 97 | 8 | N/A | N/A | 4 | <QL | 8 | 8 | 9 | 4 | <QL |
| Platinum | 97 | 1 | N/A | N/A | <0.5 | 0.1 | 1 | 1 | <0.5 | <0.5 | 0.1 |
| Palladium | 97 | 1 | N/A | N/A | <QL | <QL | 1 | 1 | <QL | <QL | <QL |
| Osmium | 97 | 1 | N/A | N/A | <QL | <QL | 1 | 1 | 1 | <QL | <QL |
| Iridium | 97 | 7 | N/A | N/A | 6 | <QL | 7 | 7 | 9 | 6 | <QL |
| Thallium | 78 | 5 | N/A | N/A | 4 | <QL | 5 | 5 | 6 | 4 | <QL |
| Cobalt | 48 | <0.5 | N/A | N/A | <0.5 | <QL | <0.5 | <0.5 | <QL | <0.5 | <QL |
| Lead | 48 | 6 | N/A | N/A | 5 | 1.5 | 6 | 6 | 6 | 5 | 1.5 |
| Mercury | 29 | 2 | N/A | N/A | 1 | 0.5 | 2 | 1 | 1 | 1 | 0.4 |
| Cadmium | 19 | 2 | N/A | N/A | 1 | <QL | 2 | 2 | 1 | 1 | <QL |

Example 10

Visual Inspection of Filled Vials

The L-Cysteine product that was manufactured by the two methods (i.e., lyophilzer chamber method and high-speed filler method) were inspected at after 1 month after production for visible signs of degradation in the form of visible particulate matter. In the presence of oxygen, two L-Cysteine residues will form a disulfide covalent bond forming L-Cystine. L-Cystine has a lower solubility (0.112 mg/mL) than L-Cysteine (50 mg/mL), in some cases the degradant can be visually observed.

TABLE 23

Comparison of Particulate Matter

|  | PROT-000213 | XMHJ1705 | XMHJ1706 | XMHJ1707 |
|---|---|---|---|---|
| Total Vials | 1918 | 3473 | 3473 | 3497 |
| White PM | 36 | 120 | 31 | 32 |
| Overall % | 1.88% | 3.46% | 0.89% | 0.92% |

As the data show, no confirmed degradation was observed by either method indicating that the head space oxygen reduction and dissolved oxygen levels achieved herein are successful in producing L-Cysteine injection of desirable quality attributes.

All documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "consists essentially of" (and grammatical variants), as applied to the compositions of this invention, means the composition can contain additional components as long as the additional components do not materially alter the composition.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 milligrams to about 80 milligrams" should also be understood to provide support for the range of "50 milligrams to 80 milligrams." Furthermore, it is to be understood that in this written description support for actual numerical values is provided even when the term "about" is used therewith. Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount. To be clear, the range encompassed by "about" will include all discrete values within that range, regardless of whether such discrete values are explicitly specified and/or prefaced by "about." Equivalents permissible for such discrete values as well as all ranges and subranges are within the scope of this disclosure.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed:

1. A composition for injection comprising a mixture of:
  a L-cysteine composition, wherein the L-cysteine composition contributes to the composition for injection:
    L-cysteine or a pharmaceutically acceptable salt thereof and/or hydrate thereof in an amount from about 10 mg/mL to about 100 mg/mL;
    not more than 250 mcg/L of aluminum; and
    not more than 2.0 wt % L-cysteine relative to L-cysteine;
  one or more amino acids selected from the group consisting of: leucine, isoleucine, lysine, valine, phenylalanine, histidine, threonine, methionine, tryptophan, alanine, arginine, glycine, proline, serine, and tyrosine; and,
  an intravenous fluid.

2. The composition for injection of claim 1, wherein the L-cysteine composition provides not more than 0.8 mcg/kg/day of aluminum when administered as part of a parenteral nutrition regimen.

3. The composition for injection of claim 1, wherein the L-cysteine composition provides not more than 0.6 mcg/kg/day of aluminum when administered as part of a parenteral nutrition regimen.

4. The composition for injection of claim 1, wherein the L-cysteine composition provides not more than 0.4 mcg/kg/day of aluminum when administered as part of a parenteral nutrition regimen.

5. The composition for injection of claim 1, wherein the L-cysteine composition provides not more than 0.21 mcg/kg/day of aluminum when administered as part of a parenteral nutrition regimen.

6. The composition for injection of claim 1, wherein the composition for injection provides not more than 5 mcg/kg/day of aluminum when administered as part of a parenteral nutrition regimen.

7. The composition for injection of claim 1, wherein the composition for injection provides not more than 4 mcg/kg/day of aluminum when administered as part of a parenteral nutrition regimen.

8. The composition for injection of claim 1, wherein the composition for injection provides not more than 3 mcg/kg/day of aluminum when administered as part of a parenteral nutrition regimen.

9. The composition for injection of claim 1, wherein the intravenous fluid is selected from the group consisting of isotonic saline, glucose solution, glucose saline, dextrose solution, crystalline amino acid solution, and lipids, and combinations thereof.

10. The composition for injection of claim 9, wherein the intravenous fluid is selected from the group consisting of isotonic saline, dextrose solution, crystalline amino acid solution, and combinations thereof.

11. The composition for injection of claim 1, wherein the intravenous fluid comprises dextrose solution.

12. A composition for injection comprising a mixture of:
a L-cysteine composition, wherein the L-cysteine composition contributes to the composition for injection:
L-cysteine or a pharmaceutically acceptable salt thereof and/or hydrate thereof in an amount of about 50 mg/mL;
not more than 120 ppb of aluminum; and
not more than 1.0 wt % L-cysteine relative to L-cysteine;
one or more amino acids selected from the group consisting of: leucine, isoleucine, lysine, valine, phenylalanine, histidine, threonine, methionine, tryptophan, alanine, arginine, glycine, proline, serine, and tyrosine; and,
an intravenous fluid;
wherein, the L-cysteine composition provides not more than 0.21 mcg/kg/day of aluminum, and the composition for injection provides not more than 5 mcg/kg/day of aluminum, when administered as part of a parenteral nutrition regimen.

13. The composition of claim 12, wherein the L-cysteine composition has a pH of about 1.0 to about 2.5.

14. The composition of claim 12, wherein the intravenous fluid comprises dextrose solution.

15. A method of treating a subject having an adverse health condition that is responsive to L-cysteine administration, said method comprising:
parenterally administering to said subject a composition for injection comprising a mixture of:
a L-cysteine composition, wherein the L-cysteine composition contributes to the composition for injection:
L-cysteine or a pharmaceutically acceptable salt thereof and/or hydrate thereof in an amount from about 10 mg/mL to about 100 mg/mL;
not more than 250 mcg/L of aluminum; and
not more than 2.0 wt % L-cysteine relative to L-cysteine;
one or more amino acids selected from the group consisting of: leucine, isoleucine, lysine, valine, phenylalanine, histidine, threonine, methionine, tryptophan, alanine, arginine, glycine, proline, serine, and tyrosine;
and,
an intravenous fluid.

16. The method of claim 15, wherein the L-cysteine composition contributes to the composition for injection:
L-cysteine or a pharmaceutically acceptable salt thereof and/or hydrate thereof in an amount of about 50 mg/mL;
not more than 120 mcg/L of aluminum; and
not more than 1.0 wt % L-cysteine relative to L-cysteine.

17. The method of claim 15, wherein said L-cysteine composition contributes aluminum in an amount less than 200 mcg/L.

18. The method of claim 15, wherein said L-cysteine composition contributes aluminum in an amount less than 150 mcg/L.

19. The method of claim 15, wherein said L-cysteine composition contributes aluminum in an amount less than 120 mcg/L.

20. The method of claim 15, wherein the intravenous fluid is selected from the group consisting of isotonic saline, glucose solution, glucose saline, dextrose solution, crystalline amino acid solution, and lipids, and combinations thereof.

21. The method of claim 20, wherein said intravenous fluid is selected from the group consisting of isotonic saline, dextrose solution, and crystalline amino acid solution, and combinations thereof.

22. The method of claim 21, wherein said intravenous fluid is dextrose solution.

23. The method of claim 15, wherein said administering comprises administration once or twice daily.

24. The method of claim 15, wherein said subject is an adult or has an age of 12 years to 17 years and said administering delivers about 15 nag of said L-cysteine per gram of said one or more amino acids.

25. The method of claim 15, wherein said subject is less than 12 years of age and said administering delivers about 5 mg of said L-cysteine per gram of said one or more amino acids.

26. The method of claim 15, wherein and said L-cysteine composition contributes not more than 0.21 mcg/kg/day of aluminum.

27. The method of claim 15, wherein and said composition for injection provides not more than 5 mcg/kg/day of aluminum.

28. The method of claim 15, wherein said adverse health condition results from the inability to convert methionine to L-cysteine.

29. The method of claim 15, wherein the adverse health condition is the need for parenteral nutrition.

30. A method of treating a subject having an adverse health condition that is responsive to L-cysteine administration, said method comprising:
parenterally administering to said subject a composition comprising a mixture of:
a L-cysteine composition, wherein the L-cysteine composition contributes to the composition for injection:
L-cysteine or a pharmaceutically acceptable salt thereof and/or hydrate thereof in an amount of about 50 mg/mL;
not more than 120 mcg/L of aluminum; and
not more than 1.0 wt % L-cysteine relative to L-cysteine;
one or more amino acids selected from the group consisting of: leucine, isoleucine, lysine, valine, phenylalanine, histidine, threonine, methionine, tryptophan, alanine, arginine, glycine, proline, serine, and tyrosine;

and,
   an intravenous fluid;
wherein, the L-cysteine composition provides not more than 0.21 mcg/kg/day of aluminum, and the composition for injection provides not more than 5 mcg/kg/day of aluminum, when administered as part of a parenteral nutrition regimen.

31. The method of claim 30, wherein said subject is an adult or has an age of 12 years to 17 years and said administering delivers about 15 mg of said L-cysteine per gram of said one or more amino acids.

32. The method of claim 30, wherein said subject is less than 12 years of age and said administering delivers about 5 mg of said L-cysteine per gram of said one or more amino acids.

33. The method of claim 32, wherein the adverse health condition is the need for parenteral nutrition.

34. A method of preparing a reduced aluminum composition for a parenteral nutrition regimen comprising L-cysteine, the method comprising:
   mixing a composition comprising:
      L-cysteine or a pharmaceutically acceptable salt thereof and/or hydrate thereof in an amount of about 50 mg/mL; not more than 120 ppb of aluminum;
   and not more than 1.0% L-cysteine relative to L-cysteine;
   with,
      a composition comprising one or more amino acids selected from the group consisting of: leucine, isoleucine, lysine, valine, phenylalanine, histidine, threonine, methionine, tryptophan, alanine, arginine, glycine, proline, serine, and tyrosine;
   and,
      an intravenous fluid,
   to prepare the reduced aluminum composition for a parenteral nutrition regimen.

* * * * *

UNITED STATES PATENT AND TRADEMARK OFFICE
CERTIFICATE OF CORRECTION

| | |
|---|---|
| PATENT NO. | : 11,510,942 B1 |
| APPLICATION NO. | : 17/188922 |
| DATED | : November 29, 2022 |
| INVENTOR(S) | : Maloney et al. |

It is certified that error appears in the above-identified patent and that said Letters Patent is hereby corrected as shown below:

In the Claims

Column 58,
Lines 44-45, "L-cysteine relative to L-cysteine" should read --L-cystine relative to L-cysteine--.

Column 59,
Lines 31-32 and Lines 59-60, "L-cysteine relative to L-cysteine", each occurrence, should read
--L-cystine relative to L-cysteine--.

Column 60,
Line 7 and Lines 61-62, "L-cysteine relative to L-cysteine", each occurrence, should read --L-cystine relative to L-cysteine--.
Line 33, "15 nag" should read --15 mg--.

Column 62,
Line 8, "L-cysteine relative to L-cysteine", each occurrence, should read --L-cystine relative to
L-cysteine--.

Signed and Sealed this
Seventeenth Day of October, 2023

*Katherine Kelly Vidal*
Katherine Kelly Vidal
*Director of the United States Patent and Trademark Office*